(12) United States Patent
Meyers et al.

(10) Patent No.: US 7,166,428 B2
(45) Date of Patent: Jan. 23, 2007

(54) 62112, A NOVEL HUMAN DEHYDROGENASE AND USES THEREOF

(75) Inventors: Rachel Meyers, Newton, MA (US); John Joseph Hunter, Somerville, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/945,326

(22) Filed: Aug. 31, 2001

(65) Prior Publication Data

US 2002/0127680 A1 Sep. 12, 2002

Related U.S. Application Data

(60) Provisional application No. 60/229,831, filed on Aug. 31, 2000.

(51) Int. Cl.
*C12Q 1/68* (2006.01)
(52) U.S. Cl. .......................... 435/6; 436/518
(58) Field of Classification Search ................ 435/4, 435/7.1, 7.93, 26
See application file for complete search history.

(56) References Cited

FOREIGN PATENT DOCUMENTS

| EP | 1074617 A2 | 2/2001 |
|---|---|---|
| WO | WO 00/58473 A2 | 10/2000 |
| WO | WO 01/44448 A2 | 6/2001 |
| WO | WO 01/44448 A3 | 6/2001 |
| WO | WO 01/55301 A2 | 8/2001 |

OTHER PUBLICATIONS

Gura (Science, 1997 , 278:1041-1042).*
Jain (Sci. Am., 1994, 271:58-65).*
Curti (Crit. Rev. in Oncology/Hematology, 1993, 14:29-39).*
Hartwell et al (Science, 1997 , 278:1064-1068).*
Wang, J. et al. 2000 J. Biol. Chem. 275 (1): 507-513.*
Bowie et al (Science, 1990, 247:1306-1310).*
Burgess et al (J of Cell Bio. 111:2129-2138, 1990).*
Lazar et al (Molecular and Cellular Biology, 1988, 8:1247-1252).*
Aoyama et al, (1994, J. Biol. Chem. vol. 269, pp. 19088-19094).*
The definition of "ameliorate" in Merriam-Webster Online dictionary downloaded from url>>m-w.com.*
Voet et al., (Biochemistry, John Wileys &Sons, 1990, pp. 284-289).*
Voet et al (1990, Biochemistry, John Wiley & Sons, p. 507).*
Scott et al (Nature Genetics, 1999, 21:440-443).*
Skolnick et al. (2000, Trends in Biotech. 18:34-39).*
Bork (2000, Genome Research 10:398-400).*
Doerks et al. (1998, Trends in Genetics 14:248-250).*
Brenner (1999, Trends in Genetics 15:132-133).*
Bork et al. (1996, Trends in Genetics 12:425-427).*
Bowie et al. (1990, Science 247:1306-1310).*
Johnson et al. (Brit. J. Cancer 84(10):1424-1431).*
Shi et al., (J. Chem. Inf. Comput. Sci. 40:367-379).*
Smith et al. (1997 , Nature Biotechnology 15:1222-1223).*
Aoyama, T. et al., "Cloning of human very-long-chain acyl-coenzyme A dehydrogenase and molecular characterization of its deficiency in two patients," Am J Hum Genet., Aug. 1995; 57(2):273-83.
EMBL Accession No. AAB94839 for human protein sequence SEQ ID N:16010. Jun. 26, 2001.
EMBL Accession No. AAH16781 for Human cDNA sequence SEQ ID N:16009. Jun. 26, 2001.
EMBL Accession No. AAS40878 for cDNA encoding novel human enzyme polypeptide #94. Dec. 17, 2001.
EMBL Accession No. AAU23008 for Novel human enzyme polypeptide #94. Dec. 17, 2001.
EMBL Accession No. AK024012 for *Homo sapiens* cDNA FLJ13950 fis, clone Y97AA1001048, weakly similar to ACYL-COA Dehydrogenase, Very-Long-Change Precursor (EC 1.3.99.-). Sep. 28, 2000.
EMBL Accession No. BE615243 for 601281562F1 NIH_MGC_39 *Homo sapiens* cDNA clone IMAGE:3623559 5', mRNA sequence. Aug. 25, 2000.
GenBank Accession No. P50544 for Acyl-CoA dehydrogenase, very-long-chain specific, mitochondrial precursor (VLCAD) (MVLCAD).
GenBank Accession No. T15905 for hypothetical protein E04F6.1—Caenorhabditis elegans.
GenBank Accession No. W40274 for zc80g09.r1 Pancreatic Islet *Homo sapiens* cDNA clone Image:328672 5'similar to SW:ACDV_RAT P45953 ACYL-COA Dehydrogenase, Very-Long-Chain Specific Precursor ;, mRNA sequence.
GenBank Accession No. AF078854 for *Homo sapiens* NPD002 mRNA, complete cds.
GenBank Accession No. AK022568 for *Homo sapiens* cDNA FLJ12506 fis, clone NT2RM2001700, weakly similar to ACYL-COA Dehydrogenase, Very-Long-Chain Specific (EC 1.3.99.-).
GenBank Accession No. AK024012 for *Homo sapiens* cDNA FLJ13950 fis, clone Y79AA1001048, weakly similar to ACYL-COA Dehydrogenase, Very-Long-Chain Specific Precursor (EC 1.3.99.-).
GenBank Accession No. BC007970 for *Homo sapiens*, clone MGC:14452 IMAGE:4304209, mRNA, complete cds.
GenBank Accession No. BE206217 for ba93d09.x1 NIH_MGC_5 *Homo sapiens* cDNA clone Image:2924849 3' similar to SW:ACDV_BOVIN P48818 ACYL-COA Dehydrogenase, Very-Long-Chain Specific Precursor ;, mRNA sequence.

(Continued)

*Primary Examiner*—Misook Yu
(74) *Attorney, Agent, or Firm*—Millennium Pharmaceuticals, Inc.

(57) ABSTRACT

The invention provides isolated nucleic acids molecules, designated DHDR-7 nucleic acid molecules, which encode novel human dehydrogenase molecules. The invention also provides antisense nucleic acid molecules, recombinant expression vectors containing DHDR-7 nucleic acid molecules, host cells into which the expression vectors have been introduced, and nonhuman transgenic animals in which a DHDR-7 gene has been introduced or disrupted. The invention still further provides isolated DHDR-7 polypeptides, fusion polypeptides, antigenic peptides and anti-DHDR-7 antibodies. Diagnostic methods utilizing compositions of the invention are also provided.

9 Claims, 9 Drawing Sheets

OTHER PUBLICATIONS

GenBank Accession No. BAB14104 for unnamed protein product [*Homo sapiens*].

Cox, K.B. et al. "Chromosomal locations of the mouse fatty acid oxidation genes *Cpt1a, Cpt1b, Cpt2, Acadvl,* and metabolically related *Crat* gene" *Mammalian genome* 9:608-610 (1998).

Strausberg, R., "*Homo sapiens* acyl-Coenzym A dehydrogenase family, member 9, mRNA (cDNA close MGC:14970 IMAGE: 3935925), complete cds." NCBI [online] Bethesda, MD: National Center for Biotechnology Information [Retrieved on Nov. 8, 2005]. Retrieved from the internet: <URL: http://www.ncbi.nlm.nih.gov/entrez/viewer.fcgi?db=nucleotide&val=33989435/>. NCBI Accession No. BC013354.

\* cited by examiner

```
Input file Fbh62112FL.seq; Output File 62112.trans
Sequence length 2452
                                                                          M   S   G     3
CGTGTGTGTGTCCCTGCGGCGCTAAGAAGGGGAGACTGAGGCTGAGGCTGGGGAACATCGGCAGC ATG AGC GGC    9

C   G   L   F   L   R   T   T   A   A   A   R   A   C   R   G   L   V   V   S    23
TGC GGG CTC TTC CTG CGC ACC ACG GCT GCG GCT CGT GCC TGC CGG GGT CTG GTG GTC TCT    69

T   A   N   R   R   L   L   R   T   S   P   P   V   R   A   F   A   K   E   L    43
ACC GCG AAC CGG CGG CTA CTG CGC ACC AGC CCG CCT GTA CGA GCT TTC GCC AAA GAG CTT   129

F   L   G   K   I   K   K   K   E   V   F   P   F   P   E   V   S   Q   D   E    63
TTC CTA GGC AAA ATC AAG AAG AAA GAA GTT TTC CCA TTT CCA GAA GTT AGC CAA GAT GAA   189

L   N   E   I   N   Q   F   L   G   P   V   E   K   F   F   T   E   E   V   D    83
CTT AAT GAA ATC AAT CAG TTC TTG GGA CCC GTG GAA AAA TTC TTC ACT GAA GAG GTG GAC   249

S   R   K   I   D   Q   E   G   K   I   P   D   E   T   L   E   K   L   K   S   103
TCC CGA AAA ATT GAC CAG GAA GGG AAA ATC CCA GAT GAA ACT TTG GAG AAA TTG AAG AGC   309

L   G   L   F   G   L   Q   V   P   E   E   Y   G   G   L   G   F   S   N   T   123
CTA GGG CTT TTT GGG CTG CAA GTC CCA GAA GAA TAT GGT GGC CTG GGC TTC TCC AAC ACC   369

M   Y   S   R   L   G   E   I   I   S   M   D   G   S   I   T   V   T   L   A   143
ATG TAC TCA AGA CTA GGG GAG ATC ATC AGC ATG GAT GGG TCC ATC ACT GTG ACC CTG GCA   429

A   H   Q   A   I   G   L   K   G   I   I   L   A   G   T   E   E   Q   K   A   163
GCG CAC CAG GCT ATT GGC CTC AAG GGG ATC ATC TTG GCT GGC ACT GAG GAG CAG AAA GCC   489

K   Y   L   P   K   L   A   S   G   E   H   I   A   A   F   C   L   T   E   P   183
AAA TAC TTG CCT AAA CTG GCG TCC GGG GAG CAC ATT GCA GCC TTC TGC CTC ACG GAG CCA   549

A   S   G   S   D   A   A   S   I   R   S   R   A   T   L   S   E   D   K   K   203
GCC AGT GGG AGC GAT GCA GCC TCA ATC CGG AGC AGA GCC ACA CTA AGT GAA GAC AAG AAG   609

H   Y   I   L   N   G   S   K   V   W   I   T   N   G   G   L   A   N   I   F   223
CAC TAC ATC CTC AAT GGC TCC AAG GTC TGG ATT ACT AAT GGA GGA CTG GCC AAT ATT TTT   669

T   V   F   A   K   T   E   V   V   D   S   D   G   S   V   K   D   K   I   T   243
ACT GTG TTT GCA AAG ACT GAG GTC GTT GAT TCT GAT GGA TCA GTG AAA GAC AAA ATC ACA   729

A   F   I   V   E   R   D   F   G   G   V   T   N   G   K   P   E   D   K   L   263
GCA TTC ATA GTA GAA AGA GAC TTT GGT GGA GTC ACT AAT GGG AAA CCC GAA GAT AAA TTA   789

G   I   R   G   S   N   T   C   E   V   H   F   E   N   T   K   I   P   V   E   283
GGC ATT CGG GGC TCC AAC ACT TGT GAA GTC CAT TTT GAA AAC ACC AAG ATA CCT GTG GAA   849

N   I   L   G   E   V   G   D   G   F   K   V   A   M   N   I   L   N   S   G   303
AAC ATC CTT GGA GAG GTC GGA GAT GGG TTT AAG GTG GCC ATG AAC ATC CTC AAC AGC GGC   909

R   F   S   M   G   S   V   V   A   G   L   L   K   R   L   I   E   M   T   A   323
CGG TTC AGC ATG GGC AGC GTC GTG GCT GGG CTG CTC AAG AGA TTG ATT GAA ATG ACT GCT   969

E   Y   A   C   T   R   K   Q   F   N   K   R   L   S   E   F   G   L   I   Q   343
GAG TAC GCC TGC ACA AGG AAA CAG TTT AAC AAG AGG CTC AGT GAA TTT GGA TTG ATT CAG  1029

E   K   F   A   L   M   A   Q   K   A   Y   V   M   E   S   M   T   Y   L   T   363
GAG AAA TTT GCA CTG ATG GCT CAG AAG GCT TAC GTC ATG GAG AGT ATG ACC TAC CTC ACA  1089

A   G   M   L   D   Q   P   G   F   P   D   C   S   I   E   A   A   M   V   K   383
GCA GGG ATG CTG GAC CAA CCT GGC TTT CCC GAC TGC TCC ATC GAG GCA GCC ATG GTG AAG  1149
```

Fig. 1A

```
      V   F   S   S   E   A   A   W   Q   C   V   S   E   A   L   Q   I   L   G   G   403
     GTG TTC AGC TCC GAG GCC GCC TGG CAG TGT GTG AGT GAG GCG CTG CAG ATC CTC GGG GGC 1209

L   G   Y   T   R   D   Y   P   Y   E   R   I   L   R   D   T   R   I   L   L   423
     TTG GGC TAC ACA AGG GAC TAT CCG TAC GAG CGC ATA CTG CGT GAC ACC CGC ATC CTC CTC 1269

I   F   E   G   T   N   E   I   L   R   M   Y   I   A   L   T   G   L   Q   H   443
     ATC TTC GAG GGA ACC AAT GAG ATT CTC CGG ATG TAC ATC GCC CTG ACG GGT CTG CAG CAT 1329

A   G   R   I   L   T   T   R   I   H   E   L   K   Q   A   K   V   S   T   V   463
     GCC GGC CGC ATC CTG ACT ACC AGG ATC CAT GAG CTT AAA CAG GCC AAA GTG AGC ACA GTC 1389

M   D   T   V   G   R   R   L   R   D   S   L   G   R   T   V   D   L   G   L   483
     ATG GAT ACC GTT GGC CGG AGG CTT CGG GAC TCC CTG GGC CGA ACT GTG GAC CTG GGG CTG 1449

T   G   N   H   G   V   V   H   P   S   L   A   D   S   A   N   K   F   E   E   503
     ACA GGC AAC CAT GGA GTT GTG CAC CCC AGT CTT GCG GAC AGT GCC AAC AAG TTT GAG GAG 1509

N   T   Y   C   F   G   R   T   V   E   T   L   L   L   R   F   G   K   T   I   523
     AAC ACC TAC TGC TTC GGC CGG ACC GTG GAG ACA CTG CTG CTC CGC TTT GGC AAG ACC ATC 1569

M   E   E   Q   L   V   L   K   R   V   A   N   I   L   I   N   L   Y   G   M   543
     ATG GAG GAG CAG CTG GTA CTG AAG CGG GTG GCC AAC ATC CTC ATC AAC CTG TAT GGC ATG 1629

T   A   V   L   S   R   A   S   R   S   I   R   I   G   L   R   N   H   D   H   563
     ACG GCC GTG CTG TCG CGG GCC AGC CGC TCC ATC CGC ATT GGG CTC CGC AAC CAC GAC CAC 1689

E   V   L   L   A   N   T   F   C   V   E   A   Y   L   Q   N   L   F   S   L   583
     GAG GTT CTC TTG GCC AAC ACC TTC TGC GTG GAA GCT TAC TTG CAG AAT CTC TTC AGC CTC 1749

S   Q   L   D   K   Y   A   P   E   N   L   D   E   Q   I   K   K   V   S   Q   603
     TCT CAG CTG GAC AAG TAT GCT CCA GAA AAC CTA GAT GAG CAG ATT AAG AAA GTG TCC CAG 1809

Q   I   L   E   K   R   A   Y   I   C   A   H   P   L   D   R   T   C   *       622
     CAG ATC CTT GAG AAG CGA GCC TAT ATC TGT GCC CAC CCT CTG GAC AGG ACA TGC TGA     1866

GGCAGGGGACAGTGTCCCCTGCTACCGCCCGCCCCTACCCATGGCCCGTTGCTGGATGACTGTTACTCTTTTTTCAGAA

GGTGTTGGGATTATCACAGGTTAAGCCTTTTGTTCCCCGTCTGCACCTGAAGGGTTGTCGCCTGGCCTGGGAGAGCCTC

TTCCAGGTTTTGACCTGCAGGCAGTGCTCTCTAACAGGACCATCACAGCTTCTGAACTGAGCCGGAGAGAGAGAATGGA

ATTGCTGACCCCTGGAACTGGCGGGTATTCTGGTCATTGAGGAGACACCATAGTGGAAACTGGGGCTTATGCTGCTGCC

TCCAGGGTGTGAGGTGGGTGGGACCTGTGTCAGGTGTGGATAGCCATTTCTGCTCAACCACACATTCTCTAAGAAACA

GCTTGAAAGCTCTGTCTGGGTCATTCATTTAAACTAGAAGCAGAGGCACTTAAAACATGTACCAGGAACCATTTAACAA

AGAATATAAAATGTCACAATCTGTGTACTGTTAAAAAAAAAAAAAA
```

Fig. 1B

Protein Family / Domain Matches, HMMer version 2

Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - -
HMM file:              /prod/ddm/seqanal/PFAM/pfam6.4/Pfam
Sequence file:         /prod/ddm/wspace/orfanal/oa-script.26629.seq
- - - - - - - - - - - - - - - - - - - - - - - - - - - - - - - - - - -
Query:  62112

Scores for sequence family classification (score includes all domains):
Model            Description                              Score      E-value   N
--------         -----------                              -----      -------   ---
Acyl-CoA_dh_M    Acyl-CoA dehydrogenase, middle domain    153.0      3.5e-42   1
Acyl-CoA_dh      Acyl-CoA dehydrogenase, C-terminal dom   152.1      9.6e-42   1
Acyl-CoA_dh_N    Acyl-CoA dehydrogenase, N-terminal dom   73.7       4.2e-19   1
Polysac_deacet   Polysaccharide deacetylase               -43.7      1.8       1

Parsed for domains:
Model            Domain   seq-f   seq-t   hmm-f  hmm-t      score    E-value
--------         ------   -----   -----   -----  -----      -----    -------
Acyl-CoA_dh_N    1/1      85      177     ..     29   132 .]  73.7   4.2e-19
Acyl-CoA_dh_M    1/1      179     286     ..     1    106 []  153.0  3.5e-42
Acyl-CoA_dh      1/1      290     441     ..     1    156 []  152.1  9.6e-42
Polysac_deacet   1/1      432     580     ..     1    150 []  -43.7  1.8

Alignments of top-scoring domains:
Acyl-CoA_dh_N: domain 1 of 1, from 85 to 177: score 73.7, E = 4.2e-19
                  *->RRvDksgefPalrelikaLgqlGllginvPEeyGGaGad..ylaRFm
                     R++D++g+ P   e +++L  lGl+g+ vPEeyGG+G +++ ++
         62112  85  RKIDQEGKIP--DETLEKLKSLGLFGLQVPEEYGGLGFSntMYS--- 126

LHAQVaalviEElarvcAstgvilsvhssLgqnpilkfGseEQKkkyLpq
                      + E+   ++s v+l++h ++g+  +i+  +G+eEQK+kyLp+
         62112  127 --------RLGEIISMDGSITVTLAAHQAIGLKGIILAGTEEQKAKYLPK 168 ltsGdliga<-*
                  l+sG++i+a
         62112  169 LASGEHIAA    177

Acyl-CoA_dh_M: domain 1 of 1, from 179 to 286: score 153.0, E = 3.5e-42
                  *->AlTEPgAGSDvgSlkTtAekkEGd..dyiLNGsKmWITNGgqAdwyi
                     +lTEP +GSD++S++ +A+    d+++yiLNGsK+WITNGg A++++
         62112  179 CLTEPASGSDAASIRSRATLS-EDkkHYILNGSKVWITNGGLANIFT 224

VlAvT...DpakkvpgkkgitaFlVekdtpGfsiGkKedKLGlRgSdTcE
                  V+A+T+   D +    + k  itaF+Ve+d+  G++  Gk+edKLG+RgS+TcE
         62112  225 VFAKTevvDSDG--SVKDKITAFIVERDFGGVTNGKPEDKLGIRGSNICE 272

LiFEDvrvPesniL<-*
                  + FE+ ++P +niL
         62112  273 VHFENTKIPVENIL    286

Fig. 2A

```
Acyl-CoA_dh: domain 1 of 1, from 290 to 441: score 152.1, E = 9.6e-42
                *->GkGFkyamkeLdmeRlviAaqalGlaqgaldeAinYakqRkqFGkpl
                   G+GFk+am+ L+ +R+   +++   Gl+ + ++ +++Ya  RkqF k+l
      62112  290  GDGFKVAMNILNSGRFSMGSVVAGLLKRLIEMTAEYACTRKQFNKRL 336 adfQliQfkLAdMatkLEaaRllvYraAwladr.GedAKEALptskeaam
                   +f liQ+k+A Ma k  ++ +++Y +A   d++G +      ++s eaam
      62112  337  SEFGLIQEKFALMAQKAYVMESMTYLTAGMLDQpGFP-----DCSIEAAM 381

AKlfaseaAmqvatdAvQilGGvGYtkdyPveRfyRDAkitqIYEGTsEI
                   +K f+seaA q +++A+QilGG GYt dyP eR +RD +i  I EGT+EI
      62112  382  VKVFSSEAAWQCVSEALQILGGLGYTRDYPYERILRDTRILLIFEGTNEI 431 qrlvIaRall<-*
                   r  Ia + l
      62112  432  LRMYIALTGL     441

Polysac_deacet: domain 1 of 1, from 432 to 580: score -43.7, E = 1.8
                *->ddksvyLTFDDGPnAApayTprlLDvLkkhkvkATFFviGsnvkdnP
                   +++++LT + ++ +   T+r+ + Lk+ kv    +   G++ +d
      62112  432     LRMYIALTGLQHAG--RILTTRI-HELKQAKVSTVMDTVGRRLRD-- 473 dlarrivkeGHeigNHtwsHPdlt.....................tl
                   + r v+ G  gNH+ HP l+++ ++ ++++  +++ ++   +  +
      62112  474  -SLGRIVDLG-LTGNHGVVHPSLAdsankfeentycfgrtvetlllrfGK 521 taeqirdeiertneaiiqatggatptlfRpPYGewsetvlsasaklGlaa
                   t  +++  + r+++++i+++g  t++l R+        s+s ++Gl+
      62112  522  TIMEEQLVLKRVANILINLYG-MTAVLSRA---------SRSIRIGLRN 560 vlWdvDprDWsvragadaivdavlqaa<-*
                   +       D  v   ++   v a+lq+
      62112  561  H-------DHEVLLANTFCVEAYLQNL     580
```

Fig. 2B

```
Protein Family / Domain Matches, HMMer version 2
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - -
HMM file:              /prod/ddm/seqanal/PFAM/pfam5.4/Pfam
Sequence file:         /prod/ddm/wspace/orfanal/oa-script.17193.seq
- - - - - - - - - - - - - - - - - - - - - - - - - - - - - - - - - -
Query:  62112

Scores for sequence family classification (score includes all domains):
Model           Description                              Score     E-value   N
-------         -----------                              -----     -------  ---

Acyl-CoA_dh     Acyl-CoA dehydrogenase                   399.8     1.8e-116  1
Polysac_deacet  Polysaccharide deacetylase               -43.7             1 1

Parsed for domains:
Model           Domain   seq-f  seq-t    hmm-f  hmm-t       score    E-value
-------         ------   -----  -----    -----  -----       -----    -------

Acyl-CoA_dh     1/1      85     438 ..   29     394 .]      399.8    1.8e-116
Polysac_deacet  1/1      432    580 ..   1      150 []      -43.7    1

Alignments of top-scoring domains:
Acyl-CoA_dh: domain 1 of 1, from 85 to 438: score 399.8, E = 1.8e-116
                 *->RRvDksgefPlrelikaLgklGllginvPEeyGGaGad..ylaRFmL
                    R++D++g+ P e +++L  lGl+g+ vPEeyGG+G +++ ++
       62112   85   RKIDQEGKIP-DETLEKLKSLGLFGLQVPEEYGGLGFSntMYS----  126

HAQVaalviEElarvcAstgvllsvhssLgqnpilrfGseEQkkkyLpql
                    + E+   ++s  v+l++h  ++g+   i+  +G+eEQk+kyLp+l
       62112  127   -------RLGEIISMDGSITVILAAHQAIGLKGIILAGTEEQKAKYLPKL  169
```

Fig. 2C

```
              tsGdligafAlTEPgAGSDvgSikTtAekkEGd..dyiLNGsKmWITNGg
              +sG++i+af+lTEP +GSD++Si+ +A+     d+++yiLNGsK+WITNGg
62112   170 ASGEHIAAFCLTEPASGSDAASIRSRATLS-EDkkHYILNGSKVWITNGG 218 qAdwyiVlAvT...DpakkvpgkkgitaFlVekdtpGfsiGkKedKLGlR
              A++++V+A+T+   D +    + k  itaF+Ve+d+ G++ Gk+edKLG+R
62112   219 LANIFTVFAKTevvDSDG--SVKDKITAFIVERDFGGVTNGKPEDKLGIR 266 gSdTcELiFEDvrvPesniLGeEGeGFkyaMktLdmeRlgiAaqalGiaq
              gS TcE+  FE+ ++P +niLGe G+GFk+aM+ L+ +R+   +++  G++
62112   267 GSNTCEVHFENTKIPVENILGEVGDGFKVAMNILNSGRFSMGSVVAGLLK 316 gAldeAinYAkqRkqFGkplaefQliQfkLAdMAtkLEaaRllvYraAwl
              +  ++ +++YA  RkqF  k+l  ef  liQ+k+A MA  k  ++ +++Y +A
62112   317 RLIEMTAEYACTRKQFNKRLSEFGLIQEKFALMAQKAYVMESMTYLTAGM 366 adr.GedAKEALptskeAAMAKlfAseiAmkvatdAvQilGGvGYtkdyP
              d++G +       ++s eAAM+K f+se+A +  +++A+QilGG GYt dyP
62112   367 LDQpGFP-----DCSIEAAMVKVFSSEAAWQCVSEALQILGGLGYTRDYP 411 veRfyRDAkitqIYEGTsEIQrlvIaR<-*
              eR +RD +i  I  EGT+EI r   Ia
62112   412 YERILRDTRILLIFEGTNEILRMYIAL    438

Polysac_deacet: domain 1 of 1, from 432 to 580: score -43.7, E = 1
            *->ddksvyLTFDDGPnAApayTprlLDvLkkhkvkATFFviGsnvkdnP
               +++++LT + ++    + T+r+  + Lk+ kv    +  G++ +d
62112   432    LRMYIALTGLQHAG--RILTTRI-HELKQAKVSTVMDTVGRRLRD-- 473 dlarrivkeGHeigNHtwsHPdlt..................tl
              + r v+ G  gNH+  HP l+++ ++ ++++   +++ ++   + +
62112   474 -SLGRTVDLG-LTGNHGVVHPSLAdsankfeentycfgrtvetlllrfGK 521 taeqirdeiertneaiiqatggatptlfRpPYGewsetvlsasaklGlta
              t  +++   + r+++++i+++g   t++l R+       s+s ++Gl+
62112   522 TIMEEQLVLKRVANILINLYG-MTAVLSRA---------SRSIRIGLRN 560 vlWdvDprDWsvragadaivdavlqaa<-*
              +     D v  ++   v a+lq+
62112   561 H-------DHEVLLANTFCVEAYLQNL    580
```

Fig. 2D

62112, A NOVEL HUMAN DEHYDROGENASE AND USES THEREOF

RELATED APPLICATIONS

This application claims priority to U.S. Provisional Patent Application No. 60/229,831 entitled "62112, A NOVEL HUMAN DEHYDROGENASE AND USES THEREOF", filed on Aug. 31, 2000. The contents of the above-referenced patent application are incorporated herein in their entirety by reference.

BACKGROUND OF THE INVENTION

The oxidation and reduction of molecules is of critical importance in most metabolic and catabolic pathways in cells. A large family of enzymes which facilitate these molecular alterations, termed dehydrogenases, have been identified. In the forward reaction, these enzymes catalyze the transfer of a hydride ion from the target substrate to the enzyme or a cofactor of the enzyme (e.g., $NAD^+$ or $NADP^+$), thereby forming a carbonyl group on the substrate. These enzymes are also able to participate in the reverse reaction, wherein a carbonyl group on the target molecule is reduced by the transfer of a hydride group from the enzyme. Members of the dehydrogenase family are found in nearly all organisms, from microbes to Drosophila to humans. Both between species and within the same species, dehydrogenases vary widely, and structural similarities between distant dehydrogenase family members are most frequently found in the cofactor binding site of the enzyme. Even within a particular subclass of dehydrogenase molecules, e.g., the short-chain dehydrogenase molecules, members typically display only 15–30% amino acid sequence identity, and this is limited to the cofactor binding site and the catalytic site (Jornvall et al. (1995) Biochemistry 34:6003–6013).

Different classes of dehydrogenases are specific for an array of biological and chemical substrates. For example, there exist dehydrogenases which are specific for alcohols, for aldehydes, for steroids, and for lipids, with particularly important classes of dehydrogenases including the short-chain dehydrogenase/reductases, the medium-chain dehydrogenases, the aldehyde dehydrogenases, the alcohol dehydrogenases, the acyl-Co-A dehdrogenases, and the steroid dehydrogenases. Within each of these classes, each enzyme is specific for a particular substrate (e.g., ethanol or isopropanol, but not both with equivalent affinity). This exquisite specificity permits tight regulation of the metabolic and catabolic pathways in which these enzymes participate, without affecting similar but separate biochemical pathways in the same cell or tissue. The short-chain dehydrogenases, part of the alcohol oxidoreductase superfamily (Reid et al. (1994) Crit. Rev. Microbiol. 20:13–56), are $Zn^{++}$-independent enzymes with an N-terminal cofactor binding site and a C-terminal catalytic domain (Persson et al. (1995) Adv. Exp. Med. Biol. 372:383–395; Jornvall et al. (1995) supra), whereas the medium chain dehydrogenases are $Zn^{++}$-dependent enzymes with an N-terminal catalytic domain and a C-terminal coenzyme binding domain (Jornvall et al. (1995) supra; Jornvall et al. (1999) FEBS Lett. 445:261–264). The steroid dehydrogenases are a subclass of the short-chain dehydrogenases, and are known to be involved in a variety of biochemical pathways, affecting mammalian reproduction, hypertension, neoplasia, and digestion (Duax et al. (2000) Vitamins and Hormones 58:121–148). Aldehyde dehydrogenases show heterogeneity in the placement of these domains, and also heterogeneity in their substrates, which include toxic substances, retinoic acid, betaine, biogenic amines, and neurotransmitters (Hsu et al. (1997) Gene 189:89–94). It is common in higher organisms for different dehydrogenase molecules to be expressed in different tissues, according to the localization of the substrate for which the enzyme is specific. For example, different mammalian aldehyde dehydrogenases are localized to different tissues, e.g., salivary gland, stomach, and kidney (Hsu et al. (1999) supra).

Dehydrogenases play important roles in the production and breakdown of nearly all major metabolic intermediates, including amino acids, fatty acids, vitamins, energy molecules (e.g., glucose, sucrose, and their breakdown products), signaling molecules (e.g., transcription factors and neurotransmitters), and nucleic acids. As such, their activity contributes to the ability of the cell to grow and differentiate, to proliferate, and to communicate and interact with other cells. Dehydrogenases also are important in the detoxification of compounds to which the organism is exposed, such as alcohols, toxins, carcinogens, and mutagens.

SUMMARY OF THE INVENTION

The present invention is based, at least in part, on the discovery of a novel dehydrogenase family member, referred to herein as "dehydrogenase-7" or "DHDR-7" nucleic acid and polypeptide molecules. The DHDR-7 nucleic acid and polypeptide molecules of the present invention are useful as modulating agents in regulating a variety of cellular processes, e.g., cellular proliferation, growth, differentiation, or migration. Accordingly, in one aspect, this invention provides isolated nucleic acid molecules encoding DHDR-7 polypeptides or biologically active portions thereof, as well as nucleic acid fragments suitable as primers or hybridization probes for the detection of DHDR-7-encoding nucleic acids. The present invention is also based, at least in part, on the discovery that the novel DHDR-7 molecules of the present invention are differentially expressed in tumor cells, e.g., colon, breast, lung, or ovarian tumor cells, as compared to normal cells, e.g., normal colon, breast, lung, or ovarian cells, and, accordingly, are useful in the diagnosis and treatment of cellular growth and proliferation disorders, e.g., cancer, including, but not limited to, colon, breast, lung, or ovarian cancer.

In one embodiment, the invention features an isolated nucleic acid molecule that includes the nucleotide sequence set forth in SEQ ID NO: 1 or SEQ ID NO:3. In another embodiment, the invention features an isolated nucleic acid molecule that encodes a polypeptide including the amino acid sequence set forth in SEQ ID NO:2. In another embodiment, the invention features an isolated nucleic acid molecule that includes the nucleotide sequence contained in the plasmid deposited with ATCC® as Accession Number PTA-3439.

In still other embodiments, the invention features isolated nucleic acid molecules including nucleotide sequences that are substantially identical (e.g., 60% identical) to the nucleotide sequence set forth as SEQ ID NO:1 or SEQ ID NO:3. The invention further features isolated nucleic acid molecules including at least 50 contiguous nucleotides of the nucleotide sequence set forth as SEQ ID NO:1 or SEQ ID NO:3. In another embodiment, the invention features isolated nucleic acid molecules which encode a polypeptide including an amino acid sequence that is substantially identical (e.g., 60% identical) to the amino acid sequence set forth as SEQ ID NO:2. The present invention also features nucleic acid molecules which encode allelic variants of the polypeptide having the amino acid sequence set forth as SEQ ID NO:2. In addition to isolated nucleic acid molecules encoding full-length polypeptides, the present invention also features nucleic acid molecules which encode fragments, for example, biologically active or antigenic fragments, of the full-length polypeptides of the present invention (e.g., fragments including at least 10 contiguous amino acid residues of the amino acid sequence of SEQ ID NO:2). In still other embodiments, the invention features nucleic acid molecules that are complementary to, antisense to, or hybridize under stringent conditions to the isolated nucleic acid molecules described herein.

In another aspect, the invention provides vectors including the isolated nucleic acid molecules described herein (e.g., DHDR-7-encoding nucleic acid molecules). Such vectors can optionally include nucleotide sequences encoding heterologous polypeptides. Also featured are host cells including such vectors (e.g., host cells including vectors suitable for producing DHDR-7 nucleic acid molecules and polypeptides).

In another aspect, the invention features isolated DHDR-7 polypeptides and/or biologically active or antigenic fragments thereof. Exemplary embodiments feature a polypeptide including the amino acid sequence set forth as SEQ ID NO:2, a polypeptide including an amino acid sequence at least 60% identical to the amino acid sequence set forth as SEQ ID NO:2, a polypeptide encoded by a nucleic acid molecule including a nucleotide sequence at least 60% identical to the nucleotide sequence set forth as SEQ ID NO:1 or SEQ ID NO:3. Also featured are fragments of the full-length polypeptides described herein (e.g., fragments including at least 10 contiguous amino acid residues of the sequence set forth as SEQ ID NO:2) as well as allelic variants of the polypeptide having the amino acid sequence set forth as SEQ ID NO:2.

The DHDR-7 polypeptides and/or biologically active or antigenic fragments thereof, are useful, for example, as reagents or targets in assays applicable to treatment and/or diagnosis of DHDR-7 mediated or related disorders, e.g., dehydrogenase-associated disorders, such as cancer. In one embodiment, a DHDR-7 polypeptide or fragment thereof, has a DHDR-7 activity. In another embodiment, a DHDR-7 polypeptide or fragment thereof, has an acyl-CoA dehydrogenase domain, and optionally, has a DHDR-7 activity. In a related aspect, the invention features antibodies (e.g., antibodies which specifically bind to any one of the polypeptides described herein) as well as fusion polypeptides including all or a fragment of a polypeptide described herein.

The present invention further features methods for detecting DHDR-7 polypeptides and/or DHDR-7 nucleic acid molecules, such methods featuring, for example, a probe, primer or antibody described herein. Also featured are kits e.g., kits for the detection of DHDR-7 polypeptides and/or DHDR-7 nucleic acid molecules. In a related aspect, the invention features methods for identifying compounds which bind to and/or modulate the activity of a DHDR-7 polypeptide or DHDR-7 nucleic acid molecule described herein. Further featured are methods for modulating a DHDR-7 activity.

The present invention also provides diagnostic assays for identifying the presence or absence of a genetic alteration characterized by at least one of (i) aberrant modification or mutation of a gene encoding a DHDR-7 protein; (ii) misregulation of the gene; and (iii) aberrant post-translational modification of a DHDR-7 protein, wherein a wild-type form of the gene encodes a protein with a DHDR-7 activity.

In another aspect, the invention provides a method for identifying a compound which binds to a DHDR-7 polypeptide by contacting the polypeptide, or a cell expressing the polypeptide with a test compound, and determining whether the polypeptide binds to the test compound. In yet another aspect, the invention provides a method for identifying a compound which modulates the activity of a DHDR-7 polypeptide comprising contacting a DHDR-7 polypeptide with a test compound and determining the effect of the test compound on the activity of the polypeptide.

In another aspect, the invention provides a method for identifying the presence of a nucleic acid molecule associated with a cellular growth or proliferation disorder, in a sample, by contacting a sample comprising nucleic acid molecules with a hybridization probe comprising at least 25 contiguous nucleotides of SEQ ID NO:1 or 3, and detecting the presence of a nucleic acid molecule associated with a cellular growth or proliferation disorder, when the sample contains a nucleic acid molecule that hybridizes to the nucleic acid probe. In one embodiment, the hybridization probe is detectably labeled. In another embodiment the sample comprising nucleic acid molecules is subjected to agarose gel electrophoresis and southern blotting prior to contacting with the hybridization probe. In a further embodiment, the sample comprising nucleic acid molecules is subjected to agarose gel electrophoresis and northern blotting prior to contacting with the hybridization probe. In yet another embodiment, the detecting is by in situ hybridization. In other embodiments, the method is used to detect mRNA or genomic DNA in the sample.

The invention also provides a method for identifying a nucleic acid molecule associated with a cellular growth or proliferation disorder, in a sample, e.g., a colon, breast, ovary, or lung tissue sample, by contacting a sample comprising nucleic acid molecules with a first and a second amplification primer, the first primer comprising at least 25 contiguous nucleotides of SEQ ID NO:1 or 3 and the second primer comprising at least 25 contiguous nucleotides from the complement of SEQ ID NO:1 or 3, incubating the sample under conditions that allow for nucleic acid amplification, and detecting the presence of a nucleic acid molecule associated with a cellular growth or proliferation disorder, when the sample contains a nucleic acid molecule that is amplified. In one embodiment, the sample comprising nucleic acid molecules is subjected to agarose gel electrophoresis after the incubation step.

In addition, the invention provides a method for identifying a polypeptide associated with a cellular growth or proliferation disorder, in a sample, by contacting a sample comprising polypeptide molecules with a binding substance specific for a DHDR-7 polypeptide, and detecting the presence of a polypeptide associated with a cellular growth or proliferation disorder, when the sample contains a polypeptide molecule that binds to the binding substance. The binding substance may be an antibody or a DHDR-7 ligand, and may be detectably labeled.

In another aspect, the invention provides a method of identifying a subject at risk for a cellular growth or proliferation disorder. The method includes contacting a sample obtained from the subject comprising nucleic acid molecules with a hybridization probe comprising at least 25 contiguous nucleotides of SEQ ID NO:1 or 3, and detecting the presence of a nucleic acid molecule which identifies a subject a risk for a cellular growth or proliferation disorder, when the sample contains a nucleic acid molecule that hybridizes to the nucleic acid probe.

In a further aspect, the invention provides a method for identifying a subject at risk for a cellular growth or proliferation disorder, by contacting a sample obtained from a subject comprising nucleic acid molecules with a first and a second amplification primer, the first primer comprising at least 25 contiguous nucleotides of SEQ ID NO:1 or 3 and the second primer comprising at least 25 contiguous nucleotides from the complement of SEQ ID NO:1 or 3, incubating the sample under conditions that allow for nucleic acid amplification, and detecting a nucleic acid molecule which identifies a subject at risk for a cellular growth or proliferation disorder, when the sample contains a nucleic acid molecule that is amplified.

In yet another aspect, the invention provides a method of identifying a subject at risk for a cellular growth or proliferation disorder by contacting a sample obtained from the subject comprising polypeptide molecules with a binding substance specific for a DHDR-7 polypeptide, and detecting the presence of a polypeptide molecule in the sample that binds to the binding substance.

In another aspect, the invention provides a method for identifying a compound capable of treating a cellular growth or proliferation disorder such as cancer, e.g., colon cancer, breast cancer, lung cancer, or ovarian cancer, characterized by aberrant DHDR-7 nucleic acid expression or DHDR-7 protein activity. The method includes assaying the ability of the compound to modulate the expression of a DHDR-7 nucleic acid or the activity of a DHDR-7 protein.

Other features and advantages of the invention will be apparent from the following detailed description and claims.

BRIEF DESCRIPTION OF THE DRAWINGS

FIGS. 1A–B depicts the cDNA sequence and predicted amino acid sequence of human DHDR-7. The nucleotide sequence corresponds to nucleic acids 1 to 2452 of SEQ ID NO:1. The amino acid sequence corresponds to amino acids 1 to 621 of SEQ ID NO: 2. The coding region without the 5' or 3' untranslated region of the human DHDR-7 gene is shown in SEQ ID NO: 3.

FIGS. 2A–D depicts the results of a search which was performed against the HMM database in PFAM. The search resulted in the identification of a potential acyl-CoA dehydrogenase C-terminal domain in the amino acid sequence of human DHDR-7 at about residues 179–286 of SEQ ID NO:2, a potential acyl-CoA dehydrogenase middle domain in the amino acid sequence of human DHDR-7 at about residues 85–177 of SEQ ID NO:2, and a potential acyl-CoA dehydrogenase N-terminal domain in the amino acid sequence of human DHDR-7 at about residues 290–441 of SEQ ID NO:2, and a potential acyl-CoA dehydrogenase domain in the amino acid sequence of human DHDR-7 at about residues 85–438 of SEQ ID NO:2.

DETAILED DESCRIPTION OF THE INVENTION

Figure 3A:
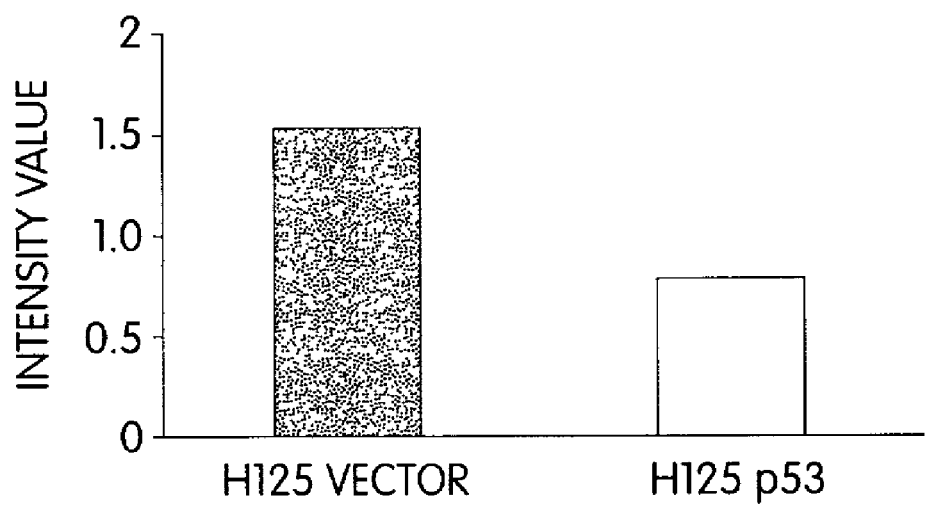
FIG. 3A is a graph showing reduced expression of DHDR-7 in NCI-H125 lung tumor cells expressing the p53 tumor suppressor gene (H125 p53) as compared to a vector only control (H125 vector), as determined by transcriptional profiling analysis.

The present invention is based, at least in part, on the discovery of novel molecules, referred to herein as "dehydrogenase-7" or "DHDR-7" nucleic acid and polypeptide molecules, which are novel members of a family of enzymes possessing dehydrogenase activity. These novel molecules are capable of oxidizing or reducing biological molecules by catalyzing the transfer of a hydride ion from the target substrate to the dehydrogenase or a cofactor of the dehydrogenase, and, thus, play a role in or function in a variety of cellular processes, e.g., proliferation, growth, differentiation, migration, metabolism, immune responses, hormonal responses, and inter- or intra-cellular communication.

The novel DHDR-7 molecules of the present invention are differentially expressed in tumor cells, e.g., colon, breast, lung, and ovarian tumor cells, as compared to normal cells, e.g., normal colon, breast, lung, and ovarian cells.

The novel DHDR-7 molecules of the present invention are acyl-CoA dehydrogenases, which are mitochondrial flavoproteins that catalyze the alpha, beta-dehydrogenation of acyl-CoA esters and reduce an electron-transferring flavoprotein. This is the first step of the beta-oxidation cycle for fatty acids, which is a critical source of energy for the cell. Rapidly growing and dividing tumor cells have increased energy requirements. Increased expression of DHDR-7 in tumor cells contributes to increased energy production, and increased energy production contributes to cellular growth and proliferation, thereby increasing tumorigenesis and metastasis of tumor cells, e.g., colon tumor cells, breast cancer tumor cells, lung tumor cells, and ovarian tumor cells. Accordingly, the DHDR-7 molecules of the present invention provide novel diagnostic targets and therapeutic agents to control cellular growth or proliferation disorders, e.g., cancer, including, but not limited to, colon cancer, breast cancer, lung cancer, and ovarian cancer.

"Differential expression", as used herein, includes both quantitative as well as qualitative differences in the temporal and/or tissue expression pattern of a gene. Thus, a differentially expressed gene may have its expression activated or inactivated in normal versus cellular growth or proliferation disease states. The degree to which expression differs in normal versus cellular growth or proliferation disease states or control versus experimental states need only be large enough to be visualized via standard characterization techniques, e.g., quantitative PCR, Northern analysis, or subtractive hybridization. The expression pattern of a differentially expressed gene may be used as part of a prognostic or diagnostic cellular growth or proliferation disorder evaluation, or may be used in methods for identifying compounds useful for the treatment of cellular growth or proliferation disorder. In addition, a differentially expressed gene involved in tumorigenic disorders may represent a target gene such that modulation of the expression level of this gene or the activity of the gene product may act to ameliorate a cellular growth or proliferation disorder. Compounds that modulate target gene expression or activity of the target gene product can be used in the treatment of cellular growth or proliferation disorders. Although the DHDR-7 genes described herein may be differentially expressed with respect to cellular growth or proliferation disorders, and/or their products may interact with gene products important to cellular growth or proliferation disorders, the genes may also be involved in mechanisms important to additional tumor cell processes.

As used herein, the term "dehydrogenase" includes a molecule which is involved in the oxidation or reduction of a biochemical molecule (e.g., an amino acid, a vitamin, or a nucleic acid), by catalyzing the transfer of a hydride ion to or from the biochemical molecule. Dehydrogenase molecules are involved in the metabolism and catabolism of biochemical molecules necessary for energy production or storage, for intra- or inter-cellular signaling, for metabolism or catabolism of metabolically important biomolecules, and for detoxification of potentially harmful compounds. Examples of dehydrogenases include alcohol dehydrogenases, aldehyde dehydrogenases, steroid dehydrogenases, and acyl-CoA dehydrogenases. Thus, the DHDR-7 molecules of the present invention provide novel diagnostic targets and therapeutic agents for dehydrogenase-associated disorders, e.g. cancer.

As used herein, a "dehydrogenase-associated disorder" includes a disorder, disease or condition which is caused or characterized by a misregulation (e.g., downregulation or upregulation) of dehydrogenase activity. Dehydrogenase-associated disorders can detrimentally affect cellular functions such as cellular proliferation, growth, differentiation, or migration, inter- or intra-cellular communication; metabolic activity; tissue function, such as cardiac function or musculoskeletal function; systemic responses in an organism, such as nervous system responses, hormonal responses (e.g., insulin response), or immune responses; and protection of cells from toxic compounds (e.g., carcinogens, toxins, or mutagens). Examples of dehydrogenase-associated disorders include CNS disorders such as cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of dehydrogenase-associated disorders include cardiac-related disorders. Cardiovascular system disorders in which the DHDR-7 molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, Jervell syndrome, Lange-Nielsen syndrome, long-QT syndrome, congestive heart failure, sinus node dysfunction, angina, heart failure, hypertension, atrial fibrillation, atrial flutter, cardiomyopathy, e.g., dilated cardiomyopathy and idiopathic cardiomyopathy, myocardial infarction, coronary artery disease, coronary artery spasm, and arrhythmia. DHDR-7-mediated or related disorders also include disorders of the musculoskeletal system such as paralysis and muscle weakness, e.g., ataxia, myotonia, and myokymia.

Dehydrogenase-associated disorders also include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells, or by which a cell moves closer to or further from a particular location or stimulus. The DHDR-7 molecules of the present invention are involved in dehydrogenation mechanisms, which are known to be involved in cellular growth, differentiation, and migration processes. Thus, the DHDR-7 molecules may modulate cellular growth, differentiation, or migration, and may play a role in disorders characterized by aberrantly regulated growth, differentiation, or migration. Such disorders include cancer, e.g., carcinoma, sarcoma, or leukemia; tumor angiogenesis and metastasis; skeletal dysplasia; hepatic disorders; and hematopoietic and/or myeloproliferative disorders. As used herein, a "tumor" includes a normal benign or malignant mass of tissue. Examples of cellular growth or proliferation disorders include, but are not limited to, cancer, e.g., carcinoma, sarcoma, or leukemia, examples of which include, but are not limited to, colon, ovarian, lung, breast, endometrial, uterine, hepatic, gastrointestinal, prostate, and brain cancer; tumorigenesis and metastasis; skeletal dysplasia; and hematopoietic and/or myeloproliferative disorders.

Dehydrogenase-associated disorders also include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

Dehydrogenase-associated disorders also include immune disorders, such as autoimmune disorders or immune deficiency disorders, e.g., congenital X-linked infantile hypogammaglobulinemia, transient hypogammaglobulinemia, common variable immunodeficiency, selective IgA deficiency, chronic mucocutaneous candidiasis, or severe combined immunodeficiency.

Dehydrogenase-associated disorders also include hepatic disease or dysfunction and metabolic disorders, such as hypoketotic or nonketotic hypoglycemia.

Dehydrogenase-associated disorders also include disorders affecting tissues in which DHDR-7 protein is expressed.

As used herein, a "dehydrogenase-mediated activity" includes an activity which involves the oxidation or reduction of one or more biochemical molecules, e.g., biochemical molecules in a tumor cell, a neuronal cell, a muscle cell, or a liver cell, associated with the regulation of one or more cellular processes. Dehydrogenase-mediated activities include the oxidation or reduction of biochemical molecules necessary for energy production or storage, for intra- or inter-cellular signaling, for metabolism or catabolism of metabolically important biomolecules, and for detoxification of potentially harmful compounds.

The term "family" when referring to the polypeptide and nucleic acid molecules of the invention is intended to mean two or more polypeptides or nucleic acid molecules having a common structural domain or motif and having sufficient amino acid or nucleotide sequence homology as defined herein. Such family members can be naturally or non-naturally occurring and can be from either the same or different species. For example, a family can contain a first polypeptide of human origin, as well as other, distinct polypeptides of human origin or alternatively, can contain homologues of non-human origin, e.g., monkey polypeptides. Members of a family may also have common functional characteristics.

For example, the family of DHDR-7 polypeptides disclosed herein comprise at least one "acyl-Co-A dehydrogenase domain." As used herein, the term "acyl-Co-A dehydrogenase domain" includes a protein domain having an amino acid sequence of about 250–450 amino acid residues, having a bit score of at least 100 when compared against an acyl-CoA dehydrogenase domain Hidden Marker Model (HMM), and which serves to catalyze the dehydrogenation of acyl-CoA esters. Preferably, an acyl-Co-A dehydrogenase domain includes at least about 353 amino acid residues and has a bit score of 399.8. To identify the presence of an acyl-Co-A dehydrogenase domain in a DHDR-7 protein, and make the determination that a protein of interest has a particular profile, the amino acid sequence of the protein may be searched against a database of known protein domains (e.g., the HMM database). In one embodiment, an acyl-Co-A dehydrogenase domain, as defined herein, may comprise an acyl-Co-A dehydrogenase middle domain, an acyl-Co-A dehydrogenase C-terminal domain, and/or an acyl-Co-A dehydrogenase N-terminal domain. A search was performed against the HMM database resulting in the identification of a potential acyl-CoA dehydrogenase C-terminal domain in the amino acid sequence of human DHDR-7 at about residues 179–286 of SEQ ID NO:2, a potential acyl-CoA dehydrogenase middle domain in the amino acid sequence of human DHDR-7 at about residues 85–177 of SEQ ID NO:2, and a potential acyl-CoA dehydrogenase N-terminal domain in the amino acid sequence of human DHDR-7 at about residues 290–441 of SEQ II) NO:2. The acyl-CoA dehydrogenase C-terminal domain (HMM) has been assigned the PFAM Accession PF00441, the acyl-CoA dehydrogenase middle domain (HMM) has been assigned the PFAM Accession PF02770, and the acyl-CoA dehydrogenase N-terminal domain (HMM) has been assigned the PFAM Accession PF02771. The results of the search are set forth in FIG. 2.

A description of the Pfam database can be found in Sonhammer et al. (1997) *Proteins* 28:405–420 and a detailed description of HMMs can be found, for example, in Gribskov et al.(1990) *Meth. Enzymol.* 183:146–159; Gribskov et al.(1987) *Proc. Natl. Acad. Sci. USA* 84:4355–4358; Krogh et al.(1994) *J. Mol. Biol.* 235:1501–1531; and Stultz et al. (1993) *Protein Sci.* 2:305–314, the contents of which are incorporated herein by reference.

Isolated polypeptides of the present invention, preferably DHDR-7 polypeptides, have an amino acid sequence sufficiently identical to the amino acid sequence of SEQ ID NO:2 or are encoded by a nucleotide sequence sufficiently identical to SEQ ID NO:1 or 3. As used herein, the term "sufficiently identical" refers to a first amino acid or nucleotide sequence which contains a sufficient or minimum number of identical or equivalent (e.g, an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 90%, 95%, 96%, 97%, 98%, 99% or more homology or identity across the amino acid sequences of the domains and contain at least one and preferably two structural domains or motifs, are defined herein as sufficiently identical. Furthermore, amino acid or nucleotide sequences which share at least 50%, 55%, 60%, 65%, 70%, 75%, 80%, 85%, 85%, 90%, 95%, 96%, 97%, 98%, 99% or more homology or identity and share a common functional activity are defined herein as sufficiently identical.

In a preferred embodiment, a DHDR-7 polypeptide includes at least one acyl-Co-A dehydrogenase domain and has an amino acid sequence at least about 50%, 55%, 60%, 65%, 70%, 75%, 80%, 85%, 85%, 90%, 95%, 96%, 97%, 98%, 99% or more homologous or identical to the amino acid sequence of SEQ ID NO:2, or the amino acid sequence encoded by the DNA insert of the plasmid deposited with ATCC as Accession Number PTA-3439. In yet another preferred embodiment, a DHDR-7 polypeptide includes at least one or more acyl-Co-A dehydrogenase domains, and is encoded by a nucleic acid molecule having a nucleotide sequence which hybridizes under stringent hybridization conditions to a complement of a nucleic acid molecule comprising the nucleotide sequence of SEQ ID NO:1 or SEQ ID NO:3. In another preferred embodiment, a DHDR-7 polypeptide includes at least one or more acyl-Co-A dehydrogenase domains, and has a DHDR-7 activity.

As used interchangeably herein, a "DHDR-7 activity", "biological activity of DHDR-7" or "functional activity of DHDR-7", includes to an activity exerted by a DHDR-7 polypeptide or nucleic acid molecule on a DHDR-7 responsive cell or tissue, or on a DHDR-7 polypeptide substrate, as determined in vivo or in vitro, according to standard techniques. In one embodiment, a DHDR-7 activity is a direct activity, such as an association with a DHDR-7-target molecule. As used herein, a "substrate," "target molecule," or "binding partner" is a molecule with which a DHDR-7 polypeptide binds or interacts in nature, such that DHDR-7-mediated function is achieved. A DHDR-7 target molecule can be a non-DHDR-7 molecule or a DHDR-7 polypeptide of the present invention. In an exemplary embodiment, a DHDR-7 target molecule is a DHDR-7 ligand, e.g., an acyl-CoA ester. Moreover, a DHDR-7 activity is an indirect activity, such as a cellular signaling activity mediated by interaction of the DHDR-7 polypeptide with a DHDR-7 ligand. The biological activities of DHDR-7 are described herein. For example, the DHDR-7 polypeptides of the present invention can have one or more of the following activities: 1) they may modulate metabolism and catabolism of biochemical molecules necessary for energy production or storage, 2) they may modulate intra- or inter-cellular signaling, 3) they may modulate metabolism or catabolism of metabolically important biomolecules, 4) they may modulate the dehydrogenation of acyl-CoA esters, 5) they may modulate detoxification of potentially harmful compounds, 6) they may modulate the beta oxidation cycle for fatty acids, and 7) they may modulate energy production in the cell.

The nucleotide sequence of the isolated human DHDR-7 cDNA and the predicted amino acid sequence of the human DHDR-7 polypeptide are shown in FIG. 1 and in SEQ ID NOs:1 and 2, respectively. A plasmid containing the nucleotide sequence encoding human DHDR-7 was deposited with the American Type Culture Collection (ATCC), 10801 University Boulevard, Manassas, Va. 20110-2209, on Jun. 7, 2001 and assigned Accession Number PTA-3439. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The human DHDR-7 gene, which is approximately 2452 nucleotides in length, encodes a polypeptide which is approximately 621 amino acid residues in length.

Various aspects of the invention are described in further detail in the following subsections:

I. Isolated Nucleic Acid Molecules

One aspect of the invention pertains to isolated nucleic acid molecules that encode DHDR-7 polypeptides or biologically active portions thereof, as well as nucleic acid fragments sufficient for use as hybridization probes to identify DHDR-7-encoding nucleic acid molecules (e.g., DHDR-7 mRNA) and fragments for use as PCR primers for the amplification or mutation of DHDR-7 nucleic acid molecules. As used herein, the term "nucleic acid molecule" is intended to include DNA molecules (e.g., cDNA or genomic DNA) and RNA molecules (e.g, mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated DHDR-7 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 3, or the nucleotide sequence of the DNA insert of the plasmid deposited with ATCC as Accession Number PTA-3439, or a portion thereof, can be isolated using standard molecular biology techniques and the sequence information provided herein. Using all or a portion of the nucleic acid sequence of SEQ ID NO:1 or 3, or the nucleotide sequence of the DNA insert of the plasmid deposited with ATCC as Accession Number PTA-3439, as a hybridization probe, DHDR-7 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1 or 3, or the nucleotide sequence of the DNA insert of the plasmid deposited with ATCC as Accession Number PTA-3439 can be isolated by the polymerase chain reaction (PCR) using synthetic oligonucleotide primers designed based upon the sequence of SEQ ID NO:1 or 3, or the nucleotide sequence of the DNA insert of the plasmid deposited with ATCC as Accession Number PTA-3439.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to DHDR-7 nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:1 or 3. This cDNA may comprise sequences encoding the human DHDR-7 protein (e.g., the "coding region", from nucleotides 67–1932), as well as 5' untranslated sequence (nucleotides 1–66) and 3' untranslated sequences (nucleotides 1933–2452) of SEQ ID NO:1. Alternatively, the nucleic acid molecule can comprise only the coding region of SEQ ID NO:1 (e.g., nucleotides 67–1932, corresponding to SEQ ID NO:3). Accordingly, in another embodiment, an isolated nucleic acid molecule of the invention comprises SEQ ID NO:3 and nucleotides 1–66 of SEQ ID NO:1. In yet another embodiment, the isolated nucleic acid molecule comprises SEQ ID NO:3 and nucleotides 1933–2452 of SEQ ID NO:1. In yet another embodiment, the nucleic acid molecule consists of the nucleotide sequence set forth as SEQ ID NO:1 or SEQ ID NO:3.

Accordingly, in another embodiment, the isolated nucleic acid molecule comprises SEQ ID NO:3 and nucleotides 1–66 and 1933–2452 of SEQ ID NO:1. In yet another embodiment, the nucleic acid molecule consists of the nucleotide sequence set forth as SEQ ID NO:1 or SEQ ID NO:3.

In still another embodiment, an isolated nucleic acid molecule of the invention comprises a nucleic acid molecule which is a complement of the nucleotide sequence shown in SEQ ID NO:1 or 3, or the nucleotide sequence of the DNA insert of the plasmid deposited with ATCC as Accession Number PTA-3439, or a portion of any of these nucleotide sequences. A nucleic acid molecule which is complementary to the nucleotide sequence shown in SEQ ID NO:1 or 3, or the nucleotide sequence of the DNA insert of the plasmid deposited with ATCC as Accession Number PTA-3439, is one which is sufficiently complementary to the nucleotide sequence shown in SEQ ID NO:1 or 3, or the nucleotide sequence of the DNA insert of the plasmid deposited with ATCC as Accession Number PTA-3439, such that it can hybridize to the nucleotide sequence shown in SEQ ID NO:1 or 3, or the nucleotide sequence of the DNA insert of the plasmid deposited with ATCC as Accession Number PTA-3439, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99% or more identical to the nucleotide sequence shown in SEQ ID NO:1 or 3 (e.g., to the entire length of the nucleotide sequence), or to the nucleotide sequence (e.g., the entire length of the nucleotide sequence) of the DNA insert of the plasmid deposited with ATCC as Accession Number PTA-3439, or a portion of any of these nucleotide sequences. In one embodiment, a nucleic acid molecule of the present invention comprises a nucleotide sequence which is at least (or no greater than) 50–100, 100–250, 250–500, 500–750, 750–1000, 1000–1250, 1250–1500, 1500–1750, 1750–2000, 2000–2250, 2250–2500 or more nucleotides in length and hybridizes under stringent hybridization conditions to a complement of a nucleic acid molecule of SEQ ID NO:1 or 3, or the nucleotide sequence of the DNA insert of the plasmid deposited with ATCC as Accession Number PTA-3439.

Moreover, the nucleic acid molecule of the invention can comprise only a portion of the nucleic acid sequence of SEQ ID NO:1 or 3, or the nucleotide sequence of the DNA insert of the plasmid deposited with ATCC as Accession Number PTA-3439, for example, a fragment which can be used as a probe or primer or a fragment encoding a portion of a DHDR-7 polypeptide, e.g., a biologically active portion of a DHDR-7 polypeptide. The nucleotide sequence determined from the cloning of the DHDR-7 gene allows for the generation of probes and primers designed for use in identifying and/or cloning other DHDR-7 family members, as well as DHDR-7 homologues from other species. The probe/primer typically comprises substantially purified oligonucleotide. The probe/primer (e.g., oligonucleotide) typically comprises a region of nucleotide sequence that hybridizes under stringent conditions to at least about 12 or 15, preferably about 20 or 25, more preferably about 30, 35, 40, 45, 50, 55, 60, 65, 75, 80, 85, 90, 95, or 100 or more consecutive nucleotides of a sense sequence of SEQ ID NO:1 or 3, or the nucleotide sequence of the DNA insert of the plasmid deposited with ATCC as Accession Number PTA-3439, of an anti-sense sequence of SEQ ID NO:1 or 3, or the nucleotide sequence of the DNA insert of the plasmid deposited with ATCC as Accession Number PTA-3439, or of a naturally occurring allelic variant or mutant of SEQ ID NO:1 or 3, or the nucleotide sequence of the DNA insert of the plasmid deposited with ATCC as Accession Number PTA-3439.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Probes based on the DHDR-7 nucleotide sequences can be used to detect (e.g., specifically detect) transcripts or genomic sequences encoding the same or homologous polypeptides. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of a DHDR-7 sequence, e.g., a domain, region, site or other sequence described herein. The primers should be at least 5, 10, or 50 base pairs in length and less than 100, or less than 200, base pairs in length. Such probes can be used as a part of a diagnostic test kit for identifying cells or tissue which misexpress a DHDR-7 polypeptide, such as by measuring a level of a DHDR-7-encoding nucleic acid in a sample of cells from a subject e.g., detecting DHDR-7 mRNA levels or determining whether a genomic DHDR-7 gene has been mutated or deleted.

A nucleic acid fragment encoding a "biologically active portion of a DHDR-7 polypeptide" can be prepared by isolating a portion of the nucleotide sequence of SEQ ID NO:1 or 3, or the nucleotide sequence of the DNA insert of the plasmid deposited with ATCC as Accession Number PTA-3439, which encodes a polypeptide having a DHDR-7 biological activity (the biological activities of the DHDR-7 polypeptides are described herein), expressing the encoded portion of the DHDR-7 polypeptide (e.g., by recombinant expression in vitro) and assessing the activity of the encoded portion of the DHDR-7 polypeptide. In an exemplary embodiment, the nucleic acid molecule is at least 50–100, 100–250, 250–500, 500–750, 750–1000, 1000–1250, 1250–1500, 1500–1750, 1750–2000, 2000–2250, 2250–2500 or more nucleotides in length and encodes a polypeptide having a DHDR-7 activity (as described herein).

The invention further encompasses nucleic acid molecules that differ from the nucleotide sequence shown in SEQ ID NO:1 or 3, or the nucleotide sequence of the DNA insert of the plasmid deposited with ATCC as Accession Number PTA-3439. Such differences can be due to the degeneracy of the genetic code, thus resulting in a nucleic acid which encodes the same DHDR-7 polypeptides as those encoded by the nucleotide sequence shown in SEQ ID NO:1 or 3, or the nucleotide sequence of the DNA insert of the plasmid deposited with ATCC as Accession Number PTA-3439. In another embodiment, an isolated nucleic acid molecule of the invention has a nucleotide sequence encoding a polypeptide having an amino acid sequence which differs by at least 1, but no greater than 5, 10, 20, 50, 100, or 200 amino acid residues from the amino acid sequence shown in SEQ ID NO:2, or the amino acid sequence encoded by the DNA insert of the plasmid deposited with the ATCC as Accession Number PTA-3439. In yet another embodiment, the nucleic acid molecule encodes the amino acid sequence of human DHDR-7. If an alignment is needed for this comparison, the sequences should be aligned for maximum homology.

Nucleic acid variants can be naturally occurring, such as allelic variants (same locus), homologues (different locus), and orthologues (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the DHDR-7 polypeptides. Such genetic polymorphism in the DHDR-7 genes may exist among individuals within a population due to natural allelic variation. As used herein, the terms "gene" and "recombinant gene" refer to nucleic acid molecules which include an open reading frame encoding a DHDR-7 polypeptide, preferably a mammalian DHDR-7 polypeptide, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:2, or an amino acid sequence encoded by the DNA insert of the plasmid deposited with ATCC as Accession Number PTA-3439, wherein the nucleic acid molecule hybridizes to a complement of a nucleic acid molecule comprising SEQ ID NO:1 or SEQ ID NO:3, for example, under stringent hybridization conditions.

Allelic variants of human DHDR-7 include both functional and non-functional DHDR-7 polypeptides. Functional allelic variants are naturally occurring amino acid sequence variants of the human DHDR-7 polypeptide that maintain the ability to bind a DHDR-7 ligand or substrate and/or modulate membrane excitability or signal transduction. Functional allelic variants will typically contain only conservative substitution of one or more amino acids of SEQ ID NO:2, or substitution, deletion or insertion of non-critical residues in non-critical regions of the polypeptide.

Non-functional allelic variants are naturally occurring amino acid sequence variants of the human DHDR-7 polypeptide that do not have the ability to form functional calcium channels or to modulate membrane excitability. Non-functional allelic variants will typically contain a non-conservative substitution, a deletion, or insertion or premature truncation of the amino acid sequence of SEQ ID NO:2, or a substitution, insertion or deletion in critical residues or critical regions.

The present invention further provides non-human and non-murine orthologues (e.g., non-human and non-murine orthologues of the human DHDR-7 polypeptide). Orthologues of the human DHDR-7 polypeptides are polypeptides that are isolated from non-human organisms and possess the same DHDR-7 ligand binding and/or modulation of membrane excitation mechanisms of the human DHDR-7 polypeptide. Orthologues of the human DHDR-7 polypeptide can readily be identified as comprising an amino acid sequence that is substantially identical to SEQ ID NO:2.

Moreover, nucleic acid molecules encoding other DHDR-7 family members and, thus, which have a nucleotide sequence which differs from the DHDR-7 sequences of SEQ ID NO:1 or 3, or the nucleotide sequence of the DNA insert of the plasmid deposited with ATCC as Accession Number PTA-3439 are intended to be within the scope of the invention. For example, another DHDR-7 cDNA can be identified based on the nucleotide sequence of human DHDR-7. Moreover, nucleic acid molecules encoding DHDR-7 polypeptides from different species, and which, thus, have a nucleotide sequence which differs from the DHDR-7 sequences of SEQ ID NO:1 or 3, or the nucleotide sequence of the DNA insert of the plasmid deposited with ATCC as Accession Number PTA-3439 are intended to be within the scope of the invention. For example, a hamster DHDR-7 cDNA can be identified based on the nucleotide sequence of a human DHDR-7.

Nucleic acid molecules corresponding to natural allelic variants and homologues of the DHDR-7 cDNAs of the invention can be isolated based on their homology to the DHDR-7 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the DHDR-7 cDNAs of the invention can further be isolated by mapping to the same chromosome or locus as the DHDR-7 gene.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3, or the nucleotide sequence of the DNA insert of the plasmid deposited with ATCC as Accession Number PTA-3439. In other embodiments, the nucleic acid is at least 50–100, 100–250, 250–500, 500–750, 750–1000, 1000–1250, 1250–1500, 1500–1750, 1750–2000, 2000–2250, 2250–2500 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6(log$_{10}$[Na$^+$])+0.41(%G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991–1995, (or alternatively 0.2×SSC, 1% SDS).

Preferably, an isolated nucleic acid molecule of the invention that hybridizes under stringent conditions to the sequence of SEQ ID NO:1 or 3 and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural polypeptide).

In addition to naturally-occurring allelic variants of the DHDR-7 sequences that may exist in the population, the skilled artisan will further appreciate that changes can be introduced by mutation into the nucleotide sequences of SEQ ID NO:1 or 3, or the nucleotide sequence of the DNA insert of the plasmid deposited with ATCC as Accession Number PTA-3439, thereby leading to changes in the amino acid sequence of the encoded DHDR-7 polypeptides, without altering the functional ability of the DHDR-7 polypeptides. For example, nucleotide substitutions leading to amino acid substitutions at "non-essential" amino acid residues can be made in the sequence of SEQ ID NO:1 or 3, or the nucleotide sequence of the DNA insert of the plasmid deposited with ATCC as Accession Number PTA-3439. A "non-essential" amino acid residue is a residue that can be altered from the wild-type sequence of DHDR-7 (e.g., the sequence of SEQ ID NO:2) without altering the biological activity, whereas an "essential" amino acid residue is required for biological activity. For example, amino acid residues that are conserved among the DHDR-7 polypeptides of the present invention, e.g., those present in an acyl-CoA dehydrogenase domain, are predicted to be particularly unamenable to alteration. Furthermore, additional amino acid residues that are conserved between the DHDR-7 polypeptides of the present invention and other members of the DHDR-7 family are not likely to be amenable to alteration.

Accordingly, another aspect of the invention pertains to nucleic acid molecules encoding DHDR-7 polypeptides that contain changes in amino acid residues that are not essential for activity. Such DHDR-7 polypeptides differ in amino acid sequence from SEQ ID NO:2, yet retain biological activity. In one embodiment, the isolated nucleic acid molecule comprises a nucleotide sequence encoding a polypeptide, wherein the polypeptide comprises an amino acid sequence at least about 50%, 55%, 60%, 65%, 70%, 75%, 80%, 85%, 90%, 95%, 96%, 97%, 98%, 99% or more identical to SEQ ID NO:2 (e.g., to the entire length of SEQ ID NO:2).

An isolated nucleic acid molecule encoding a DHDR-7 polypeptide identical to the polypeptide of SEQ ID NO:2, can be created by introducing one or more nucleotide substitutions, additions or deletions into the nucleotide sequence of SEQ ID NO:1 or 3, or the nucleotide sequence of the DNA insert of the plasmid deposited with ATCC as Accession Number PTA-3439, such that one or more amino acid substitutions, additions or deletions are introduced into the encoded polypeptide. Mutations can be introduced into SEQ ID NO:1 or 3, or the nucleotide sequence of the DNA insert of the plasmid deposited with ATCC as Accession Number PTA-3439 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a DHDR-7 polypeptide is preferably replaced with another amino acid residue from the same side chain family. Alternatively, in another embodiment, mutations can be introduced randomly along all or part of a DHDR-7 coding sequence, such as by saturation mutagenesis, and the resultant mutants can be screened for DHDR-7 biological activity to identify mutants that retain activity. Following mutagenesis of SEQ ID NO:1 or 3, or the nucleotide sequence of the DNA insert of the plasmid deposited with ATCC as Accession Number PTA-3439, the encoded polypeptide can be expressed recombinantly and the activity of the polypeptide can be determined.

In a preferred embodiment, a mutant DHDR-7 polypeptide can be assayed for the ability to: 1) modulate metabolism and catabolism of biochemical molecules necessary for energy production or storage, 2) modulate intra- or intercellular signaling, 3) modulate metabolism or catabolism of metabolically important biomolecules, 4) modulate the dehydrogenation of acyl-CoA esters, 5) modulate detoxification of potentially harmful compounds, 6) modulate the beta oxidation cycle for fatty acids, and 7) modulate energy production in the cell.

In addition to the nucleic acid molecules encoding DHDR-7 polypeptides described above, another aspect of the invention pertains to isolated nucleic acid molecules which are antisense thereto. In an exemplary embodiment, the invention provides an isolated nucleic acid molecule which is antisense to a DHDR-7 nucleic acid molecule (e.g., is antisense to the coding strand of a DHDR-7 nucleic acid molecule). An "antisense" nucleic acid comprises a nucleotide sequence which is complementary to a "sense" nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire DHDR-7 coding strand, or to only a portion thereof. In one embodiment, an antisense nucleic acid molecule is antisense to a "coding region" of the coding strand of a nucleotide sequence encoding DHDR-7. The term "coding region" refers to the region of the nucleotide sequence comprising codons which are translated into amino acid residues (e.g., the coding region of human DHDR-7 corresponds to SEQ ID NO:3). In another embodiment, the antisense nucleic acid molecule is antisense to a "noncoding region" of the coding strand of a nucleotide sequence encoding DHDR-7. The term "noncoding region" refers to 5' and 3' sequences which flank the coding region that are not translated into amino acids (i.e., also referred to as 5' and 3' untranslated regions).

Given the coding strand sequences encoding DHDR-7 disclosed herein (e.g., SEQ ID NO:3), antisense nucleic acids of the invention can be designed according to the rules of Watson and Crick base pairing. The antisense nucleic acid molecule can be complementary to the entire coding region of DHDR-7 mRNA, but more preferably is an oligonucleotide which is antisense to only a portion of the coding or noncoding region of DHDR-7 mRNA. For example, the antisense oligonucleotide can be complementary to the region surrounding the translation start site of DHDR-7 mRNA (e.g., between the −10 and +10 regions of the start site of a gene nucleotide sequence). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a DHDR-7 polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave DHDR-7 mRNA transcripts to thereby inhibit translation of DHDR-7 mRNA. A ribozyme having specificity for a DHDR-7-encoding nucleic acid can be designed based upon the nucleotide sequence of a DHDR-7 cDNA disclosed herein (i.e., SEQ ID NO:1 or 3, or the nucleotide sequence of the DNA insert of the plasmid deposited with ATCC as Accession Number PTA-3439). For example, a derivative of a *Tetrahymena* L-19 IVS RNA can be constructed in which the nucleotide sequence of the active site is complementary to the nucleotide sequence to be cleaved in a DHDR-7-encoding mRNA. See, e.g, Cech et al. U.S. Pat. No. 4,987,071; and Cech et al. U.S. Pat. No. 5,116,742. Alternatively, DHDR-7 mRNA can be used to select a catalytic RNA having a specific ribonuclease activity from a pool of RNA molecules. See, e.g., Bartel, D. and Szostak, J. W. (1993) *Science* 261:1411–1418.

Alternatively, DHDR-7 gene expression can be inhibited by targeting nucleotide sequences complementary to the regulatory region of the DHDR-7 (e.g., the DHDR-7 promoter and/or enhancers) to form triple helical structures that prevent transcription of the DHDR-7 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12): 807–15.

In yet another embodiment, the DHDR-7 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of DHDR-7 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of DHDR-7 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of DHDR-7 can be modified, (e.g, to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of DHDR-7 nucleic acid molecules can be generated which may combine the advantageous properties of PNA and DNA. Such chimeras allow DNA recognition enzymes, (e.g., RNase H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous DHDR-7 gene within a cell line or microorganism may be modified by inserting a heterologous DNA regulatory element into the genome of a stable cell line or cloned microorganism such that the inserted regulatory element is operatively linked with the endogenous DHDR-7 gene. For example, an endogenous DHDR-7 gene which is normally "transcriptionally silent", i.e., a DHDR-7 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous DHDR-7 gene may be activated by insertion of a promiscuous regulatory element that works across cell types.

A heterologous regulatory element may be inserted into a stable cell line or cloned microorganism, such that it is operatively linked with an endogenous DHDR-7 gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated DHDR-7 Polypeptides and Anti-DHDR-7 Antibodies

One aspect of the invention pertains to isolated DHDR-7 or recombinant polypeptides and polypeptides, and biologically active portions thereof, as well as polypeptide fragments suitable for use as immunogens to raise anti-DHDR-7 antibodies. In one embodiment, native DHDR-7 polypeptides can be isolated from cells or tissue sources by an appropriate purification scheme using standard protein purification techniques. In another embodiment, DHDR-7 polypeptides are produced by recombinant DNA techniques. Alternative to recombinant expression, a DHDR-7 polypeptide or polypeptide can be synthesized chemically using standard peptide synthesis techniques.

An "isolated" or "purified" polypeptide or biologically active portion thereof is substantially free of cellular material or other contaminating proteins from the cell or tissue source from which the DHDR-7 polypeptide is derived, or substantially free from chemical precursors or other chemicals when chemically synthesized. The language "substantially free of cellular material" includes preparations of DHDR-7 polypeptide in which the polypeptide is separated from cellular components of the cells from which it is isolated or recombinantly produced. In one embodiment, the language "substantially free of cellular material" includes preparations of DHDR-7 polypeptide having less than about 30% (by dry weight) of non-DHDR-7 polypeptide (also referred to herein as a "contaminating protein"), more preferably less than about 20% of non-DHDR-7 polypeptide, still more preferably less than about 10% of non-DHDR-7 polypeptide, and most preferably less than about 5% non-DHDR-7 polypeptide. When the DHDR-7 polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of DHDR-7 polypeptide in which the polypeptide is separated from chemical precursors or other chemicals which are involved in the synthesis of the polypeptide. In one embodiment, the language "substantially free of chemical precursors or other chemicals" includes preparations of DHDR-7 polypeptide having less than about 30% (by dry weight) of chemical precursors or non-DHDR-7 chemicals, more preferably less than about 20% chemical precursors or non-DHDR-7 chemicals, still more preferably less than about 10% chemical precursors or non-DHDR-7 chemicals, and most preferably less than about 5% chemical precursors or non-DHDR-7 chemicals.

As used herein, a "biologically active portion" of a DHDR-7 polypeptide includes a fragment of a DHDR-7 polypeptide which participates in an interaction between a DHDR-7 molecule and a non-DHDR-7 molecule. Biologically active portions of a DHDR-7 polypeptide include peptides comprising amino acid sequences sufficiently identical to or derived from the amino acid sequence of the DHDR-7 polypeptide, e.g., the amino acid sequence shown in SEQ ID NO:2, which include less amino acids than the full length DHDR-7 polypeptides, and exhibit at least one activity of a DHDR-7 polypeptide. Typically, biologically active portions comprise a domain or motif with at least one activity of the DHDR-7 polypeptide, e.g., modulating membrane excitation mechanisms. A biologically active portion of a DHDR-7 polypeptide can be a polypeptide which is, for example, 25, 30, 35, 40, 45, 50, 75, 100, 125, 150, 175, 200, 225, 250, 275, 300, 325, 350, 375, 400, 425, 450, 475, 500, 525, 550, 575, 600, 620 or more amino acids in length. Biologically active portions of a DHDR-7 polypeptide can be used as targets for developing agents which modulate a DHDR-7 mediated activity, e.g., metabolism or catabolism of metabolically important biomolecules, modulation of the beta oxidation cycle for fatty acids.

In one embodiment, a biologically active portion of a DHDR-7 polypeptide comprises at least one acyl-Co-A dehydrogenase domain. It is to be understood that a preferred biologically active portion of a DHDR-7 polypeptide of the present invention comprises at least one or more acyl-Co-A dehydrogenase domains. Moreover, other biologically active portions, in which other regions of the polypeptide are deleted, can be prepared by recombinant techniques and evaluated for one or more of the functional activities of a native DHDR-7 polypeptide.

Another aspect of the invention features fragments of the polypeptide having the amino acid sequence of SEQ ID NO:2, for example, for use as immunogens. In one embodiment, a fragment comprises at least 5 amino acids (e.g., contiguous or consecutive amino acids) of the amino acid sequence of SEQ ID NO:2, or an amino acid sequence encoded by the DNA insert of the plasmid deposited with the ATCC as Accession Number PTA-3439. In another embodiment, a fragment comprises at least 10, 15, 20, 25, 30, 35, 40, 45, 50 or more amino acids (e.g., contiguous or consecutive amino acids) of the amino acid sequence of SEQ ID NO:2, or an amino acid sequence encoded by the DNA insert of the plasmid deposited with the ATCC as Accession Number PTA-3439.

In a preferred embodiment, a DHDR-7 polypeptide has an amino acid sequence shown in SEQ ID NO:2. In other embodiments, the DHDR-7 polypeptide is substantially identical to SEQ ID NO:2, and retains the functional activity of the polypeptide of SEQ ID NO:2, yet differs in amino acid sequence due to natural allelic variation or mutagenesis, as described in detail in subsection I above. In another embodiment, the DHDR-7 polypeptide is a polypeptide which comprises an amino acid sequence at least about 50%, 55%, 60%, 65%, 70%, 75%, 80%, 85%, 90%, 95%, 96%, 97%, 98%, 99% or more identical to SEQ ID NO:2.

In another embodiment, the invention features a DHDR-7 polypeptide which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:1 or SEQ ID NO:3, or a complement thereof. This invention further features a DHDR-7 polypeptide which is encoded by a nucleic acid molecule consisting of a nucleotide sequence which hybridizes under stringent hybridization conditions to a complement of a nucleic acid molecule comprising the nucleotide sequence of SEQ ID NO:1 or SEQ ID NO:3, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the DHDR-7 amino acid sequence of SEQ ID NO:2 having 621 amino acid residues, at least 186, preferably at least 248, more preferably at least 310, more preferably at least 327, even more preferably at least 434, and even more preferably at least 496 or 558 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of E. Meyers and W. Miller (*Comput. Appl. Biosci.*, 4:11–17 (1988)) which has been incorporated into the ALIGN program (version 2.0 or version 2.0U), using a PAM120 weight residue table, a gap length penalty of 12 and a gap penalty of 4.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to DHDR-7 nucleic acid molecules of the invention. BLAST protein searches can be performed with the XBLAST program, score=100, wordlength=3, and a Blosum62 matrix to obtain amino acid sequences homologous to DHDR-7 polypeptide molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

The invention also provides DHDR-7 chimeric or fusion proteins. As used herein, a DHDR-7 "chimeric protein" or "fusion protein" comprises a DHDR-7 polypeptide operatively linked to a non-DHDR-7 polypeptide. A "DHDR-7 polypeptide" refers to a polypeptide having an amino acid sequence corresponding to DHDR-7, whereas a "non-DHDR-7 polypeptide" refers to a polypeptide having an amino acid sequence corresponding to a polypeptide which is not substantially homologous to the DHDR-7 polypeptide, e.g., a polypeptide which is different from the DHDR-7 polypeptide and which is derived from the same or a different organism. Within a DHDR-7 fusion protein the DHDR-7 polypeptide can correspond to all or a portion of a DHDR-7 polypeptide. In a preferred embodiment, a DHDR-7 fusion protein comprises at least one biologically active portion of a DHDR-7 polypeptide. In another preferred embodiment, a DHDR-7 fusion protein comprises at least two biologically active portions of a DHDR-7 polypeptide. Within the fusion protein, the term "operatively linked" is intended to indicate that the DHDR-7 polypeptide and the non-DHDR-7 polypeptide are fused in-frame to each other. The non-DHDR-7 polypeptide can be fused to the N-terminus or C-terminus of the DHDR-7 polypeptide.

For example, in one embodiment, the fusion protein is a GST-DHDR-7 fusion protein in which the DHDR-7 sequences are fused to the C-terminus of the GST sequences. Such fusion proteins can facilitate the purification of recombinant DHDR-7.

In another embodiment, the fusion protein is a DHDR-7 polypeptide containing a heterologous signal sequence at its N-terminus. In certain host cells (e.g., mammalian host cells), expression and/or secretion of DHDR-7 can be increased through the use of a heterologous signal sequence.

The DHDR-7 fusion proteins of the invention can be incorporated into pharmaceutical compositions and administered to a subject in vivo. The DHDR-7 fusion proteins can be used to affect the bioavailability of a DHDR-7 substrate. Use of DHDR-7 fusion proteins may be useful therapeutically for the treatment of disorders caused by, for example, (i) aberrant modification or mutation of a gene encoding a DHDR-7 polypeptide; (ii) mis-regulation of the DHDR-7 gene; and (iii) aberrant post-translational modification of a DHDR-7 polypeptide.

Moreover, the DHDR-7-fusion proteins of the invention can be used as immunogens to produce anti-DHDR-7 antibodies in a subject, to purify DHDR-7 ligands and in screening assays to identify molecules which inhibit the interaction of DHDR-7 with a DHDR-7 substrate.

Preferably, a DHDR-7 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A DHDR-7-encoding nucleic acid can be cloned into such an expression vector such that the fusion moiety is linked in-frame to the DHDR-7 polypeptide.

The present invention also pertains to variants of the DHDR-7 polypeptides which function as either DHDR-7 agonists (mimetics) or as DHDR-7 antagonists. Variants of the DHDR-7 polypeptides can be generated by mutagenesis, e.g., discrete point mutation or truncation of a DHDR-7 polypeptide. An agonist of the DHDR-7 polypeptides can retain substantially the same, or a subset, of the biological activities of the naturally occurring form of a DHDR-7 polypeptide. An antagonist of a DHDR-7 polypeptide can inhibit one or more of the activities of the naturally occurring form of the DHDR-7 polypeptide by, for example, competitively modulating a DHDR-7-mediated activity of a DHDR-7 polypeptide. Thus, specific biological effects can be elicited by treatment with a variant of limited function. In one embodiment, treatment of a subject with a variant having a subset of the biological activities of the naturally occurring form of the polypeptide has fewer side effects in a subject relative to treatment with the naturally occurring form of the DHDR-7 polypeptide.

In one embodiment, variants of a DHDR-7 polypeptide which function as either DHDR-7 agonists (mimetics) or as DHDR-7 antagonists can be identified by screening combinatorial libraries of mutants, e.g., truncation mutants, of a DHDR-7 polypeptide for DHDR-7 polypeptide agonist or antagonist activity. In one embodiment, a variegated library of DHDR-7 variants is generated by combinatorial mutagenesis at the nucleic acid level and is encoded by a variegated gene library. A variegated library of DHDR-7 variants can be produced by, for example, enzymatically ligating a mixture of synthetic oligonucleotides into gene sequences such that a degenerate set of potential DHDR-7 sequences is expressible as individual polypeptides, or alternatively, as a set of larger fusion proteins (e.g., for phage display) containing the set of DHDR-7 sequences therein. There are a variety of methods which can be used to produce libraries of potential DHDR-7 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential DHDR-7 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a DHDR-7 polypeptide coding sequence can be used to generate a variegated population of DHDR-7 fragments for screening and subsequent selection of variants of a DHDR-7 polypeptide. In one embodiment, a library of coding sequence fragments can be generated by treating a double stranded PCR fragment of a DHDR-7 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the DHDR-7 polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of DHDR-7 polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify DHDR-7 variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated DHDR-7 library. For example, a library of expression vectors can be transfected into a cell line, e.g., an endothelial cell line, which ordinarily responds to DHDR-7 in a particular DHDR-7 substrate-dependent manner. The transfected cells are then contacted with DHDR-7 and the effect of expression of the mutant on signaling by the DHDR-7 substrate can be detected, e.g., by monitoring intracellular calcium, IP3, or diacylglycerol concentration, phosphorylation profile of intracellular proteins, or the activity of a DHDR-7-regulated transcription factor. Plasmid DNA can then be recovered from the cells which score for inhibition, or alternatively, potentiation of signaling by the DHDR-7 substrate, and the individual clones further characterized.

An isolated DHDR-7 polypeptide, or a portion or fragment thereof, can be used as an immunogen to generate antibodies that bind DHDR-7 using standard techniques for polyclonal and monoclonal antibody preparation. A full-length DHDR-7 polypeptide can be used or, alternatively, the invention provides antigenic peptide fragments of DHDR-7 for use as immunogens. The antigenic peptide of DHDR-7 comprises at least 8 amino acid residues of the amino acid sequence shown in SEQ ID NO:2 and encompasses an epitope of DHDR-7 such that an antibody raised against the peptide forms a specific immune complex with DHDR-7. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of DHDR-7 that are located on the surface of the polypeptide, e.g., hydrophilic regions, as well as regions with high antigenicity (see, for example, FIG. 5).

A DHDR-7 immunogen typically is used to prepare antibodies by immunizing a suitable subject, (e.g., rabbit, goat, mouse or other mammal) with the immunogen. An appropriate immunogenic preparation can contain, for example, recombinantly expressed DHDR-7 polypeptide or a chemically synthesized DHDR-7 polypeptide. The preparation can further include an adjuvant, such as Freund's complete or incomplete adjuvant, or similar immunostimulatory agent. Immunization of a suitable subject with an immunogenic DHDR-7 preparation induces a polyclonal anti-DHDR-7 antibody response.

Accordingly, another aspect of the invention pertains to anti-DHDR-7 antibodies. The term "antibody" as used herein refers to immunoglobulin molecules and immunologically active portions of immunoglobulin molecules, i.e., molecules that contain an antigen binding site which specifically binds (immunoreacts with) an antigen, such as DHDR-7. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind DHDR-7. The term "monoclonal antibody" or "monoclonal antibody composition", as used herein, refers to a population of antibody molecules that contain only one species of an antigen binding site capable of immunoreacting with a particular epitope of DHDR-7. A monoclonal antibody composition thus typically displays a single binding affinity for a particular DHDR-7 polypeptide with which it immunoreacts.

Polyclonal anti-DHDR-7 antibodies can be prepared as described above by immunizing a suitable subject with a DHDR-7 immunogen. The anti-DHDR-7 antibody titer in the immunized subject can be monitored over time by standard techniques, such as with an enzyme linked immunosorbent assay (ELISA) using immobilized DHDR-7. If desired, the antibody molecules directed against DHDR-7 can be isolated from the mammal (e.g., from the blood) and further purified by well known techniques, such as protein A chromatography to obtain the IgG fraction. At an appropriate time after immunization, e.g., when the anti-DHDR-7 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy,* Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a DHDR-7 immunogen as described above, and the culture supernatants of the resulting hybridoma cells are screened to identify a hybridoma producing a monoclonal antibody that binds DHDR-7.

Any of the many well known protocols used for fusing lymphocytes and immortalized cell lines can be applied for the purpose of generating an anti-DHDR-7 monoclonal antibody (see, e.g., G. Galfre et al. (1977) *Nature* 266: 55052; Gefter et al. *Somatic Cell Genet.*, cited supra; Lerner, *Yale J. Biol. Med.*, cited supra; Kenneth, *Monoclonal Anti-* bodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS 1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind DHDR-7, e.g., using a standard ELISA assay.

Alternative to preparing monoclonal antibody-secreting hybridomas, a monoclonal anti-DHDR-7 antibody can be identified and isolated by screening a recombinant combinatorial immunoglobulin library (e.g., an antibody phage display library) with DHDR-7 to thereby isolate immunoglobulin library members that bind DHDR-7. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-DHDR-7 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-DHDR-7 antibody (e.g., monoclonal antibody) can be used to isolate DHDR-7 by standard techniques, such as affinity chromatography or immunoprecipitation. An anti-DHDR-7 antibody can facilitate the purification of natural DHDR-7 from cells and of recombinantly produced DHDR-7 expressed in host cells. Moreover, an anti-DHDR-7 antibody can be used to detect DHDR-7 polypeptide (e.g., in a cellular lysate or cell supernatant) in order to evaluate the abundance and pattern of expression of the DHDR-7 polypeptide. Anti-DHDR-7 antibodies can be used diagnostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, for example recombinant expression vectors, containing a nucleic acid containing a DHDR-7 nucleic acid molecule or vectors containing a nucleic acid molecule which encodes a DHDR-7 polypeptide (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, and the like. The expression vectors of the invention can be introduced into host cells to thereby produce proteins or peptides, including fusion proteins or peptides, encoded by nucleic acids as described herein (e.g., DHDR-7 polypeptides, mutant forms of DHDR-7 polypeptides, fusion proteins, and the like).

Accordingly, an exemplary embodiment provides a method for producing a polypeptide, preferably a DHDR-7 polypeptide, by culturing in a suitable medium a host cell of the invention (e.g., a mammalian host cell such as a non-human mammalian cell) containing a recombinant expression vector, such that the polypeptide is produced.

The recombinant expression vectors of the invention can be designed for expression of DHDR-7 polypeptides in prokaryotic or eukaryotic cells. For example, DHDR-7 polypeptides can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in DHDR-7 activity assays, (e.g., direct assays or competitive assays described in detail below), or to generate antibodies specific for DHDR-7 polypeptides, for example. In a preferred embodiment, a DHDR-7 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the DHDR-7 expression vector is a yeast expression vector. Examples of vectors for expression in yeast *S. cerevisiae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, DHDR-7 polypeptides can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195).

When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to DHDR-7 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a DHDR-7 nucleic acid molecule of the invention is introduced, e.g., a DHDR-7 nucleic acid molecule within a vector (e.g., a recombinant expression vector) or a DHDR-7 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a DHDR-7 polypeptide can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a DHDR-7 polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a DHDR-7 polypeptide. Accordingly, the invention further provides methods for producing a DHDR-7 polypeptide using the host cells of the invention. In one embodiment, the method comprises culturing the host cell of the invention (into which a recombinant expression vector encoding a DHDR-7 polypeptide has been introduced) in a suitable medium such that a DHDR-7 polypeptide is produced. In another embodiment, the method further comprises isolating a DHDR-7 polypeptide from the medium or the host cell.

The host cells of the invention can also be used to produce non-human transgenic animals. For example, in one embodiment, a host cell of the invention is a fertilized oocyte or an embryonic stem cell into which DHDR-7-coding sequences have been introduced. Such host cells can then be used to create non-human transgenic animals in which exogenous DHDR-7 sequences have been introduced into their genome or homologous recombinant animals in which endogenous DHDR-7 sequences have been altered. Such animals are useful for studying the function and/or activity of a DHDR-7 and for identifying and/or evaluating modulators of DHDR-7 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous DHDR-7 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a DHDR-7-encoding nucleic acid into the male pronuclei of a fertilized oocyte, e.g., by microinjection, retroviral infection, and allowing the oocyte to develop in a pseudopregnant female foster animal. The DHDR-7 cDNA sequence of SEQ ID NO:1 can be introduced as a transgene into the genome of a non-human animal. Alternatively, a nonhuman homologue of a human DHDR-7 gene, such as a mouse or rat DHDR-7 gene, can be used as a transgene. Alternatively, a DHDR-7 gene homologue, such as another DHDR-7 family member, can be isolated based on hybridization to the DHDR-7 cDNA sequences of SEQ ID NO:1 or 3, or the DNA insert of the plasmid deposited with ATCC as Accession Number PTA-3439 (described further in subsection I above) and used as a transgene. Intronic sequences and polyadenylation signals can also be included in the transgene to increase the efficiency of expression of the transgene. A tissue-specific regulatory sequence(s) can be operably linked to a DHDR-7 transgene to direct expression of a DHDR-7 polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a DHDR-7 transgene in its genome and/or expression of DHDR-7 mRNA in tissues or cells of the animals. A transgenic founder animal can then be used to breed additional animals carrying the transgene. Moreover, transgenic animals carrying a transgene encoding a DHDR-7 polypeptide can further be bred to other transgenic animals carrying other transgenes.

To create a homologous recombinant animal, a vector is prepared which contains at least a portion of a DHDR-7 gene into which a deletion, addition or substitution has been introduced to thereby alter, e.g., functionally disrupt, the DHDR-7 gene. The DHDR-7 gene can be a human gene (e.g., the cDNA of SEQ ID NO:3), but more preferably, is a non-human homologue of a human DHDR-7 gene (e.g., a cDNA isolated by stringent hybridization with the nucleotide sequence of SEQ ID NO:1). For example, a mouse DHDR-7 gene can be used to construct a homologous recombination nucleic acid molecule, e.g., a vector, suitable for altering an endogenous DHDR-7 gene in the mouse genome. In a preferred embodiment, the homologous recombination nucleic acid molecule is designed such that, upon homologous recombination, the endogenous DHDR-7 gene is functionally disrupted (i.e., no longer encodes a functional protein; also referred to as a "knock out" vector). Alternatively, the homologous recombination nucleic acid molecule can be designed such that, upon homologous recombination, the endogenous DHDR-7 gene is mutated or otherwise altered but still encodes functional polypeptide (e.g., the upstream regulatory region can be altered to thereby alter the expression of the endogenous DHDR-7 polypeptide). In the homologous recombination nucleic acid molecule, the altered portion of the DHDR-7 gene is flanked at its 5' and 3' ends by additional nucleic acid sequence of the DHDR-7 gene to allow for homologous recombination to occur between the exogenous DHDR-7 gene carried by the homologous recombination nucleic acid molecule and an endogenous DHDR-7 gene in a cell, e.g., an embryonic stem cell. The additional flanking DHDR-7 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced DHDR-7 gene has homologously recombined with the endogenous DHDR-7 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P 1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The DHDR-7 nucleic acid molecules, fragments of DHDR-7 polypeptides, and anti-DHDR-7 antibodies (also referred to herein as "active compounds") of the invention can be incorporated into pharmaceutical compositions suitable for administration. Such compositions typically comprise the nucleic acid molecule, polypeptide, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a DHDR-7 polypeptide or an anti-DHDR-7 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a polypeptide or antibody can include a single treatment or, preferably, can include a series of treatments.

In a preferred example, a subject is treated with antibody or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a DHDR-7 polypeptide of the invention has one or more of the following activities: 1) it modulates metabolism or catabolism of biochemical molecules necessary for energy production or storage, 2) it modulates intra- or inter-cellular signaling, 3) it modulates metabolism or catabolism of metabolically important biomolecules, 4) it modulates the dehydrogenation of acyl-CoA esters, 5) it modulates detoxification of potentially harmful compounds, 6) it modulates the beta oxidation cycle for fatty acids, and 7) it modulates energy production in the cell.

The isolated nucleic acid molecules of the invention can be used, for example, to express DHDR-7 polypeptide (e.g., via a recombinant expression vector in a host cell in gene therapy applications), to detect DHDR-7 mRNA (e.g., in a biological sample) or a genetic alteration in a DHDR-7 gene, and to modulate DHDR-7 activity, as described further below. The DHDR-7 polypeptides can be used to treat disorders characterized by insufficient or excessive production of a DHDR-7 substrate or production of DHDR-7 inhibitors. In addition, the DHDR-7 polypeptides can be used to screen for naturally occurring DHDR-7 substrates, to screen for drugs or compounds which modulate DHDR-7 activity, as well as to treat disorders characterized by insufficient or excessive production of DHDR-7 polypeptide or production of DHDR-7 polypeptide forms which have decreased, aberrant or unwanted activity compared to DHDR-7 wild type polypeptide (e.g., cardiac disorders, CNS disorders, or cellular growth, differentiation, or migration disorders, such as cancer). Moreover, the anti-DHDR-7 antibodies of the invention can be used to detect and isolate DHDR-7 polypeptides, to regulate the bioavailability of DHDR-7 polypeptides, and modulate DHDR-7 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to DHDR-7 polypeptides, have a stimulatory or inhibitory effect on, for example, DHDR-7 expression or DHDR-7 activity, or have a stimulatory or inhibitory effect on, for example, the expression or activity of DHDR-7 substrate.

In one embodiment, the invention provides assays for screening candidate or test compounds which are substrates of a DHDR-7 polypeptide or polypeptide or biologically active portion thereof. In another embodiment, the invention provides assays for screening candidate or test compounds which bind to or modulate the activity of a DHDR-7 polypeptide or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA*. 90:6909; Erb et al. (1994) *Proc. Natl. Acad Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a DHDR-7 polypeptide or biologically active portion thereof is contacted with a test compound and the ability of the test compound to modulate DHDR-7 activity is determined. Determining the ability of the test compound to modulate DHDR-7 activity can be accomplished by monitoring, for example, the production of one or more specific metabolites in a cell which expresses DHDR-7 (see, e.g., Saada et al. (2000) *Biochem Biophys. Res. Commun.* 269: 382–386). The cell, for example, can be of mammalian origin, e.g., a colon, breast, lung, or ovarian tumor cell, or a normal colon, breast, lung, or ovarian cell.

The ability of the test compound to modulate DHDR-7 binding to a substrate (e.g., an acyl-CoA ester) or to bind to DHDR-7 can also be determined. Determining the ability of the test compound to modulate DHDR-7 binding to a substrate can be accomplished, for example, by coupling the DHDR-7 substrate with a radioisotope or enzymatic label such that binding of the DHDR-7 substrate to DHDR-7 can be determined by detecting the labeled DHDR-7 substrate in a complex. Alternatively, DHDR-7 could be coupled with a radioisotope or enzymatic label to monitor the ability of a test compound to modulate DHDR-7 binding to a DHDR-7 substrate in a complex. Determining the ability of the test compound to bind DHDR-7 can be accomplished, for example, by coupling the compound with a radioisotope or enzymatic label such that binding of the compound to DHDR-7 can be determined by detecting the labeled DHDR-7 compound in a complex. For example, compounds (e.g., DHDR-7 substrates) can be labeled with $^{125}I$, $^{35}S$, $^{14}C$, or $^3H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a DHDR-7 substrate) to interact with DHDR-7 without the labeling of any of the interactants. For example, a microphysiometer can be used to detect the interaction of a compound with DHDR-7 without the labeling of either the compound or the DHDR-7. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and DHDR-7.

In another embodiment, an assay is a cell-based assay comprising contacting a cell expressing a DHDR-7 target molecule (e.g., a DHDR-7 substrate) with a test compound and determining the ability of the test compound to modulate (e.g., stimulate or inhibit) the activity of the DHDR-7 target molecule. Determining the ability of the test compound to modulate the activity of a DHDR-7 target molecule can be accomplished, for example, by determining the ability of the DHDR-7 polypeptide to bind to or interact with the DHDR-7 target molecule, e.g., acyl Co-A esters, or by monitoring, for example, the alpha, beta-dehydrogenation of acyl-CoA esters, the reduction of flavoproteins, the beta oxidation of fatty acids, or the modulation of cellular proliferation, growth, or differentiation. The cell, for example, can be of mammalian origin, e.g., an epithelial cell, for example a colon, breast, lung, or ovarian epithelial cell, or a tumor cell.

Determining the ability of the DHDR-7 polypeptide, or a biologically active fragment thereof, to bind to or interact with a DHDR-7 target molecule can be accomplished by one of the methods described above for determining direct binding. In a preferred embodiment, determining the ability of the DHDR-7 polypeptide to bind to or interact with a DHDR-7 target molecule can be accomplished by determining the activity of the target molecule. For example, the activity of the target molecule can be determined by detecting induction of a cellular response, detecting catalytic/enzymatic activity of the target using an appropriate substrate, detecting the induction of a reporter gene (comprising a target-responsive regulatory element operatively linked to a nucleic acid encoding a detectable marker, e.g., luciferase), or detecting a target-regulated cellular response.

Figure 5:
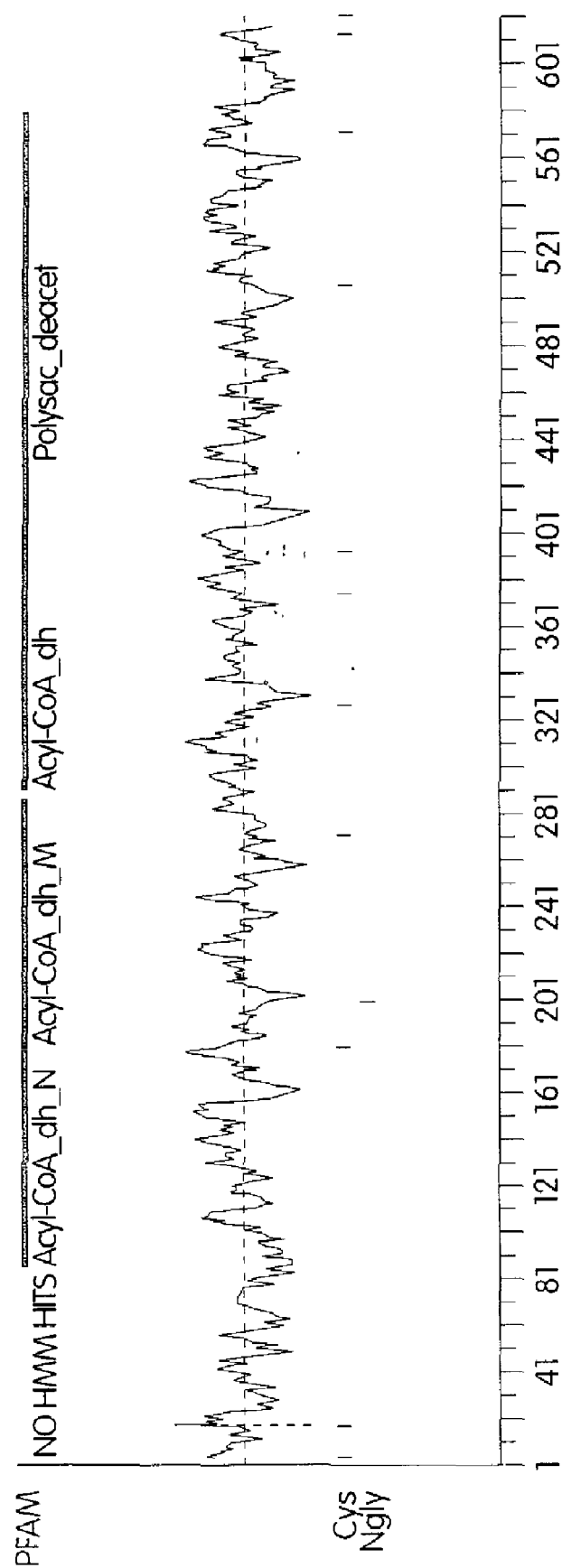
FIG. 5 depicts a hydrophobicity analysis of the human DHDR-7 protein.

In yet another embodiment, an assay of the present invention is a cell-free assay in which a DHDR-7 polypeptide or biologically active portion thereof is contacted with a test compound and the ability of the test compound to bind to the DHDR-7 polypeptide or biologically active portion thereof is determined. Preferred biologically active portions of the DHDR-7 polypeptides to be used in assays of the present invention include fragments which participate in interactions with non-DHDR-7 molecules, e.g., fragments with high surface probability scores (see, for example, FIG. 5). Binding of the test compound to the DHDR-7 polypeptide can be determined either directly or indirectly as described above. In a preferred embodiment, the assay includes contacting the DHDR-7 polypeptide or biologically active portion thereof with a known compound which binds DHDR-7 to form an assay mixture, contacting the assay mixture with a test compound, and determining the ability of the test compound to interact with a DHDR-7 polypeptide, wherein determining the ability of the test compound to interact with a DHDR-7 polypeptide comprises determining the ability of the test compound to preferentially bind to DHDR-7 or biologically active portion thereof as compared to the known compound.

In another embodiment, the assay is a cell-free assay in which a DHDR-7 polypeptide or biologically active portion thereof is contacted with a test compound and the ability of the test compound to modulate (e.g., stimulate or inhibit) the activity of the DHDR-7 polypeptide or biologically active portion thereof is determined. Determining the ability of the test compound to modulate the activity of a DHDR-7 polypeptide can be accomplished, for example, by determining the ability of the DHDR-7 polypeptide to bind to a DHDR-7 target molecule by one of the methods described above for determining direct binding. Determining the ability of the DHDR-7 polypeptide to bind to a DHDR-7 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a DHDR-7 polypeptide can be accomplished by determining the ability of the DHDR-7 polypeptide to further modulate the activity of a downstream effector of a DHDR-7 target molecule. For example, the activity of the effector molecule on an appropriate target can be determined or the binding of the effector to an appropriate target can be determined as previously described.

In yet another embodiment, the cell-free assay involves contacting a DHDR-7 polypeptide or biologically active portion thereof with a known compound which binds the DHDR-7 polypeptide to form an assay mixture, contacting the assay mixture with a test compound, and determining the ability of the test compound to interact with the DHDR-7 polypeptide, wherein determining the ability of the test compound to interact with the DHDR-7 polypeptide comprises determining the ability of the DHDR-7 polypeptide to preferentially bind to or modulate the activity of a DHDR-7 target molecule.

In more than one embodiment of the above assay methods of the present invention, it may be desirable to immobilize either DHDR-7 or its target molecule to facilitate separation of complexed from uncomplexed forms of one or both of the proteins, as well as to accommodate automation of the assay. Binding of a test compound to a DHDR-7 polypeptide, or interaction of a DHDR-7 polypeptide with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/DHDR-7 fusion proteins or glutathione-S-transferase/target fusion proteins can be adsorbed onto glutathione sepharose beads (Sigma Chemical, St. Louis, Mo.) or glutathione derivatized micrometer plates, which are then combined with the test compound or the test compound and either the non-adsorbed target protein or DHDR-7 polypeptide, and the mixture incubated under conditions conducive to complex formation (e.g., at physiological conditions for salt and pH). Following incubation, the beads or micrometer plate wells are washed to remove any unbound components, the matrix immobilized in the case of beads, complex determined either directly or indirectly, for example, as described above. Alternatively, the complexes can be dissociated from the matrix, and the level of DHDR-7 binding or activity determined using standard techniques.

Other techniques for immobilizing proteins on matrices can also be used in the screening assays of the invention. For example, either a DHDR-7 polypeptide or a DHDR-7 target molecule can be immobilized utilizing conjugation of biotin and streptavidin. Biotinylated DHDR-7 polypeptide or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with DHDR-7 polypeptide or target molecules but which do not interfere with binding of the DHDR-7 polypeptide to its target molecule can be derivatized to the wells of the plate, and unbound target or DHDR-7 polypeptide trapped in the wells by antibody conjugation. Methods for detecting such complexes, in addition to those described above for the GST-immobilized complexes, include immunodetection of complexes using antibodies reactive with the DHDR-7 polypeptide or target molecule, as well as enzyme-linked assays which rely on detecting an enzymatic activity associated with the DHDR-7 polypeptide or target molecule.

In another embodiment, modulators of DHDR-7 expression are identified in a method wherein a cell is contacted with a candidate compound and the expression of DHDR-7 mRNA or polypeptide in the cell is determined. The level of expression of DHDR-7 mRNA or polypeptide in the presence of the candidate compound is compared to the level of expression of DHDR-7 mRNA or polypeptide in the absence of the candidate compound. The candidate compound can then be identified as a modulator of DHDR-7 expression based on this comparison. For example, when expression of DHDR-7 mRNA or polypeptide is greater (statistically significantly greater) in the presence of the candidate compound than in its absence, the candidate compound is identified as a stimulator of DHDR-7 mRNA or polypeptide expression. Alternatively, when expression of DHDR-7 mRNA or polypeptide is less (statistically significantly less) in the presence of the candidate compound than in its absence, the candidate compound is identified as an inhibitor of DHDR-7 mRNA or polypeptide expression. The level of DHDR-7 mRNA or polypeptide expression in the cells can be determined by methods described herein for detecting DHDR-7 mRNA or polypeptide.

In yet another aspect of the invention, the DHDR-7 polypeptides can be used as "bait proteins" in a two-hybrid assay or three-hybrid assay (see, e.g., U.S. Pat. No. 5,283, 317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with DHDR-7 ("DHDR-7-binding proteins" or "DHDR-7-bp") and are involved in DHDR-7 activity. Such DHDR-7-binding proteins are also likely to be involved in the propagation of signals by the DHDR-7 polypeptides or DHDR-7 targets as, for example, downstream elements of a DHDR-7-mediated signaling pathway. Alternatively, such DHDR-7-binding proteins are likely to be DHDR-7 inhibitors.

The two-hybrid system is based on the modular nature of most transcription factors, which consist of separable DNA-binding and activation domains. Briefly, the assay utilizes two different DNA constructs. In one construct, the gene that codes for a DHDR-7 polypeptide is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a DHDR-7-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the DHDR-7 polypeptide.

In another aspect, the invention pertains to a combination of two or more of the assays described herein. For example, a modulating agent can be identified using a cell-based or a cell free assay, and the ability of the agent to modulate the activity of a DHDR-7 polypeptide can be confirmed in vivo, e.g., in an animal such as an animal model for cellular transformation and/or tumorgenesis.

Examples of animal models of cancer include transplantable models (e.g., xenografts of colon tumors such as Co-3, AC3603 or WiDr or into immunocompromised mice such as SCID or nude mice); transgenic models (e.g., B66-Min/+ mouse); chemical induction models, e.g., carcinogen (e.g., azoxymethane, 2-dimethylhydrazine, or N-nitrosodimethylamine) treated rats or mice; models of liver metastasis from colon cancer such as that described by Rashidi et al. (2000) *Anticancer Res* 20(2A):715; and cancer cell implantation or inoculation models as described in, for example, Fingert, et al. (1987) *Cancer Res* 46(14):3824–9 and Teraoka, et al. (1995) *Jpn J Cancer Res* 86(5):419–23.

This invention further pertains to novel agents identified by the above-described screening assays. Accordingly, it is within the scope of this invention to further use an agent identified as described herein in an appropriate animal model. For example, an agent identified as described herein (e.g., a DHDR-7 modulating agent, an antisense DHDR-7 nucleic acid molecule, a DHDR-7-specific antibody, or a DHDR-7-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein. In one embodiment, the invention features a method of treating a subject having a cellular growth or proliferation disorder that involves administering to the subject an DHDR-7 modulator such that treatment occurs. In another embodiment, the invention features a method of treating a subject having cancer, e.g., colon, breast, lung, or ovarian cancer, that involves treating a subject with an DHDR-7 modulator, such that treatment occurs. Preferred DHDR-7 modulators include, but are not limited to, DHDR-7 proteins or biologically active fragments, DHDR-7 nucleic acid molecules, DHDR-7 antibodies, ribozymes, and DHDR-7 antisense oligonucleotides designed based on the DHDR-7 nucleotide sequences disclosed herein, as well as peptides, organic and non-organic small molecules identified as being capable of modulating DHDR-7 expression and/or activity, for example, according to at least one of the screening assays described herein.

Any of the compounds, including but not limited to compounds such as those identified in the foregoing assay systems, may be tested for the ability to ameliorate cellular growth or proliferation disorder symptoms. Cell-based and animal model-based assays for the identification of compounds exhibiting such an ability to ameliorate cellular growth or proliferation disorder systems are described herein.

In one aspect, cell-based systems, as described herein, may be used to identify compounds which may act to ameliorate cellular growth or proliferation disorder symptoms, for example, reduction in tumor burden, tumor size, tumor cell growth, differentiation, and/or proliferation, and invasive and/or metastatic potential before and after treatment. For example, such cell systems may be exposed to a compound, suspected of exhibiting an ability to ameliorate cellular growth or proliferation disorder symptoms, at a sufficient concentration and for a time sufficient to elicit such an amelioration of cellular growth or proliferation disorder symptoms in the exposed cells. After exposure, the cells are examined to determine whether one or more of the cellular growth or proliferation disorder cellular phenotypes has been altered to resemble a more normal or more wild type, non-cellular growth or proliferation disorder phenotype. Cellular phenotypes that are associated with cellular growth and/or proliferation disorders include aberrant proliferation, growth, and migration, anchorage independent growth, and loss of contact inhibition.

In addition, animal-based cellular growth or proliferation disorder systems, such as those described herein, may be used to identify compounds capable of ameliorating cellular growth or proliferation disorder symptoms. Such animal models may be used as test substrates for the identification of drugs, pharmaceuticals, therapies, and interventions which may be effective in treating cellular growth or proliferation disorders. For example, animal models may be exposed to a compound suspected of exhibiting an ability to ameliorate cellular growth or proliferation disorder symptoms, at a sufficient concentration and for a time sufficient to elicit such an amelioration of cellular growth or proliferation disorder symptoms in the exposed animals. The response of the animals to the exposure may be monitored by assessing the reversal of cellular growth or proliferation disorders, or symptoms associated therewith, for example, reduction in tumor burden, tumor size, and invasive and/or metastatic potential before and after treatment.

With regard to intervention, any treatments which reverse any aspect of cellular growth or proliferation disorder symptoms should be considered as candidates for human cellular growth or proliferation disorder therapeutic intervention. Dosages of test compounds may be determined by deriving dose-response curves.

Additionally, gene expression patterns may be utilized to assess the ability of a compound to ameliorate cellular growth and/or proliferation disorder symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, cell growth, proliferation, differentiation, transformation, tumorigenesis, metastasis, and carcinogen exposure. Gene expression profiles may be generated, for example, by utilizing a differential display procedure, Northern analysis and/or RT-PCR. In one embodiment, DHDR-7 gene sequences may be used as probes and/or PCR primers for the generation and corroboration of such gene expression profiles.

Gene expression profiles may be characterized for known states within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a cellular growth or proliferation disorder model system to more closely resemble the control system. Administration of a compound may, alternatively, cause the gene expression profile of a control system to begin to mimic a cellular growth and/or proliferation disorder state. Such a compound may, for example, be used in further characterizing the compound of interest, or may be used in the generation of additional animal models.

B. Cell- and Animal-Based Model Systems

Described herein are cell- and animal-based systems which act as models for cellular growth or proliferation disorders. These systems may be used in a variety of applications. For example, the cell- and animal-based model systems may be used to further characterize differentially expressed genes associated with cellular growth or proliferation disorder, e.g., DHDR-7. In addition, animal- and cell-based assays may be used as part of screening strategies designed to identify compounds which are capable of ameliorating cellular growth or proliferation disorder symptoms, as described, below. Thus, the animal- and cell-based models may be used to identify drugs, pharmaceuticals, therapies and interventions which may be effective in treating cellular growth or proliferation disorders.

1. Animal-Based Systems

Animal-based model systems of cellular growth or proliferation disorders may include, but are not limited to, non-recombinant and engineered transgenic animals.

Animal based models for studying tumorigenesis in vivo are well known in the art (reviewed in Animal Models of Cancer Predisposition Syndromes, Hiai, H and Hino, O (eds.) 1999, *Progress in Experimental Tumor Research*, Vol. 35; Clarke A R *Carcinogenesis* (2000) 21:435–41) and include, for example, carcinogen-induced tumors (Rithidech, K et al. *Mutat Res* (1999) 428:33–39; Miller, M L et al. *Environ Mol Mutagen* (2000) 35:319–327), injection and/or transplantation of tumor cells into an animal, as well as animals bearing mutations in growth regulatory genes, for example, oncogenes (e.g., ras) (Arbeit, J M et al. *Am J Pathol* (1993) 142:1187–1197; Sinn, E et al. *Cell* (1987) 49:465–475; Thorgeirsson, S S et al. *Toxicol Lett* (2000) 112–113:553–555) and tumor suppressor genes (e.g., p53) (Vooijs, M et al. *Oncogene* (1999) 18:5293–5303; Clark A R *Cancer Metast Rev* (1995) 14:125–148; Kumar, T R et al. *J Intern Med* (1995) 238:233–238; Donehower, L A et al. (1992) Nature 356215–221). Furthermore, experimental model systems are available for the study of, for example, colon cancer (Heyer J, et al. (1999) Oncogene 18(38): 5325–33), ovarian cancer (Hamilton, T C et al. *Semin Oncol* (1984) 11:285–298; Rahman, N A et al. *Mol Cell Endocrinol* (1998) 145:167–174; Beamer, W G et al. *Toxicol Pathol* (1998) 26:704–710), gastric cancer (Thompson, J et al. *Int J Cancer* (2000) 86:863–869; Fodde, R et al. *Cytogenet Cell Genet* (1999) 86:105–111), breast cancer (Li, M et al. *Oncogene* (2000) 19:1010–1019; Green, J E et al. *Oncogene* (2000) 19:1020–1027), melanoma (Satyamoorthy, K et al. *Cancer Metast Rev* (1999) 18:401–405), and prostate cancer (Shirai, T et al. *Mutat Res* (2000) 462:219–226; Bostwick, D G et al. *Prostate* (2000) 43:286–294).

Additionally, animal models exhibiting cellular growth or proliferation disorder symptoms may be engineered by using, for example, DHDR-7 gene sequences described above, in conjunction with techniques for producing transgenic animals that are well known to those of skill in the art. For example, DHDR-7 gene sequences may be introduced into, and overexpressed in, the genome of the animal of interest, or, if endogenous DHDR-7 gene sequences are present, they may either be overexpressed or, alternatively, be disrupted in order to underexpress or inactivate DHDR-7 gene expression, such as described for the disruption of apoE in mice (Plump et al., 1992, *Cell* 71: 343–353).

The host cells of the invention can also be used to produce non-human transgenic animals. For example, in one embodiment, a host cell of the invention is a fertilized oocyte or an embryonic stem cell into which DHDR-7-coding sequences have been introduced. Such host cells can then be used to create non-human transgenic animals in which exogenous DHDR-7 sequences have been introduced into their genome or homologous recombinant animals in which endogenous DHDR-7 sequences have been altered. Such animals are useful for studying the function and/or activity of a DHDR-7 and for identifying and/or evaluating modulators of DHDR-7 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous DHDR-7 gene has been altered by homologous recombination between the endogenous gene and an exogenous DNA molecule introduced into a cell of the animal, e.g., an embryonic cell of the animal, prior to development of the animal.

A transgenic animal of the invention can be created using the methods described herein. DHDR-7 transgenic animals that express DHDR-7 mRNA or a DHDR-7 peptide (detected immunocytochemically, using antibodies directed against DHDR-7 epitopes) at easily detectable levels should then be further evaluated to identify those animals which display characteristic cellular growth or proliferation disorder symptoms. Tumorigenic disease symptoms include, for example, tumor burden, invasion and/or metastasis.

Additionally, specific cell types (e.g., tumor cells, colon cells, breast cells, lung cells, or ovarian cells) within the transgenic animals may be analyzed and assayed for cellular phenotypes characteristic of cellular growth or proliferation disorders. In the case of endothelial cells, such phenotypes include, but are not limited to cell proliferation, growth and migration. Cellular phenotypes associated with a tumorigenic disorder include, for example, dysregulated proliferation and migration, anchorage independent growth, and loss of contact inhibition. Cellular phenotypes may include a particular cell type's pattern of expression of genes associated with cellular growth or proliferation disorders as compared to known expression profiles of the particular cell type in animals exhibiting cellular growth or proliferation disorder symptoms.

2. Cell-Based Systems

Cells that contain and express DHDR-7 gene sequences which encode a DHDR-7 protein, and, further, exhibit cellular phenotypes associated with cellular growth or proliferation disorders, may be used to identify compounds that exhibit anti-tumorigenic disease activity. Such cells may include endothelial cells such as human umbilical vein endothelial cells (HUVECs), human microvascular endothelial cells (HMVEC); tumor cell lines such as HT-1080 (ATCC# CCL-121), HCT-15 (ATCC# CCL-225), HCC70 (ATCC# CRL-2315), M059J (ATCC# CRL-2366), and NCI-N417 (ATCC# CRL-5809); as well as generic mammalian cell lines such as HeLa cells and COS cells, e.g., COS-7 (ATCC# CRL-1651). Further, such cells may include recombinant, transgenic cell lines. For example, the cellular growth or proliferation disorder animal models of the invention, discussed above, may be used to generate cell lines, containing one or more cell types involved in cellular growth or proliferation disorders, that can be used as cell culture models for this disorder. While primary cultures derived from the cellular growth or proliferation disorder transgenic animals of the invention may be utilized, the generation of continuous cell lines is preferred. For examples of techniques which may be used to derive a continuous cell line from the transgenic animals, see Small et al., (1985) *Mol. Cell Biol.* 5:642–648.

Alternatively, cells of a cell type known to be involved in cellular growth or proliferation disorders may be transfected with sequences capable of increasing or decreasing the amount of DHDR-7 gene expression within the cell. For example, DHDR-7 gene sequences may be introduced into, and overexpressed in, the genome of the cell of interest, or, if endogenous DHDR-7 gene sequences are present, they may be either overexpressed or, alternatively disrupted in order to underexpress or inactivate DHDR-7 gene expression.

In order to overexpress an DHDR-7 gene, the coding portion of the DHDR-7 gene may be ligated to a regulatory sequence which is capable of driving gene expression in the cell type of interest, e.g., a tumor cell or a colon cell, a breast cell, a lung cell, or an ovarian cell. Such regulatory regions will be well known to those of skill in the art, and may be utilized in the absence of undue experimentation. Recombinant methods for expressing target genes are described above.

For underexpression of an endogenous DHDR-7 gene sequence, such a sequence may be isolated and engineered such that when reintroduced into the genome of the cell type of interest, the endogenous DHDR-7 alleles will be inactivated. Preferably, the engineered DHDR-7 sequence is introduced via gene targeting such that the endogenous DHDR-7 sequence is disrupted upon integration of the engineered DHDR-7 sequence into the cell's genome. Transfection of host cells with DHDR-7 genes is discussed, above.

Cells treated with compounds or transfected with DHDR-7 genes can be examined for phenotypes associated with cellular growth or proliferation disorders. Cells (e.g., tumor cells) can be treated with test compounds or transfected with genetically engineered DHDR-7 genes and examined for phenotypes associated with tumorigenic disease, including, but not limited to changes in cellular morphology, cell proliferation, cell migration, cell transformation, anchorage independent growth, and loss of contact inhibition.

Transfection of DHDR-7 nucleic acid may be accomplished by using standard techniques (described in, for example, Ausubel (1989) supra). Transfected cells should be evaluated for the presence of the recombinant DHDR-7 gene sequences, for expression and accumulation of DHDR-7 mRNA, and for the presence of recombinant DHDR-7 protein production. In instances wherein a decrease in DHDR-7 gene expression is desired, standard techniques may be used to demonstrate whether a decrease in endogenous DHDR-7 gene expression and/or in DHDR-7 protein production is achieved.

Cellular models for the study of tumorigenesis are known in the art, and include cell lines derived from clinical tumors, cells exposed to chemotherapeutic agents, cells exposed to carcinogenic agents, and cell lines with genetic alterations in growth regulatory genes, for example, oncogenes (e.g., ras) and tumor suppressor genes (e.g., p53).

C. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the DHDR-7 nucleotide sequences, described herein, can be used to map the location of the DHDR-7 genes on a chromosome. The mapping of the DHDR-7 sequences to chromosomes is an important first step in correlating these sequences with genes associated with disease.

Briefly, DHDR-7 genes can be mapped to chromosomes by preparing PCR primers (preferably 15–25 bp in length) from the DHDR-7 nucleotide sequences. Computer analysis of the DHDR-7 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the DHDR-7 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the DHDR-7 nucleotide sequences to design oligonucleotide primers, sublocalization can be achieved with panels of fragments from specific chromosomes. Other mapping strategies which can similarly be used to map a DHDR-7 sequence to its chromosome include in situ hybridization (described in Fan, Y. et al. (1990) *Proc. Natl. Acad. Sci. USA,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the DHDR-7 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The DHDR-7 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the DHDR-7 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The DHDR-7 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from DHDR-7 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of DHDR-7 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the DHDR-7 nucleotide sequences or portions thereof, e.g., fragments derived from the noncoding regions of SEQ ID NO:1 having a length of at least 20 bases, preferably at least 30 bases.

The DHDR-7 nucleotide sequences described herein can further be used to provide polynucleotide reagents, e.g., labeled or labelable probes which can be used in, for example, an in situ hybridization technique, to identify a specific tissue, e.g., liver tissue. This can be very useful in cases where a forensic pathologist is presented with a tissue of unknown origin. Panels of such DHDR-7 probes can be used to identify tissue by species and/or by organ type.

In a similar fashion, these reagents, e.g., DHDR-7 primers or probes can be used to screen tissue culture for contamination (i.e. screen for the presence of a mixture of different types of cells in a culture).

D. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining DHDR-7 polypeptide and/or nucleic acid expression as well as DHDR-7 activity, in the context of a biological sample (e.g., blood, serum, cells, tissue) to thereby determine whether an individual is afflicted with a disease or disorder, or is at risk of developing a disorder associated with aberrant or unwanted DHDR-7 expression or activity. The invention also provides for prognostic (or predictive) assays for determining whether an individual is at risk of developing a disorder associated with DHDR-7 polypeptide, nucleic acid expression or activity. For example, mutations in a DHDR-7 gene can be assayed in a biological sample. Such assays can be used for prognostic or predictive purpose to thereby prophylactically treat an individual prior to the onset of a disorder characterized by or associated with DHDR-7 polypeptide, nucleic acid expression or activity.

Another aspect of the invention pertains to monitoring the influence of agents (e.g., drugs, compounds) on the expression or activity of DHDR-7 in clinical trials.

These and other agents are described in further detail in the following sections.

1. Diagnostic Assays

An exemplary method for detecting the presence or absence of DHDR-7 polypeptide or nucleic acid in a biological sample involves obtaining a biological sample from a test subject and contacting the biological sample with a compound or an agent capable of detecting DHDR-7 polypeptide or nucleic acid (e.g., mRNA, or genomic DNA) that encodes DHDR-7 polypeptide such that the presence of DHDR-7 polypeptide or nucleic acid is detected in the biological sample. In another aspect, the present invention provides a method for detecting the presence of DHDR-7 activity in a biological sample by contacting the biological sample with an agent capable of detecting an indicator of DHDR-7 activity such that the presence of DHDR-7 activity is detected in the biological sample. A preferred agent for detecting DHDR-7 mRNA or genomic DNA is a labeled nucleic acid probe capable of hybridizing to DHDR-7 mRNA or genomic DNA. The nucleic acid probe can be, for example, the DHDR-7 nucleic acid set forth in SEQ ID NO:1 or 3, or the DNA insert of the plasmid deposited with ATCC as Accession Number PTA-3439, or a portion thereof, such as an oligonucleotide of at least 15, 30, 50, 100, 250 or 500 nucleotides in length and sufficient to specifically hybridize under stringent conditions to DHDR-7 mRNA or genomic DNA. Other suitable probes for use in the diagnostic assays of the invention are described herein.

A preferred agent for detecting DHDR-7 polypeptide is an antibody capable of binding to DHDR-7 polypeptide, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect DHDR-7 mRNA, polypeptide, or genomic DNA in a biological sample in vitro as well as in vivo. For example, in vitro techniques for detection of DHDR-7 mRNA include Northern hybridizations and in situ hybridizations. In vitro techniques for detection of DHDR-7 polypeptide include enzyme linked immunosorbent assays (ELISAs), Western blots, immunoprecipitations and immunofluorescence. In vitro techniques for detection of DHDR-7 genomic DNA include Southern hybridizations. Furthermore, in vivo techniques for detection of DHDR-7 polypeptide include introducing into a subject a labeled anti-DHDR-7 antibody. For example, the antibody can be labeled with a radioactive marker whose presence and location in a subject can be detected by standard imaging techniques.

The present invention also provides diagnostic assays for identifying the presence or absence of a genetic alteration characterized by at least one of (i) aberrant modification or mutation of a gene encoding a DHDR-7 polypeptide; (ii) aberrant expression of a gene encoding a DHDR-7 polypeptide; (iii) mis-regulation of the gene; and (iii) aberrant post-translational modification of a DHDR-7 polypeptide, wherein a wild-type form of the gene encodes a polypeptide with a DHDR-7 activity. "Misexpression or aberrant expression", as used herein, refers to a non-wild type pattern of gene expression, at the RNA or protein level. It includes, but is not limited to, expression at non-wild type levels (e.g., over or under expression); a pattern of expression that differs from wild type in terms of the time or stage at which the gene is expressed (e.g., increased or decreased expression (as compared with wild type) at a predetermined developmental period or stage); a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extra-cellular stimulus on expression of the gene (e.g., a pattern of increased or decreased expression (as compared with wild type) in the presence of an increase or decrease in the strength of the stimulus).

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject. Also preferred are biological samples from tumors (e.g., tumor biopsies). Additional preferred biological samples include, for example, prostate tissue, liver tissue, breast tissue, skeletal muscle tissue, brain tissue, breast tissue, heart tissue, ovarian tissue, kidney tissue, lung tissue, colon tissue, vascular tissue, aortic tissue, thyroid tissue, placental tissue, intestinal tissue, cervical tissue, splenic tissue, esophageal tissue, thymic tissue, tonsillar tissue, lymph nodes and osteogenic cells.

In another embodiment, the methods further involve obtaining a control biological sample from a control subject, contacting the control sample with a compound or agent capable of detecting DHDR-7 polypeptide, mRNA, or genomic DNA, such that the presence of DHDR-7 polypeptide, mRNA or genomic DNA is detected in the biological sample, and comparing the presence of DHDR-7 polypeptide, mRNA or genomic DNA in the control sample with the presence of DHDR-7 polypeptide, mRNA or genomic DNA in the test sample.

The invention also encompasses kits for detecting the presence of DHDR-7 in a biological sample. For example, the kit can comprise a labeled compound or agent capable of detecting DHDR-7 polypeptide or MRNA in a biological sample; means for determining the amount of DHDR-7 in the sample; and means for comparing the amount of DHDR-7 in the sample with a standard. The compound or agent can be packaged in a suitable container. The kit can further comprise instructions for using the kit to detect DHDR-7 polypeptide or nucleic acid.

2. Prognostic Assays

The diagnostic methods described herein can furthermore be utilized to identify subjects having or at risk of developing a disease or disorder associated with aberrant or unwanted DHDR-7 expression or activity. As used herein, the term "aberrant" includes a DHDR-7 expression or activity which deviates from the wild type DHDR-7 expression or activity. Aberrant expression or activity includes increased or decreased expression or activity, as well as expression or activity which does not follow the wild type developmental pattern of expression or the subcellular pattern of expression. For example, aberrant DHDR-7 expression or activity is intended to include the cases in which a mutation in the DHDR-7 gene causes the DHDR-7 gene to be under-expressed or over-expressed and situations in which such mutations result in a non-functional DHDR-7 polypeptide or a polypeptide which does not function in a wild-type fashion, e.g., a polypeptide which does not interact with a DHDR-7 substrate, or one which interacts with a non-DHDR-7 substrate. As used herein, the term "unwanted" includes an unwanted phenomenon involved in a biological response, such as cellular proliferation. For example, the term unwanted includes a DHDR-7 expression or activity which is undesirable in a subject.

The assays described herein, such as the preceding diagnostic assays or the following assays, can be utilized to identify a subject having or at risk of developing a disorder associated with a misregulation in DHDR-7 polypeptide activity or nucleic acid expression, such as a cardiac disorder, a CNS disorder, or a cellular proliferation, growth, differentiation, or migration disorder, such as cancer. Alternatively, the prognostic assays can be utilized to identify a subject having or at risk for developing a disorder associated with a misregulation in DHDR-7 polypeptide activity or nucleic acid expression, such as a cardiac disorder, a CNS disorder, or a cellular proliferation, growth, differentiation, or migration disorder, such as cancer. Thus, the present invention provides a method for identifying a disease or disorder associated with aberrant or unwanted DHDR-7 expression or activity in which a test sample is obtained from a subject and DHDR-7 polypeptide or nucleic acid (e.g., mRNA or genomic DNA) is detected, wherein the presence of DHDR-7 polypeptide or nucleic acid is diagnostic for a subject having or at risk of developing a disease or disorder associated with aberrant or unwanted DHDR-7 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted DHDR-7 expression or activity. For example, such methods can be used to determine whether a subject can be effectively treated with an agent for a cardiac disorder, a CNS disorder, or a cellular proliferation, growth, differentiation, or migration disorder, e.g., cancer. Thus, the present invention provides methods for determining whether a subject can be effectively treated with an agent for a disorder associated with aberrant or unwanted DHDR-7 expression or activity in which a test sample is obtained and DHDR-7 polypeptide or nucleic acid expression or activity is detected (e.g., wherein the abundance of DHDR-7 polypeptide or nucleic acid expression or activity is diagnostic for a subject that can be administered the agent to treat a disorder associated with aberrant or unwanted DHDR-7 expression or activity).

The methods of the invention can also be used to detect genetic alterations in a DHDR-7 gene, thereby determining if a subject with the altered gene is at risk for a disorder characterized by misregulation in DHDR-7 polypeptide activity or nucleic acid expression, such as a cardiac disorder, a CNS disorder, or a disorder of cellular growth, differentiation, or migration, e.g., cancer. In preferred embodiments, the methods include detecting, in a sample of cells from the subject, the presence or absence of a genetic alteration characterized by at least one of an alteration affecting the integrity of a gene encoding a DHDR-7-polypeptide, or the mis-expression of the DHDR-7 gene. For example, such genetic alterations can be detected by ascertaining the existence of at least one of 1) a deletion of one or more nucleotides from a DHDR-7 gene; 2) an addition of one or more nucleotides to a DHDR-7 gene; 3) a substitution of one or more nucleotides of a DHDR-7 gene, 4) a chromosomal rearrangement of a DHDR-7 gene; 5) an alteration in the level of a messenger RNA transcript of a DHDR-7 gene, 6) aberrant modification of a DHDR-7 gene, such as of the methylation pattern of the genomic DNA, 7) the presence of a non-wild type splicing pattern of a messenger RNA transcript of a DHDR-7 gene, 8) a non-wild type level of a DHDR-7-polypeptide, 9) allelic loss of a DHDR-7 gene, and 10) inappropriate post-translational modification of a DHDR-7-polypeptide. As described herein, there are a large number of assays known in the art which can be used for detecting alterations in a DHDR-7 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the DHDR-7-gene (see Abravaya et al. (1995) *Nucleic Acids Res* .23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a DHDR-7 gene under conditions such that hybridization and amplification of the DHDR-7-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a DHDR-7 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in DHDR-7 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in DHDR-7 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the DHDR-7 gene and detect mutations by comparing the sequence of the sample DHDR-7 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the DHDR-7 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type DHDR-7 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad Sci USA* 85:4397; Saleeba et al. (1992) *Methods Enzymol.* 217: 286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in DHDR-7 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a DHDR-7 sequence, e.g., a wild-type DHDR-7 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in DHDR-7 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control DHDR-7 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a DHDR-7 gene.

Furthermore, any cell type or tissue in which DHDR-7 is expressed may be utilized in the prognostic assays described herein.

3. Monitoring of Effects During Clinical Trials

Monitoring the influence of agents (e.g., drugs) on the expression or activity of a DHDR-7 polypeptide (e.g., the modulation of metabolism and catabolism of metabolically important biomolecules) can be applied not only in basic drug screening, but also in clinical trials. For example, the effectiveness of an agent determined by a screening assay as described herein to increase DHDR-7 gene expression, polypeptide levels, or upregulate DHDR-7 activity, can be monitored in clinical trials of subjects exhibiting decreased DHDR-7 gene expression, polypeptide levels, or downregulated DHDR-7 activity. Alternatively, the effectiveness of an agent determined by a screening assay to decrease DHDR-7 gene expression, polypeptide levels, or downregulate DHDR-7 activity, can be monitored in clinical trials of subjects exhibiting increased DHDR-7 gene expression, polypeptide levels, or upregulated DHDR-7 activity. In such clinical trials, the expression or activity of a DHDR-7 gene, and preferably, other genes that have been implicated in, for example, a DHDR-7-associated disorder can be used as a "read out" or markers of the phenotype of a particular cell.

For example, and not by way of limitation, genes, including DHDR-7, that are modulated in cells by treatment with an agent (e.g., compound, drug or small molecule) which modulates DHDR-7 activity (e.g., identified in a screening assay as described herein) can be identified. Thus, to study the effect of agents on DHDR-7-associated disorders (e.g., disorders characterized by deregulated metabolism or catabolism of metabolically important biomolecules), for example, in a clinical trial, cells can be isolated and RNA prepared and analyzed for the levels of expression of DHDR-7 and other genes implicated in the DHDR-7-associated disorder, respectively. The levels of gene expression (e.g., a gene expression pattern) can be quantified by northern blot analysis or RT-PCR, as described herein, or alternatively by measuring the amount of polypeptide produced, by one of the methods as described herein, or by measuring the levels of activity of DHDR-7 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a DHDR-7 polypeptide, mRNA, or genomic DNA in the preadministration sample; (iii) obtaining one or more post-administration samples from the subject; (iv) detecting the level of expression or activity of the DHDR-7 polypeptide, mRNA, or genomic DNA in the post-administration samples; (v) comparing the level of expression or activity of the DHDR-7 polypeptide, mRNA, or genomic DNA in the pre-administration sample with the DHDR-7 polypeptide, mRNA, or genomic DNA in the post administration sample or samples; and (vi) altering the administration of the agent to the subject accordingly. For example, increased administration of the agent may be desirable to increase the expression or activity of DHDR-7 to higher levels than detected, i.e., to increase the effectiveness of the agent. Alternatively, decreased administration of the agent may be desirable to decrease expression or activity of DHDR-7 to lower levels than detected, i.e. to decrease the effectiveness of the agent. According to such an embodiment, DHDR-7 expression or activity may be used as an indicator of the effectiveness of an agent, even in the absence of an observable phenotypic response.

E. Methods of Treatment:

The present invention provides for both prophylactic and therapeutic methods of treating a subject at risk of (or susceptible to) a disorder or having a disorder associated with aberrant or unwanted DHDR-7 expression or activity, e.g. a cardiac disorder, a CNS disorder, or a cellular proliferation, growth, differentiation, or migration disorder, such as cancer. "Treatment", or "treating" as used herein, is defined as the application or administration of a therapeutic agent to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease. A therapeutic agent includes, but is not limited to, small molecules, peptides, antibodies, ribozymes and antisense oligonucleotides. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the DHDR-7 molecules of the present invention or DHDR-7 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted DHDR-7 expression or activity, by administering to the subject a DHDR-7 or an agent which modulates DHDR-7 expression or at least one DHDR-7 activity. Subjects at risk for a disease which is caused or contributed to by aberrant or unwanted DHDR-7 expression or activity can be identified by, for example, any or a combination of diagnostic or prognostic assays as described herein. Administration of a prophylactic agent can occur prior to the manifestation of symptoms characteristic of the DHDR-7 aberrancy, such that a disease or disorder is prevented or, alternatively, delayed in its progression. Depending on the type of DHDR-7 aberrancy, for example, a DHDR-7, DHDR-7 agonist or DHDR-7 antagonist agent can be used for treating the subject. The appropriate agent can be determined based on screening assays described herein.

2. Therapeutic Methods

Another aspect of the invention pertains to methods of modulating DHDR-7 expression or activity for therapeutic purposes. Accordingly, in an exemplary embodiment, the modulatory method of the invention involves contacting a cell capable of expressing DHDR-7 with an agent that modulates one or more of the activities of DHDR-7 polypeptide activity associated with the cell, such that DHDR-7 activity in the cell is modulated. An agent that modulates DHDR-7 polypeptide activity can be an agent as described herein, such as a nucleic acid or a polypeptide, a naturally-occurring target molecule of a DHDR-7 polypeptide (e.g., a DHDR-7 substrate), a DHDR-7 antibody, a DHDR-7 agonist or antagonist, a peptidomimetic of a DHDR-7 agonist or antagonist, or other small molecule. In one embodiment, the agent stimulates one or more DHDR-7 activities. Examples of such stimulatory agents include active DHDR-7 polypeptide and a nucleic acid molecule encoding DHDR-7 that has been introduced into the cell. In another embodiment, the agent inhibits one or more DHDR-7 activities. Examples of such inhibitory agents include antisense DHDR-7 nucleic acid molecules, anti-DHDR-7 antibodies, and DHDR-7 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a DHDR-7 polypeptide or nucleic acid molecule. In one embodiment, the method involves administering an agent (e.g., an agent identified by a screening assay described herein), or combination of agents that modulates (e.g., upregulates or downregulates) DHDR-7 expression or activity. In another embodiment, the method involves administering a DHDR-7 polypeptide or nucleic acid molecule as therapy to compensate for reduced, aberrant, or unwanted DHDR-7 expression or activity.

Stimulation of DHDR-7 activity is desirable in situations in which DHDR-7 is abnormally downregulated and/or in which increased DHDR-7 activity is likely to have a beneficial effect. Likewise, inhibition of DHDR-7 activity is desirable in situations in which DHDR-7 is abnormally upregulated and/or in which decreased DHDR-7 activity is likely to have a beneficial effect, e.g., a decrease in energy production by tumor cells.

3. Pharmacogenomics

The DHDR-7 molecules of the present invention, as well as agents, or modulators which have a stimulatory or inhibitory effect on DHDR-7 activity (e.g., DHDR-7 gene expression) as identified by a screening assay described herein can be administered to individuals to treat (prophylactically or therapeutically) DHDR-7-associated disorders (e.g., cancer) associated with aberrant or unwanted DHDR-7 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a DHDR-7 molecule or DHDR-7 modulator as well as tailoring the dosage and/or therapeutic regimen of treatment with a DHDR-7 molecule or DHDR-7 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–1 1): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a DHDR-7 polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a DHDR-7 molecule or DHDR-7 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a DHDR-7 molecule or DHDR-7 modulator, such as a modulator identified by one of the exemplary screening assays described herein.

4. Use of DHDR-7 Molecules as Surrogate Markers

The DHDR-7 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the DHDR-7 molecules of the invention may be detected, and may be correlated with one or more biological states in vivo. For example, the DHDR-7 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The DHDR-7 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a DHDR-7 marker) transcription or expression, the amplified marker may be in a quantity which is more readily detectable than the drug itself. Also, the marker may be more easily detected due to the nature of the marker itself, for example, using the methods described herein, anti-DHDR-7 antibodies may be employed in an immune-based detection system for a DHDR-7 polypeptide marker, or DHDR-7-specific radiolabeled probes may be used to detect a DHDR-7 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3: S16–S20.

The DHDR-7 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or polypeptide (e.g., DHDR-7 polypeptide or RNA) for specific tumor markers in a subject, a drug or course of treatment may be selected that is optimized for the treatment of the specific tumor likely to be present in the subject. Similarly, the presence or absence of a specific sequence mutation in DHDR-7 DNA may correlate DHDR-7 drug response. The use of pharmacogenomic markers therefore permits the application of the most appropriate treatment for each subject without having to administer the therapy.

VI. Electronic Apparatus Readable Media and Arrays

Electronic apparatus readable media comprising DHDR-7 sequence information is also provided. As used herein, "DHDR-7 sequence information" refers to any nucleotide and/or amino acid sequence information particular to the DHDR-7 molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said DHDR-7 sequence information includes detection of the presence or absence of a sequence (e.g., detection of expression of a sequence, fragment, polymorphism, etc.), determination of the level of a sequence (e.g., detection of a level of expression, for example, a quantative detection), detection of a reactivity to a sequence (e.g., detection of protein expression and/or levels, for example, using a sequence-specific antibody), and the like. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon DHDR-7 sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the DHDR-7 sequence information.

A variety of software programs and formats can be used to store the sequence information on the electronic apparatus readable medium. For example, the sequence information can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the DHDR-7 sequence information.

By providing DHDR-7 sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a DHDR-7-associated disease or disorder or a pre-disposition to a DHDR-7-associated disease or disorder, wherein the method comprises the steps of determining DHDR-7 sequence information associated with the subject and based on the DHDR-7 sequence information, determining whether the subject has a DHDR-7-associated disease or disorder or a pre-disposition to a DHDR-7-associated disease or disorder and/or recommending a particular treatment for the disease, disorder or pre-disease condition.

The present invention further provides in an electronic system and/or in a network, a method for determining whether a subject has a DHDR-7-associated disease or disorder or a pre-disposition to a disease associated with a DHDR-7 wherein the method comprises the steps of determining DHDR-7 sequence information associated with the subject, and based on the DHDR-7 sequence information, determining whether the subject has a DHDR-7-associated disease or disorder or a pre-disposition to a DHDR-7-associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a DHDR-7-associated disease or disorder or a pre-disposition to a DHDR-7-associated disease or disorder associated with DHDR-7, said method comprising the steps of receiving DHDR-7 sequence information from the subject and/or information related thereto, receiving phenotypic information associated with the subject, acquiring information from the network corresponding to DHDR-7 and/or a DHDR-7-associated disease or disorder, and based on one or more of the phenotypic information, the DHDR-7 information (e.g., sequence information and/or information related thereto), and the acquired information, determining whether the subject has a DHDR-7-associated disease or disorder or a pre-disposition to a DHDR-7-associated disease or disorder. The method may further comprise the step of recommending a particular treatment for the disease, disorder or pre-disease condition.

The present invention also provides a business method for determining whether a subject has a DHDR-7-associated disease or disorder or a pre-disposition to a DHDR-7-associated disease or disorder, said method comprising the steps of receiving information related to DHDR-7 (e.g., sequence information and/or information related thereto), receiving phenotypic information associated with the subject, acquiring information from the network related to DHDR-7 and/or related to a DHDR-7-associated disease or disorder, and based on one or more of the phenotypic information, the DHDR-7 information, and the acquired information, determining whether the subject has a DHDR-7-associated disease or disorder or a pre-disposition to a DHDR-7-associated disease or disorder. The method may further comprise the step of recommending a particular treatment for the disease, disorder or pre-disease condition.

The invention also includes an array comprising a DHDR-7 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be DHDR-7. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a DHDR-7-associated disease or disorder, progression of DHDR-7-associated disease or disorder, and processes, such a cellular transformation associated with the DHDR-7-associated disease or disorder.

The array is also useful for ascertaining the effect of the expression of a gene on the expression of other genes in the same cell or in different cells (e.g., ascertaining the effect of DHDR-7 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including DHDR-7) that could serve as a molecular target for diagnosis or therapeutic intervention.

This invention is further illustrated by the following examples which should not be construed as limiting. The contents of all references, patents and published patent applications cited throughout this application, as well as the Figures, and Sequence Listing are incorporated herein by reference.

EXAMPLES

Example 1

Identification and Characterization of Human DHDR-7 cDNA

In this example, the identification and characterization of the gene encoding human DHDR-7 (clone Fbh62112) is described.

Isolation of the Human DHDR-7 cDNA

The invention is based, at least in part, on the discovery of a human gene encoding a novel polypeptide, referred to herein as human DHDR-7. The entire sequence of the human clone Fbh62112 was determined and found to contain an open reading frame termed human "DHDR-7." The nucleotide sequence of the human DHDR-7 gene is set forth in FIG. 1 and in the Sequence Listing as SEQ ID NO:1. The amino acid sequence of the human DHDR-7 expression product is set forth in FIG. 1 and in the Sequence Listing as SEQ ID NO:2. The DHDR-7 polypeptide comprises about 621 amino acids. The coding region (open reading frame) of SEQ ID NO:1 is set forth as SEQ ID NO:3. Clone Fbh62112FL, comprising the coding region of human DHDR-7, was deposited with the American Type Culture Collection (ATCC®), 10801 University Boulevard, Manassas, Va. 20110-2209, on Jun. 7, 2001, and assigned Accession No. PTA-3439.

Analysis of the Human DHDR-7 Molecules

A search using the polypeptide sequence of SEQ ID NO:2 was performed against the HMM database in PFAM (FIG. 2) resulting in the identification of a potential acyl-CoA dehydrogenase domain in the amino acid sequence of human DHDR-7 at about residues 85–438 of SEQ ID NO:2, a potential acyl-CoA dehydrogenase middle domain in the amino acid sequence of human DHDR-7 at about residues 85–177 of SEQ ID NO:2, a potential acyl-CoA dehydrogenase C-terminal domain in the amino acid sequence of human DHDR-7 at about residues 179–286 of SEQ ID NO:2, a potential acyl-CoA dehydrogenase N-terminal domain in the amino acid sequence of human DHDR-7 at about residues 290–441 of SEQ ID NO:2, and a potential polysaccharide deacetylase domain at about residues 432–580 of SEQ ID NO:2.

The amino acid sequence of human DHDR-7 was analyzed using the program PSORT to predict the localization of the protein within the cell. This program assesses the presence of different targeting and localization amino acid sequences within the query sequence. The results of this analysis show that human DHDR-7 may be localized to the mitochondria, the cytoplasm, and the nucleus.

Searches of the amino acid sequence of human DHDR-7 were further performed against the Prosite database. These searches resulted in the identification in the amino acid sequence of human DHDR-7 of a potential N-glycosylation site at about residues 208–211 of SEQ ID NO:2, a potential glycosaminoglycan attachment site at about residues 2–5 of SEQ ID NO:2, two potential cAMP and cGMP-dependent protein kinase phosphorylation sites at about residues 334–337 and 559–602 of SEQ ID NO:2, a number of potential protein kinase C phosphorylation sites at about residues 84–86, 191–193, 237–239, 302–304, 328–330, 449–451, and 553–555 of SEQ ID NO:2, a number of potential casein kinase II phosphorylation sites at about residues 60–63, 185–188, 197–200, 237–240, 462–465, 493–496, 522–525, and 584–587 of SEQ ID NO:2, a potential tyrosine kinase phosphorylation site at about residues 500–506 of SEQ ID NO:2, a number of potential N-myristoylation sites at about residues 19–24, 117–122, 152–157, 186–191, 217–222, 252–257, 264–269, 308–313, 403–408, 440–445, and 482–487 of SEQ ID NO:2, a potential acyl-Co-A dehydrogenase signature 1 at about residues 179–191 of SEQ ID NO:2, a potential acyl Co-A dehydrogenase signature 2 at about residues 399–418 of SEQ ID NO:2, a potential sugar transport protein signature 1 at about residues 460–476 of SEQ ID NO:2, and a potential amidation site at about residues 567–470 of SEQ ID NO:2.

A search of the amino acid sequence of human DHDR-7 was also performed against the ProDom database. These searches resulted in the identification of a "similar dehydrogenase domain" at about amino acid residues 1–36, a "dehydrogenase precursor domain" at about amino acid residues 23–123, an "acyl-coA very-long chain dehydrogenase domain" at about amino acid residues 37–426, a "dehydrogenase-related long acyl-coA chain oxidoreductase domain" at about amino acid residues 70–432, a "short-chain related acyl-coA dehydrogenase specific domain" at about amino acid residues 74–448, an "ACD-3 acyl-coA dehydrogenase domain" at about amino acid residues 147–431, an "oxidoreductase acyl-coA dehydrogenase family domain" at about amino acid residues 172–549, an "acyl-coA oxidase dehydrogenase oxidoreductase flavoprotein domain" at about amino acid residues 207–604, a "dehydrogenasr butyryl domain" at about amino acid residues 408–611, and a "very-long chain dehydrogenase doamin" at about amino acid residues 438–621 in the amino acid protein sequence of DHDR-7 (SEQ ID NO:2).

Tissue Distribution of Human DHDR-7 mRNA by Northern Analysis

This example describes the tissue distribution of DHDR-7 mRNA, as determined by Northern blot analysis.

Northern blot hybridizations with the various RNA samples are performed under standard conditions and washed under stringent conditions, i.e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations.

Tissue Distribution of Human DHDR-7 by In Situ Analysis

For in situ analysis, various tissues, e.g., tissues obtained from normal colon, breast, lung, and ovarian normal tissue, as well as colon, breast, lung, and ovarian tumors and colon metastases to the liver, were first frozen on dry ice. Ten-micrometer-thick sections of the tissues were post-fixed with 4% formaldehyde in DEPC treated IX phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0;15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5 \times 10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 kg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

In situ hybridization results indicated expression in all tumor types, with no expression in normal tissue counterparts. Expression was detected in 3 out of 4 breast tumors, 4 out of 4 lung tumors, 3 out of 3 colon tumors (including 2 primary tumors and 1 colon metastasis to the liver), and 1 out of 1 ovary tumor tested. Results are indicated in Table 1, below.

TABLE 1

In Situ Hybridization Expression Pattern of DHDR-7 mRNA in Tumor and Normal Tissue

| Specimen # | Tissue | Diagnosis | Results |
|---|---|---|---|
| BREAST: 0/1 normal; 1/1 hyperplasia; 3/4 tumors | | | |
| NDR 137 | breast | hyperplasia and normal | normal (−) hyperplasia: (+/−) |
| NDR 6 | breast | tumor: IDC | (+) |
| NDR 7 | breast | tumor: IDC | (−) |
| NDR 19 | breast | tumor: IDC | (++) |
| NUR 16 | breast | tumor: IDC | (+) |
| LUNG: 0/2 normals; 4/4 tumors | | | |
| CHT 816 | lung | normal | (−) |
| CHT 446 | lung | tumor: WD-AC | (+/−) |
| CHT 799 | lung | tumor: PD-NSCCL and normal | normal: (−) tumor: (+++) |
| CHT 800 | lung | tumor: PD-NSCCL (SCC) | (+++) |
| MPI215 | lung | tumor: small cell | (+++) |
| COLON: 0/3 normals; 2/2 primary tumors; 1/1 metastasis | | | |
| CHT 844 | colon | normal | (−) |
| NDR 99 | colon | tumor and normal | normal: (−) tumor: +/− |
| CHT 372 | colon | tumor and normal | normal: (−) tumor: +/+++ |
| CHT 72 | colon | liver metastasis | (+++/+) |
| OVARY: 0/2 normals; 1/1 tumor | | | |
| MDA 203 | ovary | normal | (−) |
| MDA 197 | ovary | normal | (−) |
| MDA 300 | ovary | tumor: MD-AC (endometriosis) | (++) |

Abbreviations; AC = adenocarcinoma; SCC = squamous cell carcinoma; NSCCL-nonsmall cell carcinoma of the lung; WD, MD, PD = well, moderate, and poorly differentiated tumors, respectively.

Figure 3B:
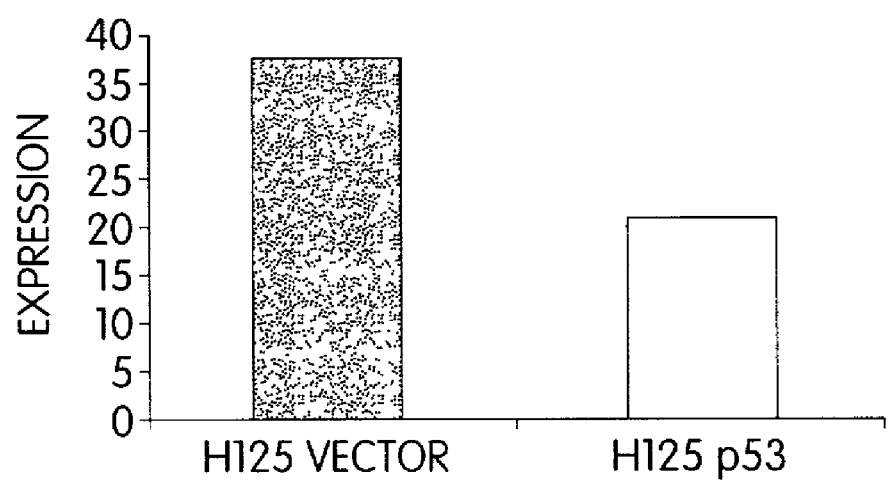
FIG. 3B is a graph showing reduced expression of DHDR-7 in NCI-H125 lung tumor cells expressing the p53 tumor suppressor gene (H125 p53) as compared to a vector only control (H125 vector), as determined by Taqman™ expression analysis.

Tissue Distribution Analysis of Human DHDR-7 mRNA Using Transcriptional Profiling DHDR-7 was identified in a transcription profiling experiment comparing gene expression patterns in the NCI-H125 lung tumor cell line with and without functional p53 expression. A 30K array was profiled with probes generated from NCI-H125 cells transiently expressing p53 and those infected with a control vector. This experiment revealed that the cells expressing p53 showed reduced levels of DHDR-7 expression as compared to the vector controls (H125 control vector) (see FIG. 3A). These results were confirmed in a Taqman™ experiment, described below. Results from the Taqman™ experiment are presented in FIG. 3B.

DHDR-7 was also expressed at higher levels when comparing breast epithelial MCF10AT3B clones with high plating efficiencies in soft agar versus clones with low plate efficiencies in soft agar. Probes were made from the following: nontransformed MCF10A cells, transformed MCF10AT3B nonclonal pool of cells, and six clonal MCF10AT3B cell lines. The cloning efficiency of the MCF10AT3B clones in soft agar ranks MCF10AT3B.c15>.c16>.c13>.c11>.c14>.c12.

Figure 4:
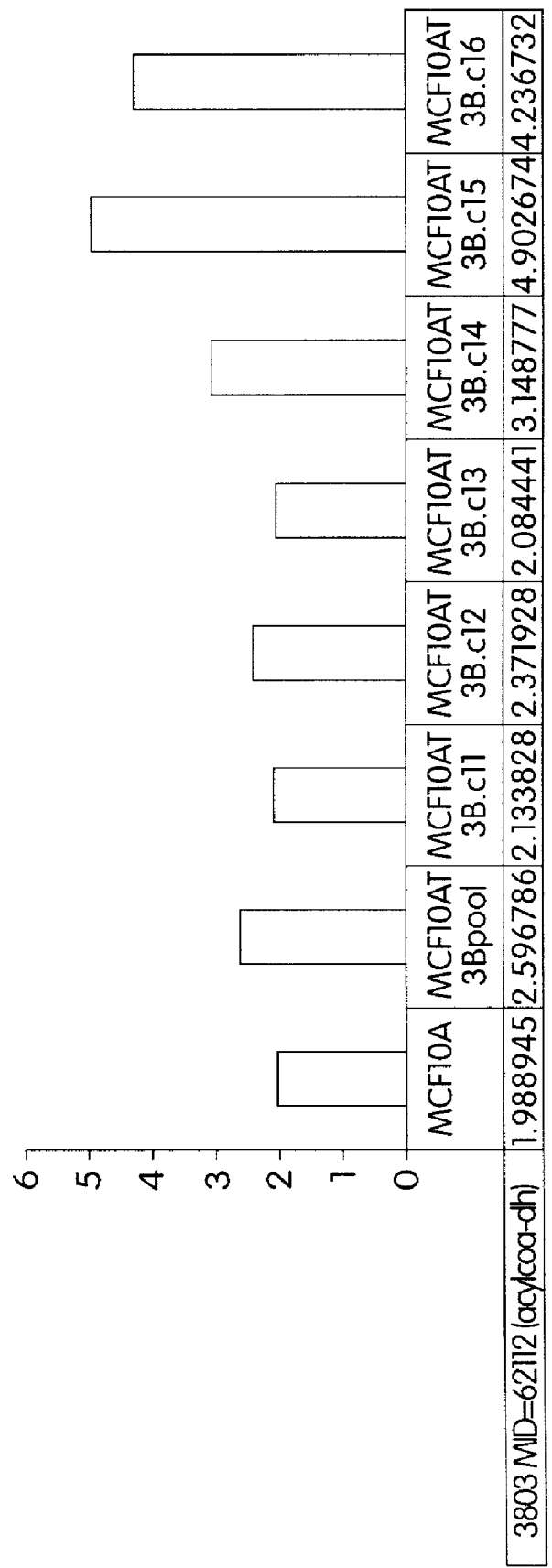
FIG. 4 is a graphical representation of median-normalized intensity values for DHDR-7 in breast epithelial MCF10A, MCF10AT3B pool and MCF10AT3B clones. The intensity value for DHDR-7 was highest in the MCF10AT3B.c15 clone, which had the highest plating efficiency in soft agar.

Results indicated that DHDR-7 was expressed at the highest level in MCF10AT3B.c15 and MCF10AT3B.c16, the two clones which plated best in soft agar (see FIG. 4).

Tissue Distribution of Human DHDR-7 mRNA Using Taqman™ Analysis

This example describes the tissue distribution of human DHDR-7 mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., lung, ovary, colon, and breast normal and tumor samples, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

These data reveal a significant up-regulation of DHDR-7 mRNA in tumors (T), breast, lung, and colon tumors in particular, as compared to respective normal (N) tissues (see Table 2, below). Given that the MRNA for DHDR-7 is expressed in a variety of tumors, with significant up-regulation in tumor samples in comparison to normal samples, it is believed that inhibition of DHDR-7 activity may inhibit tumor progression by, for example, inhibiting energy production and cellular growth and proliferation.

TABLE 2

Expression Values of DHDR-7 mRNA For Carcinoma Panel Using Taqman™ Analysis

| TISSUE TYPE | Average DHDR-7 | Average Beta 2 | Relative Expression |
|---|---|---|---|
| PIT 400 Breast N | 28.14 | 19.19 | 2.02 |
| PIT 56 Breast N | 32.42 | 22.87 | 1.33 |
| MDA 106 Breast T | 27.53 | 21.18 | 12.26 |
| MDA 234 Breast T | 28.04 | 18.30 | 1.17 |
| NDR 57 Breast T | 29.09 | 19.30 | 1.13 |
| MDA 304 Breast T | 30.07 | 19.54 | 0.68 |
| NDR 58 Breast T | 25.92 | 18.11 | 4.44 |
| NDR 132 Breast T | 27.86 | 21.77 | 14.68 |
| NDR 07 Breast T | 31.49 | 19.40 | 0.23 |
| NDR 12 Breast T | 27.94 | 22.25 | 19.30 |

TABLE 2-continued

Expression Values of DHDR-7 mRNA For Carcinoma Panel Using Taqman™ Analysis

| TISSUE TYPE | Average DHDR-7 | Average Beta 2 | Relative Expression |
|---|---|---|---|
| PIT 208 Ovary N | 26.27 | 19.29 | 7.89 |
| CHT 620 Ovary N | 28.32 | 20.04 | 3.21 |
| CHT 619 Ovary N | 27.30 | 19.88 | 5.82 |
| CHT 03 Ovary T | 30.51 | 20.15 | 0.76 |
| CLN 05 Ovary T | 29.70 | 19.16 | 0.67 |
| CLN 17 Ovary T | 26.26 | 20.26 | 15.63 |
| CLN 07 Ovary T | 29.69 | 19.53 | 0.88 |
| CLN 08 Ovary T | 30.14 | 19.12 | 0.48 |
| MDA 216 Ovary T | 31.30 | 21.03 | 0.81 |
| CLN 012 Ovary T | 27.61 | 21.29 | 12.52 |
| MDA 25 Ovary T | 27.86 | 22.09 | 18.39 |
| MDA 183 Lung N | 31.55 | 18.42 | 0.11 |
| CLN 930 Lung N | 33.19 | 21.08 | 0.23 |
| MDA 185 Lung N | 32.51 | 20.12 | 0.19 |
| CHT 816 Lung N | 33.80 | 19.57 | 0.05 |
| MPI215 Lung T SmC | 26.14 | 19.45 | 9.72 |
| MDA 259 Lung T-PDNSCCL | 24.40 | 19.71 | 38.88 |
| CHT 832 Lung T-PDNSCCL | 28.45 | 18.87 | 1.31 |
| MDA 253 Lung T-PDNSCCL | 27.73 | 18.60 | 1.79 |
| CHT 814 Lung T-SCC | 23.37 | 16.93 | 11.56 |
| CHT 911 Lung T-SCC | 26.22 | 19.66 | 10.56 |
| CHT 726 Lung T-SCC | 26.13 | 17.92 | 3.38 |
| CHT 845 Lung T-AC | 27.13 | 20.81 | 12.56 |
| NHBE | 25.58 | 20.29 | 25.56 |
| H125 p53 | 26.99 | 21.40 | 20.76 |
| H125 VC | 26.15 | 21.40 | 37.16 |
| CHT 396 Colon N | 31.82 | 19.18 | 0.16 |
| CHT 519 Colon N | 33.48 | 20.38 | 0.11 |
| CHT 416 Colon N | 31.59 | 20.4 | 0.43 |
| CHT 452 Colon N | 32.74 | 19.05 | 0.08 |
| CHT 398 Colon T | 26.43 | 19.91 | 10.90 |
| CHT 807 Colon T | 28.45 | 17.07 | 0.38 |
| CHT 528 Colon T | 26.27 | 19.36 | 8.37 |
| CHT 368 Colon T | 25.63 | 18.14 | 5.54 |
| CHT 372 Colon T | 29.69 | 20.18 | 1.37 |
| CHT 01 Liver Met | 28.67 | 18.32 | 0.77 |
| CHT 3 Liver Met | 28.52 | 20.97 | 5.34 |
| CHT 896 Liver Met | 28.59 | 19.62 | 1.99 |
| NDR 217 Liver Met | 28.7 | 19.48 | 1.68 |
| PIT 260 Liver N | 28.32 | 18.18 | 0.89 |
| PIT 229 Liver N | 31.57 | 25.02 | 10.67 |
| MGH 16 Brain N | 30.62 | 24.59 | 15.36 |
| MCL 53 Brain N | 28.34 | 24.11 | 53.29 |
| MCL 377 Brain N | 30.36 | 25.18 | 22.96 |
| MCL 390 Brain N | 28.2 | 23.7 | 43.89 |
| Astrocytes | 25.81 | 20.57 | 26.55 |
| CHT 201 Brain T | 33.35 | 21.23 | 0.22 |
| CHT 216 Brain T | 26.33 | 17.29 | 1.90 |
| CHT 501 Brain T | 29.28 | 21.07 | 3.37 |
| CHT 1273 Brain T | 26.75 | 21.95 | 35.90 |
| A24 HMVEC-Arr | 25.54 | 18.75 | 9.10 |
| C48 HMVEC-Prol | 26.59 | 21.03 | 21.27 |
| CHT 50 Placenta | 33.84 | 25.2 | 2.51 |
| BWH 54 Fetal Liver | 26.75 | 22.52 | 53.47 |
| BWH 75 Fetal Liver | 26.06 | 20.31 | 18.58 |
| CHT 765 Wilms T | 27.95 | 23.79 | 56.13 |
| PIT 213 Renal T | 39.34 | 24.95 | 0.00 |
| CBT 1424 Endometrial AC | 31.28 | 23.38 | 4.17 |

T = tumor, N = normal tissue, met = colon metastases to the liver.

A second panel was also tested (the Phase I Panel), revealing highest expression in normal brain cortex and HUVECs, as shown in Table 3, below.

TABLE 3

Expression Values of DHDR-7 mRNA For Phase I Panel Using Taqman™ Analysis

| Tissue Type | Average DHDR-7 | Average β2 | Relative Expression |
|---|---|---|---|
| Artery Normal | 30.43 | 22.23 | 3.40 |
| Vein normal | 30.65 | 20.68 | 1.00 |
| Aortic SMC EARLY | 28.2 | 22.09 | 14.43 |
| Coronary SMC | 28.59 | 23.14 | 22.96 |
| Static HUVEC | 25.5 | 20.95 | 42.99 |
| Shear HUVEC | 26.36 | 21.27 | 29.36 |
| Heart normal | 26.48 | 19.36 | 7.16 |
| Heart CHF | 25.27 | 19.7 | 20.91 |
| Kidney | 26.93 | 20.8 | 14.28 |
| Skeletal Muscle | 28.79 | 22.2 | 10.42 |
| Adipose normal | 26.86 | 19.86 | 7.81 |
| Pancreas | 28.34 | 22.11 | 13.28 |
| Primary osteoblasts | 27.05 | 19.97 | 7.39 |
| Osteoclasts (diff) | 30.91 | 17.99 | 0.13 |
| Skin normal | 29.33 | 21.36 | 3.97 |
| Spinal cord normal | 28.23 | 20.13 | 3.62 |
| Brain Cortex normal | 25.59 | 21.57 | 61.43 |
| Brain Hypothalamus norm. | 27.71 | 21.6 | 14.48 |
| Nerve | 32.77 | 24.16 | 2.55 |
| ORG | 28.3 | 22.2 | 14.63 |
| Glial Cells (Astrocytes) | 27.69 | 22.61 | 29.67 |
| Glioblastoma | 26.39 | 18.24 | 3.53 |
| Breast normal | 28.41 | 20.77 | 5.01 |
| Breast tumor | 26.15 | 18.82 | 6.19 |
| Ovary normal | 27.41 | 20.73 | 9.79 |
| Ovary Tumor | 30.67 | 20.5 | 0.87 |
| Prostate Normal | 27.48 | 19.74 | 4.68 |
| Prostate Tumor | 26.02 | 18.21 | 4.47 |
| Epithelial cells (Prostate) | 27.06 | 21.4 | 19.71 |
| Colon Tumor | 26.41 | 19.55 | 8.61 |
| Lung normal | 30.48 | 18.86 | 0.32 |
| Lung tumor | 26.02 | 18.65 | 6.02 |
| Lung COPD | 28.25 | 18.74 | 1.37 |
| Colon IBO | 30.3 | 18.41 | 0.27 |
| Liver normal | 28.2 | 20.38 | 4.41 |
| Liver fibrosis | 28.78 | 22.18 | 10.31 |
| Dermal Cells - fibroblasts | 28.18 | 21.17 | 7.79 |
| Spleen normal | 29.88 | 19.91 | 1.00 |
| Tonsil normal | 26.06 | 17.55 | 2.75 |
| Lymph node | 28.79 | 18.92 | 1.07 |
| Small Intestine | 30.38 | 20.04 | 0.77 |
| Skin-Decubitus | 29.68 | 21.11 | 2.63 |
| Synovium | 32.16 | 20.88 | 0.40 |
| BM-MNC (Bone marrow mononuclear cells) | 25.98 | 17.22 | 2.30 |
| Activated PBMC | 32.51 | 16.98 | 0.02 |
| Colon Normal | 31.78 | 19.52 | .2039 |

A further experiment revealed that DHDR-7 mRNA is also expressed at high levels in most of the xenograft-friendly cell lines tested using Taqman™ analysis (see Table 4, below).

TABLE 4

Expression Values of DHDR-7 mRNA for Xenograft Cell Lines Using Taqman™ Analysis

| Tissue Type | Average DHDR-7 | Average β2 | Relative Expression |
|---|---|---|---|
| MCF-7 Breast Tumor | 21.50 | 19.38 | 230.05 |
| ZR75 Breast Tumor | 22.30 | 19.05 | 105.48 |
| T47D Breast Tumor | 21.20 | 18.77 | 184.92 |
| MDA 231 Breast Tumor | 22.48 | 18.20 | 51.47 |
| MDA 435 Breast Tumor | 21.45 | 17.10 | 49.04 |
| SKBr3 | 25.79 | 22.63 | 111.88 |
| DLD 1 Colon Tumor (stage C) | 22.32 | 20.10 | 215.39 |
| SW 620 | 21.38 | 18.83 | 170.76 |
| HCT116 | 22.20 | 18.97 | 106.58 |

TABLE 4-continued

Expression Values of DHDR-7 mRNA for Xenograft Cell Lines Using Taqman™ Analysis

| Tissue Type | Average DHDR-7 | Average β2 | Relative Expression |
|---|---|---|---|
| HT29 | 22.05 | 16.90 | 28.16 |
| Colo 205 | 21.25 | 15.81 | 22.96 |
| NCIH125 | 21.43 | 18.15 | 102.59 |
| NCIH69 | 21.49 | 18.68 | 142.60 |
| NCIH322 | 22.25 | 18.98 | 103.66 |
| NCIH460 | 22.16 | 18.41 | 74.58 |
| A549 | 22.41 | 19.41 | 125.43 |
| NHBE | 24.27 | 19.51 | 37.03 |
| SKOV-3 ovary | 23.33 | 18.04 | 25.56 |
| OVCAR-3 ovary | 23.42 | 20.94 | 179.24 |
| 293 | 23.22 | 21.17 | 242.32 |
| 293T | 23.49 | 22.75 | 598.74 |

Example 2

Expression of Recombinant DHDR-7 Polypeptide in Bacterial Cells

In this example, human DHDR-7 is expressed as a recombinant glutathione-S-transferase (GST) fusion polypeptide in E. coli and the fusion polypeptide is isolated and characterized. Specifically, DHDR-7 is fused to GST and this fusion polypeptide is expressed in E. coli, e.g., strain PEB 199. Expression of the GST-DHDR-7 fusion polypeptide in PEB 199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant DHDR-7 Polypeptide in Cos Cells

To express the human DHDR-7 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire DHDR-7 polypeptide and an HA tag (Wilson et al. (1984) Cell 37:767) or a FLAG tag fused in-frame to its 3' end of the fragment is cloned into the polylinker region of the vector, thereby placing the expression of the recombinant polypeptide under the control of the CMV promoter.

To construct the plasmid, the human DHDR-7 DNA sequence is amplified by PCR using two primers. The 5' primer contains the restriction site of interest followed by approximately twenty nucleotides of the DHDR-7 coding sequence starting from the initiation codon; the 3' end sequence contains complementary sequences to the other restriction site of interest, a translation stop codon, the HA tag or FLAG tag and the last 20 nucleotides of the DHDR-7 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the DHDR-7 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the human DHDR-7-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989. The expression of the IC54420 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the human DHDR-7 coding sequence is cloned directly into the polylinker of the pCDNA/Amp vector using the appropriate restriction sites. The resulting plasmid is transfected into COS cells in the manner described above, and the expression of the DHDR-7 polypeptide is detected by radiolabelling and immunoprecipitation using a DHDR-7-specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for identifying a candidate compound which binds to a polypeptide selected from the group consisting of:
   a) a polypeptide comprising the amino acid sequence of SEQ ID NO:2;
   b) a polypeptide comprising the amino acid sequence encoded by the cDNA insert of the plasmid deposited with ATCC as Patent Deposit Number PTA-3439; and
   c) a polypeptide encoded by the nucleotide sequence set forth in SEQ ID NO:1 or SEQ ID NQ:3; wherein the compound is capable of modulating cellular growth or proliferation of cancer cells in vitro, the method comprising:
      i) contacting a sample comprising the polypeptide with a test compound under conditions suitable for binding;
      ii) detecting binding of the test compound to the polypeptide to identify a test compound that binds to the polypeptide;
      iii) incubating the test compound which binds to the polypeptide with cancer cells; and
      iv) determining whether the test compound modulates cellular growth or proliferation of the cancer cells;
   thereby identifying a candidate compound capable of modulating cellular growth or proliferation of cancer cells in vitro.

2. The method of claim 1, wherein the polypeptide comprises the amino acid sequence of SEQ ID NO:2.

3. The method of claim 1, wherein the polypeptide is encoded by the nucleotide sequence set forth in SEQ ID NO:1 or SEQ ID NO:3.

4. The method of claim 1, wherein the polypeptide further comprises heterologous sequences.

5. The method of claim 1, wherein the sample is an isolated polypeptide or a cell comprising the polypeptide.

6. The method of claim 5, wherein the cell is a mammalian cell.

7. The method of claim 1, wherein the compound is a small molecule.

8. The method of claim 1, wherein the cancer cells are selected from the group consisting of lung cancer cells, breast cancer cells, ovarian cancer cells and colon cancer cells.

9. The method of claim 1, wherein the binding of the test compound to the polypeptide is detected by a method selected from the group consisting of:
   a) direct detecting of test compound/polypeptide binding;
   b) a competition binding assay;
   c) an immunoassay; and
   d) a yeast two-hybrid assay.

* * * * *

UNITED STATES PATENT AND TRADEMARK OFFICE
CERTIFICATE OF CORRECTION

PATENT NO. : 7,166,428 B2
APPLICATION NO. : 09/945326
DATED : January 23, 2007
INVENTOR(S) : Rachel E. Meyers et al.

It is certified that error appears in the above-identified patent and that said Letters Patent is hereby corrected as shown below:

Column 91, line 31, immediately following "cellular growth or proliferation of the cancer cells," the following phrase --in vitro-- should be inserted.

Signed and Sealed this

Nineteenth Day of June, 2007

JON W. DUDAS
*Director of the United States Patent and Trademark Office*

UNITED STATES PATENT AND TRADEMARK OFFICE
CERTIFICATE OF CORRECTION

PATENT NO. : 7,166,428 B2
APPLICATION NO. : 09/945326
DATED : January 23, 2007
INVENTOR(S) : Rachel E. Meyers et al.

It is certified that error appears in the above-identified patent and that said Letters Patent is hereby corrected as shown below:

Column 91, line 31, immediately following "cellular growth or proliferation of the cancer cells," the following phrase --in vitro-- should be inserted.

Signed and Sealed this

Seventeenth Day of July, 2007

JON W. DUDAS
*Director of the United States Patent and Trademark Office*

SEQUENCE LISTING

<160> NUMBER OF SEQ ID NOS: 3

<210> SEQ ID NO 1
<211> LENGTH: 2452

-continued

```
<212> TYPE: DNA
<213> ORGANISM: Homo sapiens
<220> FEATURE:
<221> NAME/KEY: CDS
<222> LOCATION: (67)...(1932)

<400> SEQUENCE: 1
cgtgtgtgtg tccctgcggc gctaagaagg ggagactgag gctgaggctg gggaacatcg         60 ggcagc atg agc ggc tgc ggg ctc ttc ctg cgc acc acg gct gcg gct          108
       Met Ser Gly Cys Gly Leu Phe Leu Arg Thr Thr Ala Ala Ala
        1               5                  10 cgt gcc tgc cgg ggt ctg gtg gtc tct acc gcg aac cgg cgg cta ctg         156
Arg Ala Cys Arg Gly Leu Val Val Ser Thr Ala Asn Arg Arg Leu Leu
 15                  20                  25                  30 cgc acc agc ccg cct gta cga gct ttc gcc aaa gag ctt ttc cta ggc         204
Arg Thr Ser Pro Pro Val Arg Ala Phe Ala Lys Glu Leu Phe Leu Gly
                 35                  40                  45 aaa atc aag aag aaa gaa gtt ttc cca ttt cca gaa gtt agc caa gat         252
Lys Ile Lys Lys Lys Glu Val Phe Pro Phe Pro Glu Val Ser Gln Asp
             50                  55                  60 gaa ctt aat gaa atc aat cag ttc ttg gga ccc gtg gaa aaa ttc ttc         300
Glu Leu Asn Glu Ile Asn Gln Phe Leu Gly Pro Val Glu Lys Phe Phe
 65                  70                  75 act gaa gag gtg gac tcc cga aaa att gac cag gaa ggg aaa atc cca         348
Thr Glu Glu Val Asp Ser Arg Lys Ile Asp Gln Glu Gly Lys Ile Pro
     80                  85                  90 gat gaa act ttg gag aaa ttg aag agc cta ggg ctt ttt ggg ctg caa         396
Asp Glu Thr Leu Glu Lys Leu Lys Ser Leu Gly Leu Phe Gly Leu Gln
 95                 100                 105                 110 gtc cca gaa gaa tat ggt ggc ctg ggc ttc tcc aac acc atg tac tca         444
Val Pro Glu Glu Tyr Gly Gly Leu Gly Phe Ser Asn Thr Met Tyr Ser
                115                 120                 125 aga cta ggg gag atc atc agc atg gat ggg tcc atc act gtg acc ctg         492
Arg Leu Gly Glu Ile Ile Ser Met Asp Gly Ser Ile Thr Val Thr Leu
            130                 135                 140 gca gcg cac cag gct att ggc ctc aag ggg atc atc ttg gct ggc act         540
Ala Ala His Gln Ala Ile Gly Leu Lys Gly Ile Ile Leu Ala Gly Thr
        145                 150                 155 gag gag cag aaa gcc aaa tac ttg cct aaa ctg gcg tcc ggg gag cac         588
Glu Glu Gln Lys Ala Lys Tyr Leu Pro Lys Leu Ala Ser Gly Glu His
160                 165                 170 att gca gcc ttc tgc ctc acg gag cca gcc agt ggg agc gat gca gcc         636
Ile Ala Ala Phe Cys Leu Thr Glu Pro Ala Ser Gly Ser Asp Ala Ala
175                 180                 185                 190 tca atc cgg agc aga gcc aca cta agt gaa gac aag aag cac tac atc         684
Ser Ile Arg Ser Arg Ala Thr Leu Ser Glu Asp Lys Lys His Tyr Ile
                195                 200                 205 ctc aat ggc tcc aag gtc tgg att act aat gga gga ctg gcc aat att         732
Leu Asn Gly Ser Lys Val Trp Ile Thr Asn Gly Gly Leu Ala Asn Ile
            210                 215                 220 ttt act gtg ttt gca aag act gag gtc gtt gat tct gat gga tca gtg         780
Phe Thr Val Phe Ala Lys Thr Glu Val Val Asp Ser Asp Gly Ser Val
        225                 230                 235 aaa gac aaa atc aca gca ttc ata gta gaa aga gac ttt ggt gga gtc         828
Lys Asp Lys Ile Thr Ala Phe Ile Val Glu Arg Asp Phe Gly Gly Val
240                 245                 250 act aat ggg aaa ccc gaa gat aaa tta ggc att cgg ggc tcc aac act         876
Thr Asn Gly Lys Pro Glu Asp Lys Leu Gly Ile Arg Gly Ser Asn Thr
255                 260                 265                 270 tgt gaa gtc cat ttt gaa aac acc aag ata cct gtg gaa aac atc ctt         924
```

-continued

| | | |
|---|---|---|
| Cys Glu Val His Phe Glu Asn Thr Lys Ile Pro Val Glu Asn Ile Leu<br>275 280 285 | | |
| gga gag gtc gga gat ggg ttt aag gtg gcc atg aac atc ctc aac agc<br>Gly Glu Val Gly Asp Gly Phe Lys Val Ala Met Asn Ile Leu Asn Ser<br>290 295 300 | 972 | |
| ggc cgg ttc agc atg ggc agc gtc gtg gct ggg ctg ctc aag aga ttg<br>Gly Arg Phe Ser Met Gly Ser Val Val Ala Gly Leu Leu Lys Arg Leu<br>305 310 315 | 1020 | |
| att gaa atg act gct gag tac gcc tgc aca agg aaa cag ttt aac aag<br>Ile Glu Met Thr Ala Glu Tyr Ala Cys Thr Arg Lys Gln Phe Asn Lys<br>320 325 330 | 1068 | |
| agg ctc agt gaa ttt gga ttg att cag gag aaa ttt gca ctg atg gct<br>Arg Leu Ser Glu Phe Gly Leu Ile Gln Glu Lys Phe Ala Leu Met Ala<br>335 340 345 350 | 1116 | |
| cag aag gct tac gtc atg gag agt atg acc tac ctc aca gca ggg atg<br>Gln Lys Ala Tyr Val Met Glu Ser Met Thr Tyr Leu Thr Ala Gly Met<br>355 360 365 | 1164 | |
| ctg gac caa cct ggc ttt ccc gac tgc tcc atc gag gca gcc atg gtg<br>Leu Asp Gln Pro Gly Phe Pro Asp Cys Ser Ile Glu Ala Ala Met Val<br>370 375 380 | 1212 | |
| aag gtg ttc agc tcc gag gcc gcc tgg cag tgt gtg agt gag gcg ctg<br>Lys Val Phe Ser Ser Glu Ala Ala Trp Gln Cys Val Ser Glu Ala Leu<br>385 390 395 | 1260 | |
| cag atc ctc ggg ggc ttg ggc tac aca agg gac tat ccg tac gag cgc<br>Gln Ile Leu Gly Gly Leu Gly Tyr Thr Arg Asp Tyr Pro Tyr Glu Arg<br>400 405 410 | 1308 | |
| ata ctg cgt gac acc cgc atc ctc ctc atc ttc gag gga acc aat gag<br>Ile Leu Arg Asp Thr Arg Ile Leu Leu Ile Phe Glu Gly Thr Asn Glu<br>415 420 425 430 | 1356 | |
| att ctc cgg atg tac atc gcc ctg acg ggt ctg cag cat gcc ggc cgc<br>Ile Leu Arg Met Tyr Ile Ala Leu Thr Gly Leu Gln His Ala Gly Arg<br>435 440 445 | 1404 | |
| atc ctg act acc agg atc cat gag ctt aaa cag gcc aaa gtg agc aca<br>Ile Leu Thr Thr Arg Ile His Glu Leu Lys Gln Ala Lys Val Ser Thr<br>450 455 460 | 1452 | |
| gtc atg gat acc gtt ggc cgg agg ctt cgg gac tcc ctg ggc cga act<br>Val Met Asp Thr Val Gly Arg Arg Leu Arg Asp Ser Leu Gly Arg Thr<br>465 470 475 | 1500 | |
| gtg gac ctg ggg ctg aca ggc aac cat gga gtt gtg cac ccc agt ctt<br>Val Asp Leu Gly Leu Thr Gly Asn His Gly Val Val His Pro Ser Leu<br>480 485 490 | 1548 | |
| gcg gac agt gcc aac aag ttt gag gag aac acc tac tgc ttc ggc cgg<br>Ala Asp Ser Ala Asn Lys Phe Glu Glu Asn Thr Tyr Cys Phe Gly Arg<br>495 500 505 510 | 1596 | |
| acc gtg gag aca ctg ctg ctc cgc ttt ggc aag acc atc atg gag gag<br>Thr Val Glu Thr Leu Leu Leu Arg Phe Gly Lys Thr Ile Met Glu Glu<br>515 520 525 | 1644 | |
| cag ctg gta ctg aag cgg gtg gcc aac atc ctc atc aac ctg tat ggc<br>Gln Leu Val Leu Lys Arg Val Ala Asn Ile Leu Ile Asn Leu Tyr Gly<br>530 535 540 | 1692 | |
| atg acg gcc gtg ctg tcg cgg gcc agc cgc tcc atc cgc att ggg ctc<br>Met Thr Ala Val Leu Ser Arg Ala Ser Arg Ser Ile Arg Ile Gly Leu<br>545 550 555 | 1740 | |
| cgc aac cac gac cac gag gtt ctc ttg gcc aac acc ttc tgc gtg gaa<br>Arg Asn His Asp His Glu Val Leu Leu Ala Asn Thr Phe Cys Val Glu<br>560 565 570 | 1788 | |
| gct tac ttg cag aat ctc ttc agc ctc tct cag ctg gac aag tat gct<br>Ala Tyr Leu Gln Asn Leu Phe Ser Leu Ser Gln Leu Asp Lys Tyr Ala<br>575 580 585 590 | 1836 | |

```
                                                                      -continued cca gaa aac cta gat gag cag att aag aaa gtg tcc cag cag atc ctt       1884
Pro Glu Asn Leu Asp Glu Gln Ile Lys Lys Val Ser Gln Gln Ile Leu
                    595                 600                 605 gag aag cga gcc tat atc tgt gcc cac cct ctg gac agg aca tgc tga       1932
Glu Lys Arg Ala Tyr Ile Cys Ala His Pro Leu Asp Arg Thr Cys *
            610                 615                 620 ggcaggggac agtgtcccct gctaccgccc gccctaccc atggcccgtt gctggatgac      1992
tgttactctt ttttcagaag gtgttgggat tatcacaggt taagccttt gttccccgtc      2052 tgcacctgaa gggttgtcgc ctggcctggg agagcctctt ccaggttttg acctgcaggc     2112
agtgctctct aacaggacca tcacagcttc tgaactgagc cggagagaga gaatggaatt     2172
gctgacccct ggaactggcg ggtattctgg tcattgagga gacaccatag tggaaactgg     2232
ggcttatgct gctgcctcca gggtgtgagg tgggtgggga cctgtgtcag gtgtggatag     2292
ccatttctgc tcaaccacac attctctaag aaacagcttg aaagctctgt ctgggtcatt     2352
catttaaact agaagcagag gcacttaaaa catgtaccag gaaccattta acaaagaata     2412
taaaatgtca caatctgtgt actgttaaaa aaaaaaaaa                            2452

<210> SEQ ID NO 2
<211> LENGTH: 621
<212> TYPE: PRT
<213> ORGANISM: Homo sapiens

<400> SEQUENCE: 2

Met Ser Gly Cys Gly Leu Phe Leu Arg Thr Thr Ala Ala Ala Arg Ala
1               5                   10                  15

Cys Arg Gly Leu Val Val Ser Thr Ala Asn Arg Arg Leu Leu Arg Thr
            20                  25                  30

Ser Pro Pro Val Arg Ala Phe Ala Lys Glu Leu Phe Leu Gly Lys Ile
        35                  40                  45

Lys Lys Lys Glu Val Phe Pro Phe Pro Glu Val Ser Gln Asp Glu Leu
    50                  55                  60

Asn Glu Ile Asn Gln Phe Leu Gly Pro Val Glu Lys Phe Phe Thr Glu
65                  70                  75                  80

Glu Val Asp Ser Arg Lys Ile Asp Gln Glu Gly Lys Ile Pro Asp Glu
                85                  90                  95

Thr Leu Glu Lys Leu Lys Ser Leu Gly Leu Phe Gly Leu Gln Val Pro
            100                 105                 110

Glu Glu Tyr Gly Gly Leu Gly Phe Ser Asn Thr Met Tyr Ser Arg Leu
        115                 120                 125

Gly Glu Ile Ile Ser Met Asp Gly Ser Ile Thr Val Thr Leu Ala Ala
    130                 135                 140

His Gln Ala Ile Gly Leu Lys Gly Ile Ile Leu Ala Gly Thr Glu Glu
145                 150                 155                 160

Gln Lys Ala Lys Tyr Leu Pro Lys Leu Ala Ser Gly Glu His Ile Ala
                165                 170                 175

Ala Phe Cys Leu Thr Glu Pro Ala Ser Gly Ser Asp Ala Ala Ser Ile
            180                 185                 190

Arg Ser Arg Ala Thr Leu Ser Glu Asp Lys Lys His Tyr Ile Leu Asn
        195                 200                 205

Gly Ser Lys Val Trp Ile Thr Asn Gly Gly Leu Ala Asn Ile Phe Thr
    210                 215                 220

Val Phe Ala Lys Thr Glu Val Val Asp Ser Asp Gly Ser Val Lys Asp
225                 230                 235                 240
```

Lys Ile Thr Ala Phe Ile Val Glu Arg Asp Phe Gly Val Thr Asn
                245                 250                 255

Gly Lys Pro Glu Asp Lys Leu Gly Ile Arg Gly Ser Asn Thr Cys Glu
            260                 265                 270

Val His Phe Glu Asn Thr Lys Ile Pro Val Glu Asn Ile Leu Gly Glu
        275                 280                 285

Val Gly Asp Gly Phe Lys Val Ala Met Asn Ile Leu Asn Ser Gly Arg
    290                 295                 300

Phe Ser Met Gly Ser Val Val Ala Gly Leu Leu Lys Arg Leu Ile Glu
305                 310                 315                 320

Met Thr Ala Glu Tyr Ala Cys Thr Arg Lys Gln Phe Asn Lys Arg Leu
                325                 330                 335

Ser Glu Phe Gly Leu Ile Gln Glu Lys Phe Ala Leu Met Ala Gln Lys
            340                 345                 350

Ala Tyr Val Met Glu Ser Met Thr Tyr Leu Thr Ala Gly Met Leu Asp
        355                 360                 365

Gln Pro Gly Phe Pro Asp Cys Ser Ile Glu Ala Ala Met Val Lys Val
    370                 375                 380

Phe Ser Ser Glu Ala Ala Trp Gln Cys Val Ser Glu Ala Leu Gln Ile
385                 390                 395                 400

Leu Gly Gly Leu Gly Tyr Thr Arg Asp Tyr Pro Tyr Glu Arg Ile Leu
                405                 410                 415

Arg Asp Thr Arg Ile Leu Leu Ile Phe Glu Gly Thr Asn Glu Ile Leu
            420                 425                 430

Arg Met Tyr Ile Ala Leu Thr Gly Leu Gln His Ala Gly Arg Ile Leu
        435                 440                 445

Thr Thr Arg Ile His Glu Leu Lys Gln Ala Lys Val Ser Thr Val Met
    450                 455                 460

Asp Thr Val Gly Arg Arg Leu Arg Asp Ser Leu Gly Arg Thr Val Asp
465                 470                 475                 480

Leu Gly Leu Thr Gly Asn His Gly Val Val His Pro Ser Leu Ala Asp
                485                 490                 495

Ser Ala Asn Lys Phe Glu Glu Asn Thr Tyr Cys Phe Gly Arg Thr Val
            500                 505                 510

Glu Thr Leu Leu Leu Arg Phe Gly Lys Thr Ile Met Glu Glu Gln Leu
        515                 520                 525

Val Leu Lys Arg Val Ala Asn Ile Leu Ile Asn Leu Tyr Gly Met Thr
    530                 535                 540

Ala Val Leu Ser Arg Ala Ser Arg Ser Ile Arg Ile Gly Leu Arg Asn
545                 550                 555                 560

His Asp His Glu Val Leu Leu Ala Asn Thr Phe Cys Val Glu Ala Tyr
                565                 570                 575

Leu Gln Asn Leu Phe Ser Leu Ser Gln Leu Asp Lys Tyr Ala Pro Glu
            580                 585                 590

Asn Leu Asp Glu Gln Ile Lys Lys Val Ser Gln Gln Ile Leu Glu Lys
        595                 600                 605

Arg Ala Tyr Ile Cys Ala His Pro Leu Asp Arg Thr Cys
    610                 615                 620

<210> SEQ ID NO 3
<211> LENGTH: 1863
<212> TYPE: DNA
<213> ORGANISM: Homo sapiens
<220> FEATURE:
<221> NAME/KEY: CDS -continued

<222> LOCATION: (1)...(1863)

<400> SEQUENCE: 3

```
atg agc ggc tgc ggg ctc ttc ctg cgc acc acg gct gcg gct cgt gcc      48
Met Ser Gly Cys Gly Leu Phe Leu Arg Thr Thr Ala Ala Ala Arg Ala
 1               5                  10                  15 tgc cgg ggt ctg gtg gtc tct acc gcg aac cgg cgg cta ctg cgc acc      96
Cys Arg Gly Leu Val Val Ser Thr Ala Asn Arg Arg Leu Leu Arg Thr
             20                  25                  30 agc ccg cct gta cga gct ttc gcc aaa gag ctt ttc cta ggc aaa atc     144
Ser Pro Pro Val Arg Ala Phe Ala Lys Glu Leu Phe Leu Gly Lys Ile
         35                  40                  45 aag aag aaa gaa gtt ttc cca ttt cca gaa gtt agc caa gat gaa ctt     192
Lys Lys Lys Glu Val Phe Pro Phe Pro Glu Val Ser Gln Asp Glu Leu
     50                  55                  60 aat gaa atc aat cag ttc ttg gga ccc gtg gaa aaa ttc ttc act gaa     240
Asn Glu Ile Asn Gln Phe Leu Gly Pro Val Glu Lys Phe Phe Thr Glu
 65                  70                  75                  80 gag gtg gac tcc cga aaa att gac cag gaa ggg aaa atc cca gat gaa     288
Glu Val Asp Ser Arg Lys Ile Asp Gln Glu Gly Lys Ile Pro Asp Glu
                 85                  90                  95 act ttg gag aaa ttg aag agc cta ggg ctt ttt ggg ctg caa gtc cca     336
Thr Leu Glu Lys Leu Lys Ser Leu Gly Leu Phe Gly Leu Gln Val Pro
            100                 105                 110 gaa gaa tat ggt ggc ctg ggc ttc tcc aac acc atg tac tca aga cta     384
Glu Glu Tyr Gly Gly Leu Gly Phe Ser Asn Thr Met Tyr Ser Arg Leu
        115                 120                 125 ggg gag atc atc agc atg gat ggg tcc atc act gtg acc ctg gca gcg     432
Gly Glu Ile Ile Ser Met Asp Gly Ser Ile Thr Val Thr Leu Ala Ala
    130                 135                 140 cac cag gct att ggc ctc aag ggg atc atc ttg gct ggc act gag gag     480
His Gln Ala Ile Gly Leu Lys Gly Ile Ile Leu Ala Gly Thr Glu Glu
145                 150                 155                 160 cag aaa gcc aaa tac ttg cct aaa ctg gcg tcc ggg gag cac att gca     528
Gln Lys Ala Lys Tyr Leu Pro Lys Leu Ala Ser Gly Glu His Ile Ala
                165                 170                 175 gcc ttc tgc ctc acg gag cca gcc agt ggg agc gat gca gcc tca atc     576
Ala Phe Cys Leu Thr Glu Pro Ala Ser Gly Ser Asp Ala Ala Ser Ile
            180                 185                 190 cgg agc aga gcc aca cta agt gaa gac aag aag cac tac atc ctc aat     624
Arg Ser Arg Ala Thr Leu Ser Glu Asp Lys Lys His Tyr Ile Leu Asn
        195                 200                 205 ggc tcc aag gtc tgg att act aat gga gga ctg gcc aat att ttt act     672
Gly Ser Lys Val Trp Ile Thr Asn Gly Gly Leu Ala Asn Ile Phe Thr
    210                 215                 220 gtg ttt gca aag act gag gtc gtt gat tct gat gga tca gtg aaa gac     720
Val Phe Ala Lys Thr Glu Val Val Asp Ser Asp Gly Ser Val Lys Asp
225                 230                 235                 240 aaa atc aca gca ttc ata gta gaa aga gac ttt ggt gga gtc act aat     768
Lys Ile Thr Ala Phe Ile Val Glu Arg Asp Phe Gly Gly Val Thr Asn
                245                 250                 255 ggg aaa ccc gaa gat aaa tta ggc att cgg ggc tcc aac act tgt gaa     816
Gly Lys Pro Glu Asp Lys Leu Gly Ile Arg Gly Ser Asn Thr Cys Glu
            260                 265                 270 gtc cat ttt gaa aac acc aag ata cct gtg gaa aac atc ctt gga gag     864
Val His Phe Glu Asn Thr Lys Ile Pro Val Glu Asn Ile Leu Gly Glu
        275                 280                 285 gtc gga gat ggg ttt aag gtg gcc atg aac atc ctc aac agc ggc cgg     912
Val Gly Asp Gly Phe Lys Val Ala Met Asn Ile Leu Asn Ser Gly Arg
    290                 295                 300
```

-continued

| | |
|---|---|
| ttc agc atg ggc agc gtc gtg gct ggg ctg ctc aag aga ttg att gaa<br>Phe Ser Met Gly Ser Val Val Ala Gly Leu Leu Lys Arg Leu Ile Glu<br>305                          310                      315                  320 | 960 |
| atg act gct gag tac gcc tgc aca agg aaa cag ttt aac aag agg ctc<br>Met Thr Ala Glu Tyr Ala Cys Thr Arg Lys Gln Phe Asn Lys Arg Leu<br>                    325                      330                    335 | 1008 |
| agt gaa ttt gga ttg att cag gag aaa ttt gca ctg atg gct cag aag<br>Ser Glu Phe Gly Leu Ile Gln Glu Lys Phe Ala Leu Met Ala Gln Lys<br>            340                    345                    350 | 1056 |
| gct tac gtc atg gag agt atg acc tac ctc aca gca ggg atg ctg gac<br>Ala Tyr Val Met Glu Ser Met Thr Tyr Leu Thr Ala Gly Met Leu Asp<br>355                          360                      365 | 1104 |
| caa cct ggc ttt ccc gac tgc tcc atc gag gca gcc atg gtg aag gtg<br>Gln Pro Gly Phe Pro Asp Cys Ser Ile Glu Ala Ala Met Val Lys Val<br>370                          375                      380 | 1152 |
| ttc agc tcc gag gcc gcc tgg cag tgt gtg agt gag gcg ctg cag atc<br>Phe Ser Ser Glu Ala Ala Trp Gln Cys Val Ser Glu Ala Leu Gln Ile<br>385                          390                      395                  400 | 1200 |
| ctc ggg ggc ttg ggc tac aca agg gac tat ccg tac gag cgc ata ctg<br>Leu Gly Gly Leu Gly Tyr Thr Arg Asp Tyr Pro Tyr Glu Arg Ile Leu<br>                    405                      410                    415 | 1248 |
| cgt gac acc cgc atc ctc ctc atc ttc gag gga acc aat gag att ctc<br>Arg Asp Thr Arg Ile Leu Leu Ile Phe Glu Gly Thr Asn Glu Ile Leu<br>            420                    425                    430 | 1296 |
| cgg atg tac atc gcc ctg acg ggt ctg cag cat gcc ggc cgc atc ctg<br>Arg Met Tyr Ile Ala Leu Thr Gly Leu Gln His Ala Gly Arg Ile Leu<br>435                          440                      445 | 1344 |
| act acc agg atc cat gag ctt aaa cag gcc aaa gtg agc aca gtc atg<br>Thr Thr Arg Ile His Glu Leu Lys Gln Ala Lys Val Ser Thr Val Met<br>450                          455                      460 | 1392 |
| gat acc gtt ggc cgg agg ctt cgg gac tcc ctg ggc cga act gtg gac<br>Asp Thr Val Gly Arg Arg Leu Arg Asp Ser Leu Gly Arg Thr Val Asp<br>465                          470                      475                  480 | 1440 |
| ctg ggg ctg aca ggc aac cat gga gtt gtg cac ccc agt ctt gcg gac<br>Leu Gly Leu Thr Gly Asn His Gly Val Val His Pro Ser Leu Ala Asp<br>                    485                      490                    495 | 1488 |
| agt gcc aac aag ttt gag gag aac acc tac tgc ttc ggc cgg acc gtg<br>Ser Ala Asn Lys Phe Glu Glu Asn Thr Tyr Cys Phe Gly Arg Thr Val<br>            500                    505                    510 | 1536 |
| gag aca ctg ctg ctc cgc ttt ggc aag acc atc atg gag gag cag ctg<br>Glu Thr Leu Leu Leu Arg Phe Gly Lys Thr Ile Met Glu Glu Gln Leu<br>515                          520                      525 | 1584 |
| gta ctg aag cgg gtg gcc aac atc ctc atc aac ctg tat ggc atg acg<br>Val Leu Lys Arg Val Ala Asn Ile Leu Ile Asn Leu Tyr Gly Met Thr<br>530                          535                      540 | 1632 |
| gcc gtg ctg tcg cgg gcc agc cgc tcc atc cgc att ggg ctc cgc aac<br>Ala Val Leu Ser Arg Ala Ser Arg Ser Ile Arg Ile Gly Leu Arg Asn<br>545                          550                      555                  560 | 1680 |
| cac gac cac gag gtt ctc ttg gcc aac acc ttc tgc gtg gaa gct tac<br>His Asp His Glu Val Leu Leu Ala Asn Thr Phe Cys Val Glu Ala Tyr<br>                    565                      570                    575 | 1728 |
| ttg cag aat ctc ttc agc ctc tct cag ctg gac aag tat gct cca gaa<br>Leu Gln Asn Leu Phe Ser Leu Ser Gln Leu Asp Lys Tyr Ala Pro Glu<br>            580                    585                    590 | 1776 |
| aac cta gat gag cag att aag aaa gtg tcc cag cag atc ctt gag aag<br>Asn Leu Asp Glu Gln Ile Lys Lys Val Ser Gln Gln Ile Leu Glu Lys<br>595                          600                    605 | 1824 |

```
cga gcc tat atc tgt gcc cac cct ctg gac agg aca tgc      1863
Arg Ala Tyr Ile Cys Ala His Pro Leu Asp Arg Thr Cys
    610             615             620
```